(12) United States Patent
Biesecker et al.

(10) Patent No.: US 7,964,572 B2
(45) Date of Patent: *Jun. 21, 2011

(54) HIGH AFFINITY NUCLEIC ACID LIGANDS OF COMPLEMENT SYSTEM PROTEINS

(75) Inventors: Gregory Biesecker, Boulder, CO (US); Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/288,622

(22) Filed: Nov. 28, 2005

(65) Prior Publication Data

US 2006/0079477 A1    Apr. 13, 2006

Related U.S. Application Data

(63) Continuation of application No. 10/435,750, filed on May 8, 2003, now abandoned, which is a continuation of application No. 10/037,282, filed on Jan. 3, 2002, now Pat. No. 6,566,343, which is a continuation of application No. 09/163,025, filed on Sep. 29, 1998, now Pat. No. 6,395,888, which is a continuation-in-part of application No. 09/023,228, filed on Feb. 12, 1998, now Pat. No. 6,140,490, which is a continuation-in-part of application No. PCT/US97/01739, filed on Jan. 30, 1997, which is a continuation-in-part of application No. 08/595,335, filed on Feb. 1, 1996, now abandoned.

(51) Int. Cl.
*C12N 15/11* (2006.01)

(52) U.S. Cl. ........................................................ 514/44
(58) Field of Classification Search .................. None
See application file for complete search history.

(56) References Cited

U.S. PATENT DOCUMENTS

| | | | |
|---|---|---|---|
| 3,710,795 A | 1/1973 | Higuchi et al. |
| 4,683,195 A | 7/1987 | Mullis et al. |
| 4,816,567 A | 3/1989 | Cabilly et al. |
| 4,935,363 A | 6/1990 | Brown et al. |
| 4,959,309 A | 9/1990 | Dattagupta et al. |
| 5,070,010 A | 12/1991 | Hsu |
| 5,212,071 A | 5/1993 | Fearon et al. |
| 5,244,805 A | 9/1993 | Miller |
| 5,252,216 A | 10/1993 | Folena-Wasserman et al. |

(Continued)

FOREIGN PATENT DOCUMENTS

EP    592035    4/1994

(Continued)

OTHER PUBLICATIONS

Pestourie et al. (2005) Biochimie 87:921-930.*

(Continued)

*Primary Examiner* — Seam McGarry
*Assistant Examiner* — Terra Cotta Gibbs
(74) *Attorney, Agent, or Firm* — Swanson & Bratschun, L.L.C.

(57) ABSTRACT

Methods are described for the identification and preparation of high-affinity Nucleic Acid Ligands to Complement System Proteins. Methods are described for the identification and preparation of high affinity Nucleic Acid Ligands to Complement System Proteins C1q, C3 and C5. Included in the invention are specific RNA ligands to C1q, C3 and C5 identified by the SELEX method.

27 Claims, 7 Drawing Sheets

U.S. PATENT DOCUMENTS

| | | | |
|---|---|---|---|
| 5,256,642 A | 10/1993 | Fearon et al. |
| 5,262,564 A | 11/1993 | Kun et al. |
| 5,270,163 A | 12/1993 | Gold et al. |
| 5,338,671 A | 8/1994 | Scalice et al. |
| 5,428,149 A | 6/1995 | Eaton et al. |
| 5,456,909 A | 10/1995 | Marsh, Jr. et al. |
| 5,459,015 A | 10/1995 | Janjic et al. |
| 5,472,841 A | 12/1995 | Jayasena et al. |
| 5,472,939 A | 12/1995 | Fearon et al. |
| 5,475,096 A | 12/1995 | Gold et al. |
| 5,476,766 A | 12/1995 | Gold et al. |
| 5,496,938 A | 3/1996 | Gold et al. |
| 5,503,978 A | 4/1996 | Schneider et al. |
| 5,527,894 A | 6/1996 | Gold et al. |
| 5,543,293 A | 8/1996 | Gold et al. |
| 5,567,588 A | 10/1996 | Gold et al. |
| 5,580,737 A | 12/1996 | Polisky et al. |
| 5,635,615 A | 6/1997 | Allen et al. |
| 5,637,459 A | 6/1997 | Burke et al. |
| 5,648,214 A | 7/1997 | Nieuwlandt et al. |
| 5,654,151 A | 8/1997 | Allen et al. |
| 5,660,985 A | 8/1997 | Pieken et al. |
| 5,668,264 A | 9/1997 | Janjic et al. |
| 5,672,695 A | 9/1997 | Eckstein et al. |
| 5,674,685 A | 10/1997 | Janjic et al. |
| 5,683,867 A | 11/1997 | Biesecker et al. |
| 5,698,687 A | 12/1997 | Eckstein et al. |
| 5,705,337 A | 1/1998 | Gold et al. |
| 5,707,796 A | 1/1998 | Gold et al. |
| 5,723,323 A | 3/1998 | Kauffman et al. |
| 5,723,750 A | 3/1998 | Stubbs et al. |
| 5,726,017 A | 3/1998 | Lochrie et al. |
| 5,763,173 A | 6/1998 | Gold et al. |
| 5,763,177 A | 6/1998 | Gold et al. |
| 5,789,157 A | 8/1998 | Jensen et al. |
| 5,817,635 A | 10/1998 | Eckstein et al. |
| 5,840,858 A | 11/1998 | Smith et al. |
| 5,856,297 A | 1/1999 | Fearon et al. |
| 5,858,969 A | 1/1999 | Marsh, Jr. et al. |
| 5,861,254 A | 1/1999 | Schneider et al. |
| 5,919,455 A | 7/1999 | Greenwald et al. |
| 5,932,462 A | 8/1999 | Harris et al. |
| 5,958,691 A | 9/1999 | Pieken et al. |
| 5,981,481 A | 11/1999 | Fearon et al. |
| 6,011,020 A | 1/2000 | Gold et al. |
| 6,013,443 A | 1/2000 | Heilig et al. |
| 6,020,130 A | 2/2000 | Gold et al. |
| 6,051,698 A | 4/2000 | Janjic et al. |
| 6,054,297 A | 4/2000 | Carter et al. |
| 6,057,131 A | 5/2000 | Marsh, Jr. et al. |
| 6,113,906 A | 9/2000 | Greenwald et al. |
| 6,140,490 A | 10/2000 | Biesecker et al. |
| 6,147,204 A | 11/2000 | Gold et al. |
| 6,169,068 B1 | 1/2001 | Levin et al. |
| 6,207,816 B1 | 3/2001 | Gold et al. |
| 6,229,002 B1 | 5/2001 | Janjic et al. |
| 6,251,588 B1 | 6/2001 | Shannon et al. |
| 6,278,039 B1 | 8/2001 | Johnson et al. |
| 6,316,604 B1 | 11/2001 | Fearon et al. |
| 6,355,245 B1 | 3/2002 | Evans et al. |
| 6,395,888 B1 | 5/2002 | Biesecker et al. |
| 6,566,343 B2 | 5/2003 | Biesecker et al. |
| 6,573,299 B1 | 6/2003 | Petrus |
| 7,538,211 B2 | 5/2009 | Benedict et al. |
| 7,579,456 B2 | 8/2009 | Benedict et al. |
| 2004/0180360 A1 | 9/2004 | Wilson et al. |
| 2004/0197804 A1 | 10/2004 | Keefe et al. |
| 2004/0249130 A1 | 12/2004 | Stanton et al. |
| 2005/0037394 A1 | 2/2005 | Keefe et al. |
| 2005/0214308 A1 | 9/2005 | Ashkenazi et al. |
| 2006/0018871 A1 | 1/2006 | Benedict et al. |
| 2006/0030535 A1 | 2/2006 | Healy et al. |
| 2006/0079477 A1 | 4/2006 | Biesecker et al. |
| 2007/0048248 A1 | 3/2007 | Benedict et al. |
| 2007/0117112 A1 | 5/2007 | Diener et al. |
| 2009/0269356 A1 | 10/2009 | Epstein et al. |

FOREIGN PATENT DOCUMENTS

| | | |
|---|---|---|
| GB | 2 183 661 A | 6/1987 |
| RU | 2222345 C2 | 1/2004 |
| WO | WO 89/06694 | 7/1989 |
| WO | WO 91/14436 | 10/1991 |
| WO | WO 91/19813 | 12/1991 |
| WO | WO 92/05285 | 4/1992 |
| WO | WO 92/07065 | 4/1992 |
| WO | WO 92/14842 | 9/1992 |
| WO | WO 92/14843 | 9/1992 |
| WO | WO 95/07364 | 3/1995 |
| WO | WO 97/28178 | 8/1997 |
| WO | WO 97/42317 | 11/1997 |
| WO | WO 98/18480 | 5/1998 |
| WO | WO 99/41271 | 8/1999 |
| WO | WO 2006/050498 | 5/2006 |

OTHER PUBLICATIONS

Acton (1993) J. Biol. Chem. 268:3530.
Biesecker (1996) Molecular Immunology 33 Supl. 1: 86.
Eikelenboom et al. (1982) Acta Neuropathol. (Berl.) 57:239.
Ellington and Szostak, (May 1990) Abstract of Papers Presented at the 1990 Meeting on RNA Processing, Cold Spring Harbor Laboratory, Cold Spring Harbor, N.Y., p. 84.
Jiang et al. (1992) The Journal of Biological Chemistry, 267(35):25597-25601.
Joyce (1989) Gene 82:83.
Joyce et al. (1989) Nucleic Acids Research 17:711.
Kinzler et al. (1989) Nucleic Acids Research 17:3645.
Kramer et al. (1974) J. Mol. Biol. 89:719.
Levisohn (1968) Proc. Natl. Acad. Sci. USA 60:866.
Levisohn et al. (1969) Proc. Natl. Acad. Sci. USA 63:805.
Morgan (1995) Crit. Rev. Clin. Lab. Sci. 32:265.
Oliphant et al. (1986) Gene 44:177.
Oliphant et al. (1987) Methods in Enzymology 155:568.
Oliphant et al. (1988) Nucleic Acids Research 16:7673.
Oliphant et al. (1989) Mol. Cell. Biol. 9:2944.
Robertson et al. (Mar. 1990) Nature 344:467.
Rosenberg et al. (1988) J. Rheumatol. 15:1091.
Szostak (1988) Redesigning the Molecules of Life, (S.A. Benner Ed.) Springer-Verlag Berlin Heidelberg, pp. 87-113, Astructure and Activity of Ribozymes.
Thiesen et al. (1990) Nucleic Acids Research 18:3203.
Van Schravendijk et al. (1982) Mol. Immunol. 19:1179.
Biesecker et al. Derivation of RNA aptamer inhibitors of human C5 (Apr. 1998) Molecular Immunology 35(6-7):334 (abstract only).
Matis, Louis A. and Rollins, Scott A., "Complement-specific antibodies: Designing novel anti-inflammatories," (1995) Nature Medicine, vol. 1, No. 8, pp. 839-842.
Patt, Anita et al., "Xanthine Oxidase-derived Hydrogen Peroxide Contributes to Ischemia Reperfusion-induced Edema in Gerbil Brains," (1988) Journal of Clinical Investigation, vol. 81, pp. 1556-1562.
Pellas, T.C. and Wennogle, L.P., "C5a Receptor Antagonists," (1999) Current Pharmaceutical Design, vol. 5, pp. 737-755 (Abstract).
Rinder, Christine S. et al., "Blockade of C5a and C5b-9 Generation Inhibits Leukocyte and Platelet Activation during Extracorporeal Circulation," (1995) Journal of Clinical Investigation, vol. 96, pp. 1564-1572.
Wang, Yi et al., "Anti-C5 monoclonal antibody therapy prevents collagen-induced arthritis and ameliorates established disease," (1995) Proceedings of the National Academy of Sciences, vol. 92, pp. 8955-8959.
Acosta et al., "Molecular basis for a link between complement and the vascular complications of diabetes", PNAS (2002) 97(10): 5450-5455.
Agrawal et al., "Mixed-backbone oligonucleotides as second generation antisense oligonucleotides: In vitro and in vivo studies", Proc. Natl. Acad. Sci. USA (1997) 94: 2620-2625.
Agrawal et al., "Novel enzymatic and immunological responses to oligonucleotides", Tox. Lett. (1995) 82/83: 431-434.

Ahmed et al., "Microarray analysis of changes in mRNA levels in the rat retina after experimental elevation of intraocular pressure", Invest. Ophthalmol. Vis. Sci. (2004) 45(4):1247-1254.

Albrecht et al., "C5a-Induced Gene Expression in Human Umbilical Vein Endotheilial Cells", Am. J. Pathology (2004) 164(3): 849-859.

Allegretti et al., "Targeting C5a: Recent Advances in Drug Discovery", Curr. Med. Chem. (2005) 12: 217-236.

Altschul et al., "Basic Local Alignment Search Tool", J. Mol. Biol. (1990) 215: 403-410.

Altschul et al., "Gapped BLAST and PSI-BLAST a new generation of protein database search programs", Nuc. Acids Res. (1997) 25(17): 3389-3402.

Ambati et al., "An animal model of age-related macular degeneration in senescent Cc1-2- or Ccr-2-deficient mice", Nature Medicine (2003) 9(11):1390-1397.

Ambati et al., "Age-related macular degeneration: etiology, pathogenesis and therapeutic strategies", Sur. Ophthalmol. (2003) 48(3):257-293.

Andrake, "DNA polymerase of bacteriophage T4 is an autogenous translational repressor", Proc. Natl. Acad. Sci. USA (1988) 85: 7942-7946.

Baldwin et al., "Complement in Organ Transplantation: Contributions to Inflammation, Injury, and Rejection", Transplantation (1995) 59(6): 797-808.

Bardak, "The demonstration of serum interleukin 6-8, tumor necrosis factor-alpha, complement, and immunoglobulin levels in Behcet's disease with ocular involvement", Ocul. Immunol. Inflamm. (2004) 12(1):53-58.

Bardenstein, "Blockage of complement regulators in the conjunctiva and within the eye leads to massive inflammation and iritis", Immunology (2001) 104(4):423-430.

Baudouin et al, "Immunohistopathologic Findings in Proliferative Diabetic Retinopathy", Am. J. Ophthalmol. (1988) 105: 383-388.

Bednar et al., "Activation of complement by tissue plasminogen activator, but not acute cerebral ischemia, in a rabbit model of thromboembolic stroke", J. Neurosurg. (1997) 86: 139-142.

Bhole, D. and Stahl, G.L., "Therapeutic potential of targeting the complement cascade in critical care medicine", Crit. Care Med. (2003) 31(1 Suppl.): S97-S104.

Biesecker et al., "Derivation of RNA aptamer inhibitors of human complement C5", Immunopharmacology (1999) 42: 219-230.

Biesecker et al , "Inhibition of Acute Passive Transfer Experimental Autoimmune Myasthenia Gravis with Fab Antibody to Complement C6", J. Immunol. (1989) 142:2654-2659.

Biesecker, "Renal Localization of the Membrane Attack Complex in Systemic Lupus Erythematosus Nephritis", J. Exp. Med. (1981) 154: 1779-1794.

Bora et al., "Role of complement and complement membrane attack complex in laser-induced choroidal neovascularization", J. Immunol. (2005) 174(1):491-497.

Bora et al., "Complement activation via alternative pathway is critical in the development of laser-induced choroidal neovascularization: role of factor B and factor H", J. Immunol. (2006) 177(3): 1872-1878.

Brauer et al., "The Contribution of Terminal Complement Components to Acute and Hyperacute Allograft Rejection in the Rat", Transplantation (1995) 59(2): 288-293.

Brawman-Mintzer et al., "Distribution of Complement in the Sclera", Invest. Ophthalmol. Vis. Sci. (1989) 30(10):2240-2244.

Brus et al., "Physiochemical and Biological Characterization of Polyethylenimine-graft-Poly(ethylene glycol) Block Copolymers as a Delivery System for Oligonucleotides and Ribozymes", Bioconjugate Chem. (2004) 15: 677-684.

Burmeister et al., "Direct in vitro selection of a 2'-O-methyl aptamer to VEGF", Chemistry and Biology (2005) 12:25-33.

Carey et al., "Sequence-specific interaction of R17 coat protein with its ribonucleic acid binding site", Biochem. (1983) 22: 2601-2610.

Carter et al., "Humanization of an anti-p185Her2 antibody for human cancer therapy", Proc. Natl Acad. Sci. USA (1992) 89:4285-4289.

Chelliserrykattil et al., "Evolution of a T7 RNA polymerase variant that transcribes 2'-O-methyl RNA", Nature Biotech. (2004) 9:1155-1160.

Chen et al., "Pharmacologic C5-Complement Suppression Reduces Blood Loss During On-Pump Cardiac Surgery", J. Card. Surg. (2005) 20: 35-41.

Chen et al., "Selection of high-affinity RNA ligands to reverse transcriptase. Inhibition of cDNA synthesis and RNase H activity", Biochem. (1994) 33: 8746-8756.

Chothia et al., "Canonical Structures of thte Hypervariable Regions of Immunoglobulins", J. Mol. Biol. (1987) 196:901-917.

Cohen et al., "Interactions of hormonal steroids with nucleic acids: A specific requirement for guanine", Proc. Natl. Acad. Sci. USA (1969) 63: 458-464.

Cotten et al., "2'-O-methyl, 2'O-ethyl oligoribonucleotides and phosphorothioate oligodeoxyribonucleotides as inhibitors of the in vitro U7 snRNP-dependent mRNA processing event," Nuc. Acids Res. (1991) 19(10): 2629-2635.

Cuchacovich et al., "Bechet's disease patients present high levels of deglycolyslted anti-lipoteichoic acid IgG and high Il-8 production after lipoteichoic acid stimulation", Clin. Exp. Rheumatol. (2005) 23:S27-S34.

Davis et al., "Identifying consensus patterns and secondary structure in SELEX sequence sets", Methods in Enzymology (1996) 267: 302-314.

De Bruijn et al., "Human complement component C3: cDNA coding sequence and derived primary structure", Proc. Natl. Acad. Sci. USA (1985) 82:708-712.

Dehouck et al., "Blood-brain barrier in vitro—rapid evaluation of strategies for achieving drug targeting to the central nervous system", Biol. Physiology of the Blood Brain Barrier, (1996) Couraud and Scherman eds., 23: 143-146.

Drozdova, "Immunologic peculiarities of uveitis concurrent with systemic pathologies", Vestn. Oftalmol. (2004) 120(4):24-26 (English abstract only).

Edwards et al., "Complement Factor H polymorphism and age-related macular degeneration", Science (2005) 308(5720):421-424.

Evans et al., "In vitro and in vivo Inhibition of Complement Activity by a Single-Chain Fv Fragment Recognizing Human C5", Mol. Immunol. (1995) 32(16): 1183-1195.

Fitch et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass", Circulation (1999) 100: 2499-2506.

Fitzwater et al., "A SELEX primer", (1996) Methods in Enzymology 267: 275-301.

Fleisig et al. "Pexelizumab—a C5 complement inhibitor for use in both acute myocardial infarction and cardiac surgery with cardiopulmonary bypass" Expert Opin. Biol. Ther. (2005) 5(6):833-9.

Froehler et al., "Synthesis of DNA via deoxynucleoside H-phosphonate intermediates," Nuc. Acids Res. (1986) 14(13): 5399-5467.

Froehler, "Deoxynucleoside H-Phosphonate Diester Intermediates in the Synthesis of Internucleotide Phosphate Analogues", Tet. Lett. (1986) 27(46): 5575-5578.

Gath et al., "The blood-CSF barrier in vitro", Biol. and Physiology of the Blood Brain Barrier, (1996) Couraud and Scherman eds., 25: 153-158.

Gong et al., "Tubing Loops as a Model for Cardiopulmonary Bypass Circuits: Both the Biomaterial and the Blood-Gas Phase Interfaces Induce Complement Activation in an In Vitro Model", J. Clin. Immunol. (1996) 16(4): 222-229.

Gerl et al., "Extensive Deposits of Complement C3d and C5b-9 in the Choriocapillaries of Eyes of Patients with Diabetic Retinopathy", Invest. Opthalmol. Vis. Sci. (2002) 43(4): 1104-1108.

Granger et al., "Pexeluzimab, an Anti-C5 complement Antibody, as Adjunctive Therapy to Primary Percutaneous Coronary Intervention in Acute Myocardial Infarction", Circulation (2003) 108: 1184-1190.

Green et al., "Nuclease-resistant nucleic acid ligands to vascular permeability factor/vascular endothelial growth factor", Chemistry & Biology (1995) 2: 683-695.

Greenwald et al., "Highly Water Soluble Taxol Derivatives: 7-Polythylene Glycol Carbamates and Carbonates", J. Org. Chem. (1995) 60: 331-336.

Hageman et al., "A common haplotype in the complement regulatory gene factor H (HF1/CFH) predisposes individuals to age-related macular degeneration", PNAS (2005) 102(2):7227-7232.

Haines et al., "Complement Factor H variant increases the risk of age-related macular degeneration", Science (2005) 308(5720):419-421.

Hangen et al., "Complement Levels in Septic Primates Treated with Anti-C5a Antibodies", J. Surg. Res. (1989) 46: 195-199.

Hansen et al., "Association Between Mannose-Binding Lectin and Vascular Complications in Type-1 Diabetes", Diabetes (2004) 53: 1570-1576.

Harris et al., "Effect of Pegylation on Pharmaceuticals", Nature Rev (2003) 2: 214-221.

Haviland et al., "Complete cDNA sequence of human complement Pro-C5: evidence of truncated transcripts derived from a single copy gene", J. Immunol. (1991) 145(1):362-368.

Haviland et al., "Structure of the Murine Fifth Complement Component (C5) Gene", J. Biol. Chem. (1991) 266(18): 11818-11825.

Henry et al., "Activation of the Alternative Pathway of Complement by a Phosphorothioate Oligonucleotide: Potential Mechanism of Action", J. Pharm. Exp. Ther. (1997) 281(2): 810-816.

Hirose et al., "Rapid Synthesis of Trideoxyribonucleotide Blocks", Tet. Lett. (1978) 28: 2449-2452.

Hobbs et al., "Polynucleotides Containing 2'-Amino-2'-deoxyribose and 2'-Azido-2'-deoxyribose", Biochemistry (1973) 12(25): 5138-514.

Homeister and Lucchesi, "Complement Activation and Inhibition in Myocardial Ischemia and Reperfusion Injury" Annu. Rev. Pharmacol. Toxicol. (1994) 34: 17-40.

Homeister et al. "Soluble Complement Receptor Type 1 prevents human complement-mediated damage of the rabbit isolated heart" (1993) J. Immunol. 150:1055-64.

Jha et al., "The complement system plays a critical role in the development of experiemental autoimmune anterior uveitis", (2006) Invest. Ophthalmol. Vis. Sci. 47(3):1030-1038.

Jones et al., "Replacing the complementarity-determining regions in a human antibody with those from a mouse" Nature 321:552-525.

Kacian et al., "A replicating RNA molecule suitable for a detailed analysis of extracellular evolution and replication", Proc. Natl. Acad. Sci USA (1972) 69: 3038-3042.

Kadonaga et al., "Affinity purification of sequence-specific DNA binding proteins", Proc. Natl. Acad. Sci. USA (1986) 83: 5889-5893.

Kandimalla et al., "Effects of Phosphorothioate Oligodeoxyribonucleotide and Oligoribonucleotides on Human Complement and Coagulation", Bio. Med. Chem. Lett. (1998) 8: 2103-2108.

Kasp et al., "Circulating immune complexes may play a regulatory and pathogenic role in experimental autoimmune uveoretinitis", (1992) Clin. Exp. Immunol. 88(2):307-312.

Kellogg et al., "Taqstart antibody.TM.: 'Hot start' PCR facilitated by a neutralizing monoclonal antibody directed against taq DNA polymerase", BioTechniques (1994) 16(6): 1134-1137.

Kijlstra et al., "Immunological factors in the pathogenesis and treatment of age-related macular degeneration", Ocular Immunol. Inflam. (2005) 13:3-11.

Kinzler and Vogelstein, "The GLI gene encodes a nuclear protein which binds specific sequences in the human genome", Mol. Cell. Biol . (1990) 10: 634-642.

Klein et al., "Complement Factor H Polymorphism in age-related macular degeneration", Science (2005) 308(5720):385-389.

Koehler et al., "Continuous cultures of fused cells secreting antibody of predefined specifity", Nature (1975) 256(5517):495-497.

Kroshus et al., "Complement Inhibition with an Anti-C5 Monoclonal Antibody Prevents Acute Cardiac Tissue Injury in an Ex Vivo Model of Pig-to-Human Xenotranplantation", Transplantation (1995) 60(11): 1194-1202.

Krzystolik et al., "Prevention of experimental choroidal neovascularizatio with intravitreal anti-vascular endothelial growth factor antibody fragment", Arch. Ophthalmol. (2002) 120:338-346.

Kuehn, "Gene discovery provides clues to cause of age-related macular degeneration", JAMA (2005) 293(15):1841-1845.

La Hey et al., "Immune deposits in iris biopsy specimens from patients with Fuchs' Heterochromic Iridocyclitis", Am. J. Ophthalmol. (1992) 113(1):75-80.

Larsson et al , "Inhibition of complement activation by soluble recombinant CR1 under conditions resembling those in a cardiopulmonary circuit: reduced up-regulation of CD11b and complete abrogation of the binding of PMNs to the biomaterial surface", Immunopharmacology (1997) 38:119-127.

Lestienne et al., "Inhibition of human leucocyte elastase by polynucleotides", Biochimie (1983) 65: 49-52.

Ma and Ptashne, "A new class of yeast transcriptional activators", Cell (1987) 51: 113-119.

Mahaffey et al., "Effect of Pexeluzimab, an Anti-C5 Complement Antibody, as Adjunctive Therapy to Fibrinolysis in Acute Myocardial Infarction", Circulation (2003) 108: 1176-1183.

Makrides et al., "Therapeutic Inhibition of the Complement System", Pharmacol. Rev. (1998) 50(1): 59-87.

Maniatis et al., "Molecular Cloning: A Laboratory Manual", (1982) Cold Spring Harbor, NY p. 118.

Maniatis et al., "Regulation of inducible and tissue-specific gene expression", Science (1987) 236: 1237-1245.

Mathew, J. et al. "Preliminary report of the effects of Pexelizumab on neurocognitive decline after coronary artery bypass graft surgery" (2004) Stroke 35:2335-2339.

Mayer G. et al. "Aptamers in Research and Drug Development", BioDrugs (2004) 18(6):315-359.

McCafferty et al., "Phage antibodies: filamentous phage displaying antibody variable domains", Nature (1990) 348:552-554.

McGinnis and Madden, "BLAST: at the core of a powerful and diverse set of sequence analysis tools", Nuc. Acids Res. (2004) 32: W20-W25.

Miele et al., "Autocatalytic replication of a recombinant RNA", J. Mol. Biol. (1983) 171: 281-295.

Mills et al., "An extracellular Darwinian experiment with a self-duplicating nucleic acid molecule" , Proc. Natl. Acad. Sci. USA (1967) 58: 217-220.

Mills et al., "Complete nucleotide sequence of a replicating RNA molecule", Science (1973) 180: 916-927.

Min et al., "Search for the optimal sequence of the ribosome binding site by random oligonucleotide-directed mutagenisis" Nuc. Acids Res. (1988) 16: 5075-5088.

Miyahara et al., "Gene microarray analysis of experimental glaucomatous retina from cynomologous monkey", Invest. Ophthalmol. Vis. Sci. (2003) 44:4347-4356.

Mondino et al., "Distribution of hemolytic complement in the normal cornea", Arch. Ophthalmol. (1981) 99(8):1430-1433.

Mondino et al., "Hemolytic complement activity in aqueous humor", Arch. Ophthalmol. (1983) 101(3):465-468.

Monsinjon, T., et al., "Complement and its implications in cardiac ischemia/reperfusion: strategies to inhibit complement," Fundamental & Clinical Pharamcology, (2001) 15:293-306.

Morgan, "Role of Complement in Inflammation and Injury in the Nervous System", Exp. Clin. Immunogenet. (1997) 14: 19-23.

Muesing et al., "Nucleic acid structure and expression of the human AIDS/lymphadenopathy retrovirus", Nature (1985) 313: 450-458.

Mulligan et al., "Requirement and Role of C5a in Acute Lung Inflammatory Injury in Rats", J. Clin. Invest. (1996) 98(2): 503-512.

Nangaku, "Renal microvascular injury induced by antibody to glomerular endothelial cells is mediated by C5b-9", Kidney Int. (1997) 52: 1570-1580.

Needleman and Wunsch, "A General Method Applicable to the Search for Similarities in the Amino Acid Sequence of Two Proteins", J. Mol. Biol. (1970) 48: 443-453.

Nilsson et al., "Compstatin Inhibits Complement and Cellular Activation in Whole Blood in Two Models of Extracorporeal Circulation", Blood (1998) 92(5): 1661-1667.

Nozaki et al., "Drusen complement components C3a and C5a promote choroidal neovascularization", PNAS (2006) 103(7):2328-2333.

O'Connor, "The initiation of inflammation of uveitis", Trans. Ophthalmol. Soc. U.K. (1981) 101(3):297-300.

Orgel, "Selection in vitro", Proc. R. Soc. Lon. (1979) B205: 435-442.

Ou et al., "DNA amplification for direct detection of HIV-1 in DNA of peripheral blood mononuclear cells", Science (1988) 239: 295-297.

Padilla and Sousa, "A Y639F/H784A T7 RNA polymerase double mutant displays superior properties for synthesizing RNAs with non-canonical NTPs", Nuc. Acids Res. (2002) 30(24): e138.

Palestine et al., "Histopathology of the subretinal fibrosis and uveitis syndrome", Ophthalmology (1985) 92(6):838-844.

Pearson and Lipman, "Improved tools for biological sequence comparison", Proc. Natl. Acad. Sci. USA (1988) 85: 2444-2448.

Peng et al., "Role of C5 in the development of airway inflammation, airway hyperresponsiveness, and ongoing airway response", J. Clin. Invest. (2005) 115(6): 1590-1600.

Pietersz et al., "A 16-mer peptide (RQIKIWFQNRRMKWKK) from antennapedia preferentially targets the Class I pathway", Vaccine (2001) 19: 1397-1405.

Planck et al., "Activation of the Complement System by Synthetic DNA Complexes: A Potential Barrier for Intravenous Gene Delivery", Human Gene Therapy (1996) 7: 1437-1446.

Presta et al., "Humanization of an antibody directed against IgE", J. Immunol. (1993) 151:2623-2632.

Riechmann et al., "Reshaping human antibodies for therapy", Nature (1988) 332:323-327.

Ripoche et al., "The complete amino acid sequence of human complement factor H", Biochem. J. (1988) 249:593-602.

Rothbard et al., "Conjugation of arginine oligomers to cyclosporin A facilitates topical delivery and inhibition of inflammation", Nature Medicine (2000) 6(11): 1253-1257.

Rothbard et al., "Arginine-Rich Molecular Transporters for Drug Delivery: Role of Backbone Spacing in Cellular Uptake", J. Med. Chem. (2002) 45: 3612-3618.

Roberts et al., "Chemistry for peptide and protein PEGylation", Advanced Drug Delivery Rev. (2002) 54: 459-476.

Romaniuk et al., "RNA binding site of R17 coat protein", Biochem. (1987) 26: 1563-1568.

Saffhill et al., "In vitro selection of bacteriophage Q.beta. ribonucleic acid variants resistant to ethidium bromide", J. Mol. Biol. (1970) 51: 531-539.

Sakomoto et al., "Class II major histocompatibility complex on melatocytes of Vogt-Koganagi-Harada Disease", Arch. Ophthalmol. (1991) 109(9):1270-1274.

Sellar et al., "Characterization and organization of the genes encoding the A-, B- and C-chains of human complement subcomponent C1q: the complete derived amino acid sequence of human C1q", Biochem. J. (1991) 274:481-490.

Sambrook et al., "Molecular Cloning: A Laboratory Manual", (1989) Cold Spring Harbor, NY, pp. 8.9-8.10.

Shen et al. "Induced expression of neuronal membrane attack complex and cell death by Alzheimer's β-amyloid peptide" (1998) Brain Res. 796(1-2):187-97.

Sepp et al., "Complement factor H variant Y402H is a major risk determinant for geographic atrophy and choroidal neovascularization in smokers and nonsmokers", Invest. Ophthalmol. Vis. Sci. (2006) 47(2):536-540.

Sewell, D. et al., "Complement C3 and C5 play critical roles in traumatic brain cryoinjury: blocking effects on neutrophil extravasation by C5a receptor antagonist," Journal of Neuroimmunology (2004) 155:55-63.

Shernan et al., "Impact of Pexeluzimab, an Anti-C5 Complement Antibody, on Total Mortality and Adverse Cardiovascular Outcomes in Cardiac Surgical Patients Undergoing Cardiopulmonary Bypass", Ann. Thorac. Surg. (2004) 77: 942-950.

Sims et al., "A humanized C18 antibody can block function without cell destruction", J. Immunol. (1993) 151(4):2296-2308.

Singleton et al., "Dictionary of Microbiol. and Molecular Biology", (1987) Wiley & Sons, New York, NY, 2nd ed. p. 493.

Sohn et al., "Chronic Low Level Complement Activation within the Eye is Controlled by Intraocular Complement Regulatory Proteins", Invest. Ophthalmol. Vis. Sci. (2000) 41(11): 3492-3502.

Sood et al., "A rapid and convenient synthesis of poly-thymidylic acid by the modified triester approach", Nuc. Acids Res. (1977) 4(8): 2757-2765.

Sproat et al., "New synthetic routes to synthons suitable for 2'-O-allyloligoribonucleotide assemby", Nuc. Acids Res. (1991) 19(4): 733-738.

Spycher and Nydegger, "Participation of the Blood Platelet in Immune Reactions Due to Platelet-Complement Interaction", Infusionsther Transfusionsmed (1995) 22: 36-43.

Stasi et al., "Complement Component 1Q (C1Q) upregulation in retina of murine, primate and human glaucomatous eyes", Invest. Ophthalmol. Vis. Sci. (2006) 47:1024-1029.

Sun et al., "Target sequence-specific inhibition of HIV-1 replication by ribozymes directed to tat RNA", Nuc. Acids Res. (1995) 23(15): 2909-2913.

Takahashi et al., "Recent Advances in the Immunology of Xenotransplantation", Immunologic Research (1997) 16/3: 273-297.

Tanchou et al., "Monoclonal antibody-mediated inhibition of RNA binding and annealing activities of HIV type 1 nucleocapsid protein", Aids Research and Human Retroviruses (1994) 10: 983-993.

Tezel et al., "Pathogenesis of age-related macular degeenration", Trends Mol. Med. (2004) 10(9):417-420.

Thomas et al., "Inhibition of Complement Activity by Humanized Anti-C5 Antibody and Single-Chain FV", Molecular Immunology (1996) 33(17/18): 1389-1401.

Tucker et al., "Detection and plasma pharmacokinetics of an anti-vascular endothelial growth factor oligonucleotide-aptamer (NX1838) in rhesus monkeys", J. Chromatography B (1999) 732: 203-212.

Uhlenbeck et al., "Interaction of R17 coat protein with its RNA binding site for translational repression", J. Biomolecular Structure and Dynamics (1983) 1: 539-552.

Vakeva et al., "Myocardial Infarction and Apoptosis After Myocardial Infarction Ischemia and Reperfusion: Role of the Terminal Complement Components and Inhibition by Anti-C5 Therapy", Circulation (1998) 97: 2259-2267.

Vergani et al. "Complement activation in uveitis", Br. J. Ophthalmol. (1986) 70(1):60-63.

Verhoeyen et al., "Reshaping human antibodies: grafting an antilysozyem activity", Science (1988) 239:1534-1536.

Vives et al., "A Truncated HIV-1 Tat Protein Basic Domain Rapidly Translocates Through the Plasma Membrane and Accumulates in the Cell Nucleus", J. Biol. Chem. (1997) 272(25): 16010-16017.

Wagner and Hugli "Radioimmunoassay for anaphylatoxins in biological fluids: a sensitive method for determining complement activation" Anal. Biochem. (1984) 136:75.

Wakefield et al., "Association of complement allotype C4B2 with anterior uveitis", Hum. Immunol. (1988) 21(4):233-237.

Wang et al. "Prevention of acute vascular rejection by a functionally blocking anti-C5 monoclonal antibody combined with cyclosporine" (2005) Transplantation 79(9):1121-7.

Wang et al., "Complement Inhibition with an Anti-C5 Monoclonal Antibody Prevents Hyperacute Rejection in a Xenograft Heart Transplantation Model". Transplantation (1999) 68(11): 1643-1651.

Ward, "Role Complement in Lung Inflammatory Injury", Am. J. Pathol. (1996) 149(4): 1079-1086.

Watson et al. (Antisense & Nucleic Acid Drug Development 10:63-75, 2000).

Watson et al., "Molecular Biology of the Gene", (1987) Benjamin/Cummings Publishing Co., Inc. California, pp. 267, 295, 323, 361, 394, 396, 397 and 405.

Webster et al. "Molecular and Cellular characterization of the membrane attack complex, C5b-9, in Alzheimer's Disease" (1997) Neurobiol. Aging 18(4):415-21.

Weisman, HF et al. "Soluble human complement receptor type 1: in vivo inhibitor of complement suppressing post-ischemic myocardial inflammation and necrosis" (1990) Science 249:146-51.

Whiss, "Pexeluzimab Alexion", Curr. Opin. Invest. Drugs (2002) 3(6): 870-877.

Wurzner et al., "Inhibition of Terminal Complement Complex Formation and Cell Lysis by Monoclonal Antibodies", Complement Inflamm. (1991) 8: 328-340.

Yates, JR et al., "Genetic Factors in AMD Study Group. Complement C3 variant and the risk of age-related macular degeneration", N. Engl. J. Med. (2007) 357:553-561.

Yu et al., "Hybrid Oligonucleotides: Synthesis, Biophysical Properties, Stability Studies, and Biological Activity", Bio. Med. Chem. (1996) 4(10): 1685-1692.

Zhang et al., "Early complement activation and decreased levels of glycosylphosphatidylinositol-anchored complement inhibitors in human and experimental diabetic retinopathy", Diabetes (2002) 51: 3499-3504.

* cited by examiner

SEQ ID NO: 160

SEQ ID NO: 193

Figure 5B

HIGH AFFINITY NUCLEIC ACID LIGANDS OF COMPLEMENT SYSTEM PROTEINS

RELATED APPLICATIONS

This application is a continuation of U.S. patent application Ser. No. 10/435,750, filed May 8, 2003, which is a continuation of U.S. patent application Ser. No. 10/037,282, filed Jan. 3, 2002, which is a continuation of U.S. patent application Ser. No. 09/163,025, filed Sep. 29, 1998, now U.S. Pat. No. 6,395,888, which is a continuation-in-part of U.S. patent application Ser. No. 09/023,228, filed Feb. 12, 1998, now U.S. Pat. No. 6,140,490, which is a continuation-in-part of PCT/US97/01739 (International Publication No. WO 97/28178), filed Jan. 30, 1997, which is a continuation-in-part of U.S. patent application Ser. No. 08/595,335, filed Feb. 1, 1996, now abandoned.

FIELD OF THE INVENTION

Described herein are methods for identifying and preparing high-affinity Nucleic Acid Ligands to Complement System Proteins. The method utilized herein for identifying such Nucleic Acid Ligands is called SELEX™, an acronym for Systematic Evolution of Ligands by EXponential enrichment. Described herein are methods for identifying and preparing high-affinity Nucleic Acid Ligands to the Complement System Proteins C1q, C3 and C5. This invention includes high affinity Nucleic Acid Ligands of C1q, C3 and C5. Also disclosed are RNA ligands of C1q, C3 and C5. Also disclosed are Nucleic Acid Ligands that inhibit and/or activate the Complement System. The oligonucleotides of the present invention are useful as pharmaceuticals or diagnostic agents.

BACKGROUND OF THE INVENTION

The complement system comprises a set of at least 20 plasma and membrane proteins that act together in a regulated cascade system to attack extracellular forms of pathogens (Janeway et al. (1994) *Immunobiology: The Immune System in Health and Disease*. Current Biology Ltd, San Francisco, pp. 8:35-8:55; Morgan (1995) Crit. Rev. in Clin Lab. Sci. 32(3):265-298). There are two distinct enzymatic activation cascades, the classical and alternative pathways, and a non-enzymatic pathway known as the membrane attack pathway.

The classical pathway is usually triggered by an antibody bound to a foreign particle. It comprises several components, C1, C4, C2, C3 and C5 (listed by order in the pathway). Initiation of the classical pathway of the Complement System occurs following binding and activation of the first complement component (C1) by both immune and non-immune activators (Cooper (1985) Adv. Immunol. 37:151). C1 comprises a calcium-dependent complex of components C1q, C1r and C1s, and is activated through binding of the C1q component. C1q contains six identical subunits and each subunit comprises three chains (the A, B and C chains). Each chain has a globular head region which is connected to a collagen-like tail. Binding and activation of C1q by antigen-antibody complexes occurs through the C1q head group region. Numerous non-antibody C1q activators, including proteins, lipids and nucleic acids (Reid et al. (1993) *The Natural Immune System: Humoral Factors*. E. Sim, ed. IRL Press, Oxford, p. 151) bind and activate through a distinct site on the collagen-like stalk region.

Non-antibody C1q protein activators include C-reactive protein (CRP) (Jiang et al. (1991) J. Immunol. 146:2324) and serum amyloid protein (SAP) (Bristow et al. (1986) Mol. Immunol. 23:1045); these will activate C1q when aggregated by binding to phospholipid or carbohydrate, respectively. Monomeric CRP or SAP do not activate C1q. C1q is also activated through binding to aggregated β-amyloid peptide (Schultz et al. (1994) Neurosci. Lett. 175:99; Snyder et al. (1994) Exp. Neurol. 128:136), a component of plaques seen in Alzheimer's disease (Jiang et al. (1994) J. Immunol. 152: 5050; Eikelenboom and Stam (1982) Acta Neuropathol (Berl) 57:239; Eikelenboom et al. (1989) Virchows Arch. [B] 56:259; Rogers et al. (1992) Proc. Natl. Acad. Sci. USA 89:10016; Dietzschold et al. (1995) J. Neurol. Sci. 130: 11). C1q activation might also exacerbate the tissue damage associated with Alzheimer's disease. These activators bind C1q on its collagen-like region, distant from the head-group region where immunoglobulin activators bind. Other proteins which bind the C1q collagen-like region include collagen (Menzel et al. (1981) Biochim. Biophys. Acta 670:265), fibronectin (Reid et al. (1984) Acta Pathol. Microbiol. Immunol. Scand. Sect. C 92 (Suppl. 284): 11), laminin (Bohnsack et al. (1985) Proc. Natl. Acad. Sci. USA 82:3824), fibrinogen and fibrin (Entwistle et al. (1988) Biochem. 27:507), HIV rsgp41 (Stoiber et al. (1995) Mol. Immunol. 32:371), actin (Nishioka et al. (1982) Biochem. Biophys. Res. Commun. 108:1307) and tobacco glycoprotein (Koethe et al. (1995) J. Immunol. 155:826).

C1q also binds and can be activated by anionic carbohydrates (Hughes-Jones et al. (1978) Immunology 34:459) including mucopolysaccharides (Almeda et al. (1983) J. Biol. Chem. 258:785), fucans (Blondin et al. (1994) Mol. Immunol. 31:247), proteoglycans (Silvestri et al. (1981) J. Biol. Chem. 256:7383), and by lipids including lipopolysaccharide (LPS) (Zohair et al. (1989) Biochem. J. 257:865; Stoiber et al. (1994) Eur. J. Immunol. 24:294). Both DNA (Schravendijk and Dwek (1982) Mol. Immunol. 19:1179; Rosenberg et al. (1988) J. Rheumatol 15:1091; Uwatoko et al. (1990) J. Immunol. 144:3484) and RNA (Acton et al. (1993) J. Biol. Chem. 268:3530) can also bind and potentially activate C1q. Intracellular components which activate C1q include cellular and subcellular membranes (Linder (1981) J. Immunol. 126:648; Pinckard et al. (1973) J. Immunol. 110: 1376; Storrs et al. (1981) J. Biol. Chem. 256:10924; Giclas et al. (1979) J. Immunol. 122: 146; Storrs et al. (1983) J. Immunol. 131:416), intermediate filaments (Linder et al. (1979) Nature 278:176) and actin (Nishioka et al. (1982) Biochem. Biophys. Res. Commun. 108:1307). All of these interactions would recruit the classical pathway for protection against bacterial (or viral) infection, or as a response to tissue injury (Li et al. (1994) J. Immunol. 152:2995) in the absence of antibody.

A binding site for non-antibody activators including CRP (Jiang et al. (1991) J. Immunol. 146:2324), SAP (Ying et al. (1993) J. Immunol. 150:169), β-amyloid peptide (Newman (1994) Curr. Biol. 4:462) and DNA (Jiang et al. (1992) J. Biol. Chem. 267:25597) has been localized to the amino terminus of C1q A chain at residues 14-26. A synthetic peptide comprising this sequence effectively inhibits both binding and activation. The peptide 14-26 contains several basic residues and matches one of the heparin binding motifs (Yabkowitz et al. (1989) J. Biol. Chem. 264:10888; Cardin et al. (1989) Arteriosclerosis 9:21). The peptide is also highly homologous with peptide 145-156 in collagen-tailed acetylcholinesterase; this site is associated with heparin-sulfate basement membrane binding (Deprez et al. (1995) J. Biol. Chem. 270:11043). A second C1q A chain site at residues 76-92 also might be involved in weaker binding; this site is at the junction of the globular head region and the collagen-like tail.

The second enzymatically activated cascade, known as the alternative pathway, is a rapid, antibody-independent route for the Complement System activation and amplification. The alternative pathway comprises several components, C3, Factor B, and Factor D. Activation of the alternative pathway occurs when C3b, a proteolytic cleavage form of C3, is bound to an activating surface such as a bacterium. Factor B is then bound to C3b, and cleaved by Factor D to yield the active enzyme, Ba. The enzyme Ba then cleaves more C3 to C3b, producing extensive deposition of C3b-Ba complexes on the activating surface. When a second C3b is deposited, forming a C3b-C3b-Ba complex, the enzyme can then cleave C5 and trigger activation of the terminal pathway.

The non-enzymatic terminal pathway, also known as the membrane attack pathway, comprises the components C5, C6, C7, C8 and C9. Activation of this membrane attack pathway results when the C5 component is enzymatically cleaved by either the classical or alternative pathway to yield the small C5a polypeptide (9 kDa) and the large C5b fragment (200 kDa). The C5a polypeptide binds to a 7 transmembrane G-protein coupled receptor which was originally described on leukocytes and is now known to be expressed on a variety of tissues including hepatocytes (Haviland et al. (1995) J. Immunol. 154:1861) and neurons (Gasque et al. (1997) Am. J. Pathol. 150:31). The C5a molecule is the primary chemotactic component of the human Complement System and can trigger a variety of biological responses including leukocyte chemotaxis, smooth muscle contraction, activation of intracellular signal transduction pathways, neutrophil-endothelial adhesion (Mulligan et al. (1997) J. Immunol. 158:1857), cytokine and lipid mediator release and oxidant formation. The larger C5b fragment binds sequentially to later components to form the C5b-9 membrane attack complex (MAC). The C5b-9 MAC can directly lyse erythrocytes, and in greater quantities is lytic for leukocytes and is damaging to tissues such as muscle, epithelial and endothelial cells (Stahl et al. (1997) Circ. Res. 76:575). In sublytic amounts the MAC can stimulate upregulation of adhesion molecules, intracellular calcium increase and cytokine release (Ward (1996) Am. J. Pathol. 149:1079). In addition, the C5b-9 MAC can stimulate cells such as endothelial cells and platelets without causing cell lysis. The non-lytic effects of C5a and the C5b-9 MAC are sometimes quite similar.

The Complement System has an important role in defense against bacterial and viral infection, and possibly in immune surveillance against tumors. This is demonstrated most clearly in humans who are deficient in complement components. Individuals deficient in early components (C1, C4, C2 or C3) suffer from recurrent infections, while individuals deficient in late components (C5 through C9) are susceptible to nisseria infection. Complement classical pathway is activated on bacteria by antibodies, by binding of CRP or SAP, or by direct activation through LPS. Complement alternative pathway is activated through binding of C3 to the cell coat. Complement can be activated by viruses through antibodies, and can also be activated on viral infected cells because these are recognized as foreign. In a similar way, transformed cells can be recognized as foreign and can be lysed by the Complement System or targeted for immune clearance.

Activation of the Complement System can and has been used for therapeutic purposes. Antibodies which were produced against tumor cells were then used to activate the Complement System and cause tumor rejection. Also, the Complement System is used together with polyclonal or monoclonal antibodies to eliminate unwanted lymphocytes. For example, anti-lymphocyte globulin or monoclonal anti-T-cell antibodies are used prior to organ transplantation to eliminate lymphocytes which would otherwise mediate rejection.

Although the Complement System has an important role in the maintenance of health, it has the potential to cause or contribute to disease. The Complement System has been implicated in numerous renal, rheumatological, neurological, dermatological, hematological, vascular/pulmonary, allergy, infectious, biocompatibility/shock and other diseases or conditions (Morgan (1995) Crit. Rev. in Clin Lab. Sci. 32(3):265-298; Matis and Rollins (1995) Nature Medicine 1(8):839-842). The Complement System is not necessarily the only cause of the disease state, but it may be one of several factors, each of which contributes to pathogenesis.

Several pharmaceuticals have been developed that inhibit the Complement System in vivo, however, many cause toxicity or are poor inhibitors (Morgan (1995) Crit. Rev. in Clin Lab. Sci. 32(3):265-298). Heparins, K76COOH and nafamstat mesilate have been shown to be effective in animal studies (Morgan (1995) Crit. Rev. in Clin Lab. Sci. 32(3):265-298). Recombinant forms of naturally occurring inhibitors of the Complement System have been developed or are under consideration, and these include the membrane regulatory proteins Complement Receptor 1 (CR1), Decay Accelerating Factor (DAF), Membrane Cofactor Protein (MCP) and CD59.

C5 is an attractive target for the development of a Complement System inhibitor, as both the classical and alternative pathways converge at component C5 (Matis and Rollins (1995) Nature Medicine 1(8):839-842). In addition, inhibition of C5 cleavage blocks both the C5a and the C5b effects on leukocytes and on tissue such as endothelial cells (Ward (1996) Am. J. Pathol. 149:1079); thus C5 inhibition can have therapeutic benefits in a variety of diseases and situations, including lung inflammation (Mulligan et al. (1998) J. Clin. Invest. 98:503), extracorporeal complement activation (Rinder et al. (1995) J. Clin. Invest. 96:1564) or antibody-mediated complement activation (Biesecker et al. (1989) J. Immunol. 142:2654). Matis and Rollins ((1995) Nature Medicine 1(8):839-842) have developed C5-specific monoclonal antibodies as an anti-inflammatory biopharmaceutical. Both C5a and the MAC have been implicated in acute and chronic inflammation associated with human disease, and their role in disease states has been confirmed in animal models. C5a is required for complement- and neutrophil-dependent lung vascular injury (Ward (1997) J. Lab. Clin. Med. 129:400; Mulligan et al. (1998) J. Clin. Invest. 98:503), and is associated with neutrophil and platelet activation in shock and in burn injury (Schmid et al. (1997) Shock 8:119). The MAC mediates muscle injury in acute autoimmune myasthenia gravis (Biesecker and Gomez (1989) J. Immunol. 142:2654), organ rejection in transplantation (Baldwin et al. (1995) Transplantation 59:797; Brauer et al. (1995) Transplantation 59:288; Takahashi et al. (1997) Immunol. Res. 16:273) and renal injury in autoimmune glomerulonephritis (Biesecker (1981) J. Exp. Med. 39:1779; Nangaku (1997) Kidney Int. 52:1570). Both C5a and the MAC are implicated in acute myocardial ischemia (Homeister and Lucchesi (1994) Annu. Rev. Pharmacol. Toxicol. 34:17), acute (Bednar et al. (1997) J. Neurosurg. 86:139) and chronic CNS injury (Morgan (1997) Exp. Clin. Immunogenet. 14:19), leukocyte activation during extracorporeal circulation (Sun et al. (1995) Nucleic Acids Res. 23:2909; Spycher and Nydegger (1995) Infushionsther. Transfusionsmed. 22:36) and in tissue injury associated with autoimmune diseases including arthritis and lupus (Wang et al. (1996) Immunology 93:8563). Thus, inhibiting cleavage of C5 prevents generation of two potentially damaging activities of the Complement System. Inhibiting C5a release eliminates the major Complement System chemotactic and vasoactive activity, and inhibiting C5b formation blocks assembly of the cytolytic C5b-9 MAC. Furthermore, inhibition of C5 prevents injury by the Complement System while leaving intact important Complement System defense and clearance mechanisms, such as C3 and C1q phagocytic activity, clearance of immune complexes and the innate immune response (Carrol (1998) Ann. Rev. Immunol. 16:545).

C3 is an attractive target for the development of a Complement System inhibitor, as it is common to both pathways. Inhibition of C3 using recombinant versions of a natural inhibitors (Kalli et al. (1994) Springer Semin. Immunopathol. 15:417) can prevent cell-mediated tissue injury (Mulligan et al. (1992) J. Immunol. 148:1479) and this has been shown to have therapeutic benefit in diseases such as myocardial infarction (Weisman et al. (1990) Science 249:146) and liver ischemia/reperfusion (Chavez-Cartaya et al. (1995) Transplantation 59:1047). Controlling C3 limits most biological activities of the Complement System. Most natural inhibitors, including DAF, MCP, CR1 and Factor H target C3.

SELEX™

A method for the in vitro evolution of Nucleic Acid molecules with highly specific binding to target molecules has been developed. This method, Systematic Evolution of Ligands by EXponential enrichment, termed the SELEX process, is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is herein specifically incorporated by reference in its entirety. Each of these applications, collectively referred to herein as the SELEX Patent Applications, describes a fundamentally novel method for making a Nucleic Acid Ligand to any desired Target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the Target under conditions favorable for binding, partitioning unbound Nucleic Acids from those Nucleic Acids which have bound specifically to Target molecules, dissociating the Nucleic Acid-Target complexes, amplifying the Nucleic Acids dissociated from the Nucleic Acid-Target complexes to yield a ligand-enriched mixture of Nucleic Acids, then reiterating the steps of binding, partitioning, dissociating and amplifying through as many cycles as desired to yield highly specific, high affinity Nucleic Acid Ligands to the Target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (see also U.S. Pat. No. 5,707,796), describes the use of the SELEX method in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," now abandoned, (see also U.S. Pat. No. 5,763,177) describes a SELEX-based method for selecting Nucleic Acid Ligands containing photoreactive groups capable of binding and/or photo-crosslinking to and/or photoinactivating a Target molecule. U.S. patent application Ser. No. 08/134,028, filed Oct. 7, 1993, entitled "High-Affinity Nucleic Acid Ligands That Discriminate Between Theophylline and Caffeine," now abandoned (see also U.S. Pat. No. 5,580,737), describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now abandoned, (see also U.S. Pat. No. 5,567,588) and U.S. patent application Ser. No. 08/792,075, filed Jan. 31, 1997, entitled "Flow Cell SELEX," now U.S. Pat. No. 5,861,254, describe SELEX-based methods which achieve highly efficient partitioning between oligonucleotides having high and low affinity for a Target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved Nucleic Acid Ligands after the SELEX process has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its Target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now abandoned, (see also U.S. Pat. No. 5,660,985) that describes oligonucleotides containing nucleotide derivatives chemically modified at the 5- and 2'-positions of pyrimidines. U.S. patent application Ser. No. 08/134,028, now U.S. Pat. No. 5,580,737, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing Nucleic Acid Ligands to Complement System Proteins and homologous proteins and the Nucleic Acid Ligands so identified and produced. By homologous proteins it is meant a degree of amino acid sequence identity of 80% or more. Exemplified herein is a method of identifying and producing Nucleic Acid Ligands to C1q, C3 and C5, and the Nucleic Acid Ligands so produced. Nucleic Acid Ligand sequences are provided that are capable of binding specifically to C1q, C3 and C5. In particular, RNA sequences are provided that are capable of binding specifically the C1q, C3 and C5. Specifically included in the invention are the RNA ligand sequences shown in Tables 2-6, 8, 10 and 12-13 and FIGS. 5A-B (SEQ ID NOS: 5-155 and 160-196). Also included in the invention are Nucleic Acid Ligands that inhibit the function of proteins of the Complement System. Specifically included in the invention herein are RNA ligands that inhibit the function of C1q, C3 and C5. Also included are Nucleic Acid Ligands that inhibit and/or activate the Complement System.

Further included in this invention is a method of identifying Nucleic Acid Ligands and Nucleic Acid Ligand sequences to Complement System Proteins comprising the steps of (a) preparing a Candidate Mixture of Nucleic Acids, (b) contacting the Candidate Mixture of Nucleic Acids with a Complement System Protein, (c) partitioning between members of said Candidate Mixture on the basis of affinity to said Complement System Protein, and (d) amplifying the selected molecules to yield a mixture of Nucleic Acids enriched for Nucleic Acid sequences with a relatively higher affinity for binding to said Complement System Protein.

Also included in this invention is a method of identifying Nucleic Acid Ligands and Nucleic Acid Ligand sequences to C1q, C3 and C5, comprising the steps of (a) preparing a Candidate Mixture of Nucleic Acids, (b) contacting the Candidate Mixture of Nucleic Acids with C1q, C3 or C5, (c) partitioning between members of said Candidate Mixture on the basis of affinity to C1q, C3 or C5, and (d) amplifying the selected molecules to yield a mixture of Nucleic Acids enriched for Nucleic Acid sequences with a relatively higher affinity for binding to C1q, C3 or C5.

More specifically, the present invention includes the RNA ligands to C1q, C3 and C5 identified according to the above-described method, including RNA ligands to C1q, including those ligands shown in Table 2 (SEQ ID NOS:5-20) and Table 6 (SEQ ID NOS: 84-155), RNA ligands to C3, including those sequences shown in Table 3 (SEQ ID NOS:21-46), and RNA ligands to C5, including those sequences shown in Table 4 (SEQ ID NOS:47-74), Table 5 (SEQ ID NOS:76-83), Table 8 (SEQ ID NOS:75, 160-162), Table 10 (SEQ ID NOS:163-189), Table 12 (SEQ ID NOS:190-192), Table 13 (SEQ ID NOS:194-196) and FIGS. 5A-B (SEQ ID NOS:160 and 193). Also included are RNA ligands to C1q, C3 and C5 that are substantially homologous to any of the given ligands and that have substantially the same ability to bind C1q, C3 or C5, and inhibit the function of C1q, C3 or C5. Further included in this invention are Nucleic Acid Ligands to C1q, C3 and C5 that have substantially the same structural form as the ligands presented herein and that have substantially the same ability to bind C1q, C3 or C5 and inhibit the function of C1q, C3 or C5.

The present invention also includes modified nucleotide sequences based on the RNA ligands identified herein and mixtures of the same.

BRIEF DESCRIPTION OF THE FIGURES

FIG. 5A shows the proposed structure of the 38mer truncate (SEQ ID NO:160) of clone C6 (SEQ ID NO:51) together with alternative bases.

FIG. 5B shows the 2'-O-methyl substitution pattern of a 38mer truncate (SEQ ID NO:193 of clone C6 (SEQ ID NO:51). Positions where 2'-OMe substitutions can be made are shown in bold. Positions which must be 2'-OH are underlined.

DETAILED DESCRIPTION OF THE INVENTION

Figure 1:
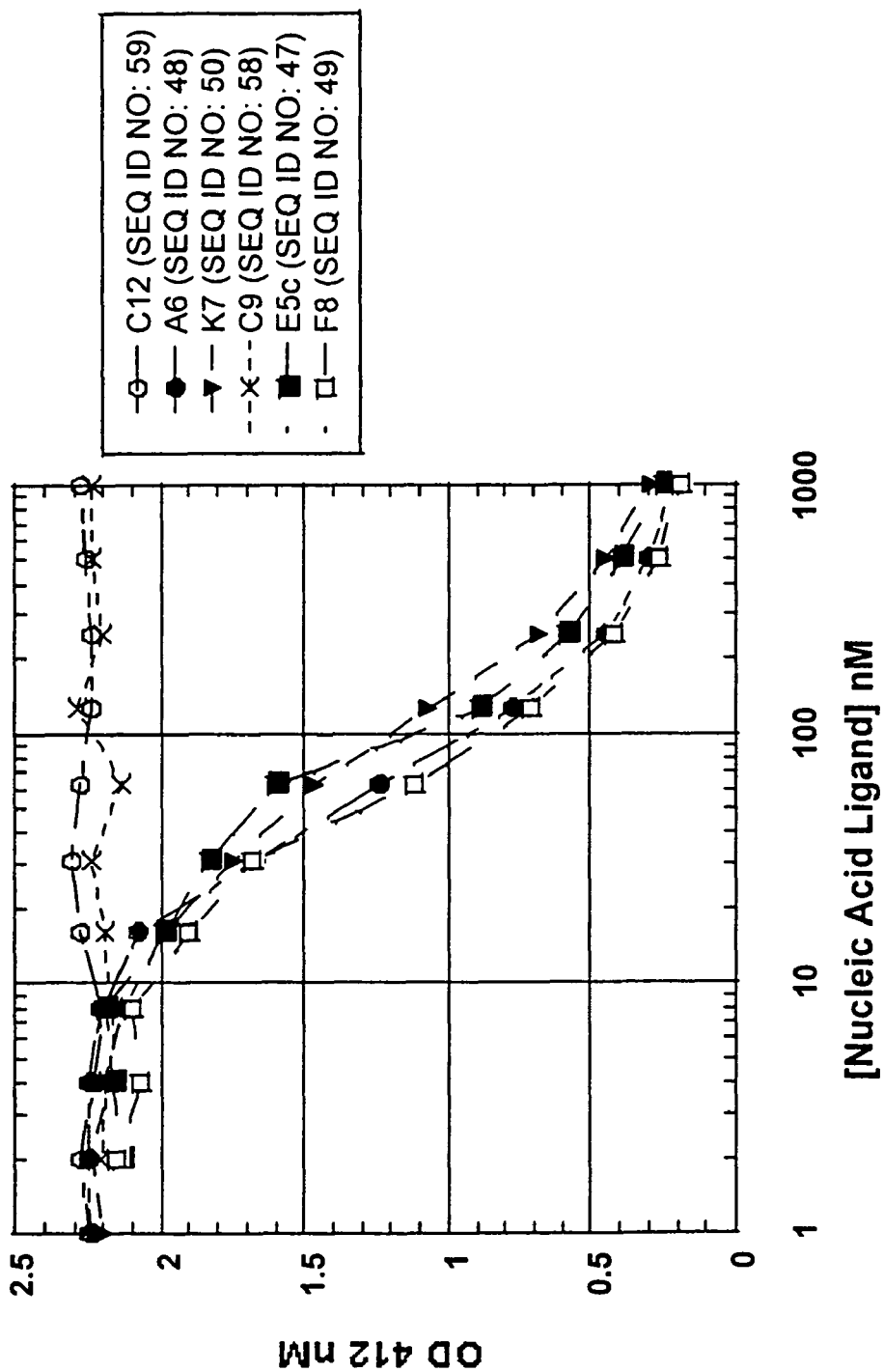
FIG. 1 shows the results of an inhibition assay in which 2'-F RNA ligands C12 (SEQ ID NO:59), A6 (SEQ ID NO:48), K7 (SEQ ID NO:50), C9 (SEQ ID NO:58), E5c (SEQ ID NO:47) and F8 (SEQ ID NO:49) to human C5 were incubated with antibody-coated sheep erythrocytes and whole human serum. The results are presented as optical density (OD) versus concentration of ligand in nM.

This application describes Nucleic Acid Ligands to Complement System Proteins identified generally according to the method known as SELEX. As stated earlier, the SELEX technology is described in detail in the SELEX Patent Applications which are incorporated herein by reference in their entirety. Certain terms used to describe the invention herein are defined as follows:

"Nucleic Acid Ligand" as used herein is a non-naturally occurring Nucleic Acid having a desirable action on a Target. A desirable action includes, but is not limited to, binding of the Target, catalytically changing the Target, reacting with the Target in a way which modifies/alters the Target or the functional activity of the Target, covalently attaching to the Target as in a suicide inhibitor, and facilitating the reaction between the Target and another molecule. In the preferred embodiment, the desirable action is specific binding to a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule. Nucleic Acid Ligands include Nucleic Acids that are identified from a Candidate Mixture of Nucleic Acids, said Nucleic Acid Ligand being a ligand of a given Target by the method comprising: a) contacting the Candidate Mixture with the Target, wherein Nucleic Acids having an increased affinity to the Target relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process. "Nucleic Acid" means both DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX™" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. In the present invention, the SELEX methodology is employed to obtain Nucleic Acid Ligands to C1q, C3 and C5. The SELEX methodology is described in the SELEX Patent Applications.

"Target" means any compound or molecule of interest for which a ligand is desired. A Target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the Target is a Complement System Protein, preferably C1q, C3 and C5.

"Complement System Protein" means any protein or component of the Complement System including, but not limited to, C1, C1q, C1r, C1s, C2, C3, C3a, C3b, C4, C4a, C5, C5a, C5b, C6, C7, C8, C9, Factor B (B), Factor D (D), Factor H (H) and receptors thereof, and other soluble and membrane inhibitors/control proteins.

"Complement System" is a set of plasma and membrane proteins that act together in a regulated cascade system to attack extracellular forms of pathogens or infected or transformed cells, and in clearance of immune reactants or cellular debris. The Complement System can be activated spontaneously on certain pathogens or by antibody binding to the pathogen. The pathogen becomes coated with Complement System Proteins (opsonized) for uptake and destruction. The pathogen can also be directly lysed and killed. Similar mechanisms target infected, transformed or damaged cells. The Complement System also participates in clearance of immune and cellular debris.

The SELEX process is described in U.S. patent application Ser. No. 07/536,428, filed Jun. 11, 1990, entitled "Systematic Evolution of Ligands by EXponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods for Identifying Nucleic Acid Ligands," now U.S. Pat. No. 5,270,163 (see also WO 91/19813). These applications, each specifically incorporated herein by reference, are collectively called the SELEX Patent Applications.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-Target pairs between the Target and those Nucleic Acids having the strongest affinity for the Target.

3) The Nucleic Acids with the highest affinity for the Target are partitioned from those Nucleic Acids with lesser affinity to the Target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5-50%) are retained during partitioning.

4) Those Nucleic Acids selected during partitioning as having the relatively higher affinity to the Target are then amplified to create a new Candidate Mixture that is enriched in Nucleic Acids having a relatively higher affinity for the Target.

5) By repeating the partitioning and amplifying steps above, the newly formed Candidate Mixture contains fewer and fewer weakly binding sequences, and the average degree of affinity of the Nucleic Acids to the Target will generally increase. Taken to its extreme, the SELEX process will yield a Candidate Mixture containing one or a small number of unique Nucleic Acids representing those Nucleic Acids from the original Candidate Mixture having the highest affinity to the Target molecule.

The SELEX Patent Applications describe and elaborate on this process in great detail. Included are Targets that can be used in the process; methods for partitioning Nucleic Acids within a Candidate Mixture; and methods for amplifying partitioned Nucleic Acids to generate enriched Candidate Mixture. The SELEX Patent Applications also describe ligands obtained to a number of target species, including both protein Targets where the protein is and is not a Nucleic Acid binding protein.

The SELEX method further encompasses combining selected Nucleic Acid Ligands with lipophilic or Non-Immunogenic, High Molecular Weight compounds in a diagnostic or therapeutic complex as described in U.S. patent application Ser. No. 08/434,465, filed May 4, 1995, entitled "Nucleic Acid Ligand Complexes," now U.S. Pat. No. 6,011,020. VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228. VEGF Nucleic Acid Ligands that are associated with a Lipophilic Compound, such as a glycerol lipid, or a Non-Immunogenic, High Molecular Weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes," now U.S. Pat. No. 6,051,698. VEGF Nucleic Acid Ligands that are associated with a Non-Immunogenic, High Molecular Weight compound or a lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

Certain embodiments of the present invention provide a complex comprising one or more Nucleic Acid Ligands to a Complement System Protein covalently linked with a Non-Immunogenic, High Molecular Weight compound or lipophilic compound. A complex as used herein describes the molecular entity formed by the covalent linking of the Nucleic Acid Ligand of a Complement System Protein to a Non-Immunogenic, High Molecular Weight compound. A Non-Immunogenic, High Molecular Weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the Non-Immunogenic, High Molecular Weight compound is a polyalkylene glycol. In the most preferred embodiment, the polyalkylene glycol is polyethylene glycol (PEG). More preferably, the PEG has a molecular weight of about 10-80K. Most preferably, the PEG has a molecular weight of about 20-45K. In certain embodiments of the invention, the Non-Immunogenic, High Molecular Weight compound can also be a Nucleic Acid Ligand.

Another embodiment of the invention is directed to complexes comprised of a Nucleic Acid Ligand to a Complement System Protein and a lipophilic compound. Lipophilic compounds are compounds that have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipids (and/or other materials or phases with low dielectric constants). Cholesterol, phospholipid, and glycerol lipids, such as dialkyl glycerol, diacyl glycerol, and glycerol amide lipids are further examples of lipophilic compounds. In a preferred embodiment, the lipophilic compound is a glycerol lipid.

The Non-Immunogenic, High Molecular Weight compound or lipophilic compound may be covalently bound to a variety of positions on the Nucleic Acid Ligand to a Complement System Protein, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the Nucleic Acid Ligand to a Complement System Protein. In embodiments where the lipophilic compound is a glycerol lipid, or the Non-Immunogenic, High Molecular Weight compound is polyalkylene glycol or polyethylene glycol, preferably the Non-Immunogenic, High Molecular Weight compound is bonded to the 5' or 3' hydroxyl of the phosphate group thereof. In the most preferred embodiment, the lipophilic compound or Non-Immunogenic, High Molecular Weight compound is bonded to the 5' hydroxyl of the phosphate group of the Nucleic Acid Ligand. Attachment of the Non-Immunogenic, High Molecular Weight compound or lipophilic compound to the Nucleic Acid Ligand of the Complement System Protein can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be referred to as a spacer.

The complex comprising a Nucleic Acid Ligand to a Complement System Protein and a Non-Immunogenic, High Molecular Weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In a preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The methods described herein and the Nucleic Acid Ligands identified by such methods are useful for both therapeutic and diagnostic purposes. Therapeutic uses include the treatment or prevention of diseases or medical conditions in human patients, specifically diseases or conditions caused by activation of the Complement System. The Complement System does not have to be the only cause of the disease state, but it may be one of several factors, each of which contributes to pathogenesis. Such diseases or conditions include, but are not limited to, renal diseases, such as lupus nephritis and membranoproliferative glomerulonephritis (MPGN), membranous nephritis, IgA nephropathy; rheumatological diseases, such as rheumatoid arthritis, systemic lupus erythematosus (SLE), Behcet's syndrome, juvenile rheumatoid arthritis, Sjogren's syndrome and systemic sclerosis; neurological diseases, such as myasthenia gravis, multiple sclerosis, cerebral lupus, Guillain-Barre syndrome and Alzheimer's disease; dermatological diseases, such as Pemphigus/pemphigoid, phototoxic reactions, vasculitis and thermal burns; hematological diseases, such as paroxysmal nocturnal hemoglobinuria (PNH), hereditary erythroblastic multinuclearity with positive acidified serum lysis test (HEMPAS) and idiopathic thrombocytopenic purpura (ITP); biocompatibility/shock diseases, such as post-bypass syndrome, adult respiratory distress syndrome (ARDS), catheter reactions, anaphylaxis, transplant rejection, pre-eclampsia, hemodialysis and platelet storage; vascular/pulmonary diseases, such as atherosclerosis, myocardial infarction, stroke and reperfusion injury; allergies, such as anaphylaxis, asthma and skin reactions; infection, such as septic shock, viral infection and bacterial infection; and other conditions, such as atheroma, bowel inflammation, thyroiditis, infertility, paroxysmal nocturnal hemoglobinuria (PNH) and hemolytic anemia.

The Complement System can be inhibited at several points in the activation cascade by targeting different components. Inhibition of C1q would block the initiation by either antibody or non-antibody mechanisms. Antibodies activate C1q in many diseases including SLE, myasthenia gravis and arthritis. Non-antibody Complement System activation occurs in many diseases including Alzheimer's disease, myocardial infarction and septic shock. Blocking C1q could prevent the complement-mediated tissue injury in these diseases.

The Complement can also be activated in the absence of antibodies directly at the C3 stage. Activating surfaces including bacteria, virus particles or damaged cells can trigger Complement System activation that does not require C1q. An inhibitor of C3 could prevent Complement System activation and damage in these situations.

In other instances the inhibition of C5 is most useful. Activation of the Complement System by either C1q or C3 mechanisms both lead to activation of C5, so that inhibition of C5 could prevent Complement System-mediated damage by either pathway. However, both C1q and C3 are important in normal defense against microorganisms and in clearance of immune components and damaged tissue, while C5 is mostly dispensable for this function. Therefore, C5 can be inhibited either for a short term or a long term and the protective role of Complement System would not be compromised, whereas long term inhibition of C1q or C3 is not desirable. Finally, the C5 fragments C5a and C5b directly cause the majority of tissue injury and disease associated with unwanted Complement System activation. Therefore, inhibition of C5 is the most direct way of producing therapeutic benefit.

In other instances, the activation of the Complement System is desirable in the treatment or prevention of diseases or medical conditions in human patients. For example, the activation of the Complement System is desirable in treating bacterial or viral infections and malignancies. In addition, the activation of the Complement System on T-cells prior to transplantation could prevent rejection of an organ or tissue by eliminating the T-cells that mediate the rejection.

Furthermore, Nucleic Acid Ligands that bind to cell surface Targets could be made more efficient by giving them the ability to activate the Complement System. Nucleic Acid binding would then both inhibit a Target function and also eliminate the cell, for example, by membrane attack complex lysis and cell clearance through opsonization. Nucleic Acid Ligands could activate the Complement System through either the classical or the alternative pathways. C1q Nucleic Acid Ligands can be conjugated to other structures that target a cell surface component. For example, C1q Nucleic Acid Ligands can be conjugated to antibodies to cell targets, cytokines, growth factors or a ligand to a cell receptor. This would allow the C1q Nucleic Acid Ligands to multimerize on the targeted cell surface and activate the Complement System, thereby killing the cell.

The prototype classical pathway activators are immune aggregates, which activate the Complement System through binding to globular head groups on the C1q component. Generally, binding of two or more Fc domains to C1q is required; pentameric IgM is an especially efficient activator. In contrast, Nucleic Acid Ligands can activate through binding at a separate site on the C1q collagen-like tail region. This site also binds to a variety of other non-antibody activators including C-reactive protein, serum amyloid protein, endotoxin, β-amyloid peptide 1-40 and mitochondrial membranes. As with immunoglobulin, these non-antibody activators need to be multimerized to activate.

Nucleic Acid Ligands that bind to sites on the collagen-like region of C1q may also become activators when aggregated. Such a Complement System-activating aggregate may be lytic if formed on a cell surface, such as binding to a tumor-specific antigen (TSA) or to a leukocyte antigen. The extent of Nucleic Acid Ligand-mediated activation increases with the extent of Nucleic Acid Ligand aggregation (i.e., multiplicity of Nucleic Acid Ligand-C1q interaction). The Complement System-mediated killing is especially specific if the Nucleic Acid Ligands circulate as monomers which do not activate, but become activators when they are multimerized on the targeted cell surface.

As with any Complement System activation, the extent and specificity is determined by the amount of C3 deposited onto the targeted cell. Deposited C3 forms an enzyme convertase that cleaves C5 and initiates membrane attack complex formation. C3 is also the classical serum opsonin for targeting phagocytic ingestion. The prototype alternative pathway activators are repeating carbohydrate units including bacterial and yeast cell walls, fucoidin and Sepharose, or glycolipids such as endotoxin or the glycocalyx. Nucleic Acid Ligands could activate the alternative pathway by aggregating the C3 component on the cell surface. Depositing C3 on a cell promotes Factor B binding and alternative pathway C3 convertase formation. Binding of a Nucleic Acid Ligand to C3 blocks binding of the inhibitor Factor H and prevents C3b decay. This would also increase C3 convertase formation and alternative path activation. Nucleic Acid Ligands to C3 may have this activity since heparin binds activated C3 and can promote alternative pathway activation. Binding of Nucleic Acid Ligands to C3 blocks binding to C3 of the membrane-associated inhibitors CR1, CR2, MCP and DAF, preventing C3b convertase decay and stimulating alternative pathway activation. This alternative pathway mechanism can be as efficient as C1q-dependent activation in cell killing and lysis.

Nucleic Acid Ligand-mediated Complement System cell killing could be employed in several ways, for example, by: a) direct killing of tumor cells; b) lysis of targeted microorganisms or infected cells; and c) elimination of lymphocytes or lymphocyte subsets. Nucleic Acid Ligands could replace antibodies currently used for these purposes.

Diagnostic utilization may include either in vivo or in vitro diagnostic applications. The SELEX method generally, and the specific adaptations of the SELEX method taught and claimed herein specifically, are particularly suited for diagnostic applications. The SELEX method identifies Nucleic Acid Ligands that are able to bind targets with high affinity and with surprising specificity. These characteristics are, of course, the desired properties one skilled in the art would seek in a diagnostic ligand.

The Nucleic Acid Ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any Nucleic Acid Ligand by procedures known in the art to incorporate a labeling tag in order to track the presence of such ligand. Such a tag could be used in a number of diagnostic procedures. The Nucleic Acid Ligands to C1q, C3 and C5 described herein may specifically be used for identification of the C1q, C3 or C5 protein.

The SELEX process provides high affinity ligands of a target molecule. This represents a singular achievement that is unprecedented in the field of Nucleic Acids research. The present invention applies the SELEX procedure to the specific target C1q, which is part of the first component (C1) of the classical pathway of Complement System activation, to the specific target C3, which is part of both the classical and alternative pathway, and to the specific target C5, which is part of the terminal pathway. In the Example section below, the experimental parameters used to isolate and identify the Nucleic Acid Ligands to C1q, C3 and C5 are described.

In order to produce Nucleic Acids desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand have the highest possible affinity to the Target.

Pharmaceutical agents, which include, but are not limited to, small molecules, antisense oligonucleotides, nucleosides, and polypeptides can activate the Complement System in an undesirable manner. Nucleic Acid Ligands to Complement System Proteins could be used as a prophylactic by transiently inhibiting the Complement System, so that a pharmaceutical agent could be administered and achieve a therapeutically effective amount without eliciting the undesirable side effect of activating the Complement System.

In co-pending and commonly assigned U.S. patent application Ser. No. 07/964,624, filed Oct. 21, 1992, now U.S. Pat. No. 5,496,938, (the '938 Patent), methods are described for obtaining improved Nucleic Acid Ligands after SELEX has been performed. The '938 Patent, entitled "Nucleic Acid Ligands to HIV-RT and HIV-1 Rev," is specifically incorporated herein by reference in its entirety.

In the present invention, SELEX experiments were performed in order to identify RNA with specific high affinity for C1q, C3 and C5 from a degenerate library containing 30 or 50 random positions (30N or 50N). This invention includes the specific RNA ligands to C1q shown in Table 2 (SEQ ID NOS:5-20) and Table 6 (SEQ ID NOS:84-155), identified by the method described in Examples 2 and 6, the specific RNA ligands to C3 shown in Table 3 (SEQ ID NOS:21-46), identified by method described in Example 3, and the specific RNA ligands to C5 shown in Table 4 (SEQ ID NOS:47-74), Table 5 (SEQ ID NOS:76-83), Table 8 (SEQ ID NOS:75, 160-162), Table 10 (SEQ ID NOS:163-189), Table 12 (SEQ ID NOS:190-192), Table 13 (SEQ ID NOS:194-196) and FIGS. 5A-B (SEQ ID NOS:160 and 193) identified by methods described in Examples 4, 9, 10 and 1. This invention further includes RNA ligands to C1q, C3 and C5 which inhibit the function of C1q, C3 and C5. The scope of the ligands covered by this invention extends to all Nucleic Acid Ligands of C1q, C3 and C5, modified and unmodified, identified according to the SELEX procedure. More specifically, this invention includes Nucleic Acid sequences that are substantially homologous to the ligands shown in Tables 2-6, 8, 10 and 12-13 and FIGS. 5A-B (SEQ ID NOS:5-155 and 160-196). By substantially homologous, it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of C1q shown in Table 2 (SEQ ID NOS:5-20) and Table 6 (SEQ ID NOS:84-155) shows that sequences with little or no primary homology may have substantially the same ability to bind C1q. Similarly, a review of the sequence homologies of the ligands of C3 shown in Table 3 (SEQ ID NOS:21-46) shows that sequences with little or no primary homology may have substantially the same ability to bind C3. Similarly, a review of the sequence homologies of the ligands of C5 shown in Table 4 (SEQ ID NOS:47-74), Table 5 (SEQ ID NOS:76-83), Table 8 (SEQ ID NOS:75, 160-162), Table 10 (SEQ ID NOS:163-189), Table 12 (SEQ ID NOS:190-192), Table 13 (SEQ ID NOS:194-196) and FIGS. 5A-B (SEQ ID NOS:160 and 193) shows that sequences with little or no primary homology may have substantially the same ability to bind C5. For these reasons, this invention also includes Nucleic Acid Ligands that have substantially the same structure and ability to bind C1q as the Nucleic Acid Ligands shown in Table 2 (SEQ ID NOS:5-20) and Table 6 (SEQ ID NOS:84-155), Nucleic Acid Ligands that have substantially the same structure and ability to bind C3 as the Nucleic Acid Ligands shown in Table 3 (SEQ ID NOS:21-46) and Nucleic Acid Ligands that have substantially the same structure and ability to bind C5 as the Nucleic Acid Ligands shown in Table 4 (SEQ ID NOS:47-74), Table 5 (SEQ ID NOS:76-83), Table 8 (SEQ ID NOS:75, 160-162), Table 10 (SEQ ID NOS:163-189), Table 12 (SEQ ID NOS: 190-192), Table 13 (SEQ ID NOS:194-196) and FIGS. 5A-B (SEQ ID NOS:160 and 193). Substantially the same ability to bind C1q, C3 or C5 means that the affinity is within one or two orders of magnitude of the affinity of the ligands described herein. It is well within the skill of those of ordinary skill in the art to determine whether a given sequence—substantially homologous to those specifically described herein—has substantially the same ability to bind C1q, C3 or C5.

The invention also includes Nucleic Acid Ligands that have substantially the same postulated structure or structural motifs. Substantially the same structure or structural motifs can be postulated by sequence alignment using the Zukerfold program (see Zucker (1989) Science 244:48-52). As would be known in the art, other computer programs can be used for predicting secondary structure and structural motifs. Substantially the same structure or structural motif of Nucleic Acid Ligands in solution or as a bound structure can also be postulated using NMR or other techniques as would be known in the art.

One potential problem encountered in the therapeutic, prophylactic and in vivo diagnostic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the Nucleic Acid Ligand can be made to increase the in vivo stability of the Nucleic Acid Ligand or to enhance or to mediate the delivery of the Nucleic Acid Ligand. See, e.g., U.S. patent application Ser. No. 08/117,991, filed Sep. 8, 1993, entitled "High Affinity Nucleic Acid Ligands Containing Modified Nucleotides," now abandoned (see also U.S. Pat. No. 5,660,985) and U.S. patent application Ser. No. 08/434,465, filed May 4, 1995, entitled "Nucleic Acid Ligand Complexes," which are specifically incorporated herein by reference in their entirety. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield Nucleic Acid Ligands with both specificity for their SELEX Target and improved in vivo stability. Post-SELEX modifications made to 2'-OH Nucleic Acid Ligands can result in improved in vivo stability without adversely affecting the binding capacity of the Nucleic Acid Ligand. The preferred modifications of the Nucleic Acid Ligands of the subject invention are 5' and 3' phosphorothioate capping and/or 3'-3' inverted phosphodiester linkage at the 3' end. In one preferred embodiment, the preferred modification of the Nucleic Acid Ligand is a 3'-3' inverted phosphodiester linkage at the 3' end. Additional 2'-fluoro (2'-F) and/or 2'-amino (2'-NH$_2$) and/or 2'-O-methyl (2'-OMe) modification of some or all of the nucleotides is preferred. Described herein are Nucleic Acid Ligands that were 2'-NH$_2$ modified or 2'-F modified and incorporated into the SELEX process. Further described herein are 2'-F modified Nucleic Acid Ligands derived from the SELEX process which were modified to comprise 2'-OMe purines in post-SELEX modifications.

Other modifications are known to one of ordinary skill in the art. Such modifications may be made post-SELEX (modification of previously identified unmodified ligands) or by incorporation into the SELEX process.

As described above, because of their ability to selectively bind C1q, C3 and C5, the Nucleic Acid Ligands to C1q, C3 and C5 described herein are useful as pharmaceuticals. This invention, therefore, also includes a method for treating Complement System-mediated diseases by administration of a Nucleic Acid Ligand capable of binding to a Complement System Protein or homologous proteins. Certain diseases or conditions such as Alzheimer's disease or myocardial infarction activate C1q through the collagen-like region. In Alzheimer's disease, β-amyloid activates C1q. Structures in heart muscle that are exposed during myocardial infarction such as intermediate filaments, mitochondrial membranes or actin activate C1q. Nucleic Acid Ligands to C3 or to C5 could also inhibit Complement System activation in Alzheimer's disease or myocardial infarction, whether the Complement System is activated through C1q by antibody or non-antibody mechanisms, or independent of C1q through the alternative pathway. Thus, the Nucleic Acid Ligands of the present invention may be useful in treating Alzheimer's disease or myocardial infarction.

Therapeutic compositions of the Nucleic Acid Ligands may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and the Nucleic Acid Ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing Nucleic Acid Ligands for systemic delivery may be via subcutaneous, intramuscular, intravenous, intranasal or vaginal or rectal suppository.

The following Examples are provided to explain and illustrate the present invention and are not intended to be limiting of the invention. These Examples describe the use of SELEX methodology to identify high affinity RNA ligands to C1q, C3 and C5. Example 1 describes the various materials and experimental procedures used in Examples 2, 3, 4 and 6. Example 2 describes the generation of 2'-NH$_2$ RNA ligands to C1q. Example 3 describes the generation of 2'-F Nucleic Acid Ligands of Complement System Protein C3. Example 4 describes the generation of 2'-F Nucleic Acid Ligands of Complement System Protein C5. Example 5 describes the activation of the Complement System through C1q ligands. Example 6 describes the generation of 2'-F RNA ligands to C1q. Example 7 describes an assay for hemolytic inhibition for 2'-F RNA ligands to C5. Example 8 describes an assay for inhibition of C5a release by a Nucleic Acid Ligand (clone C6) to Human C5. Example 9 describes boundary experiments performed to determine the minimum binding sequence for Nucleic Acid Ligands to Human C5. Example 10 describes a Biased SELEX experiment performed to improve Nucleic Acid Ligand affinity, using a 42mer truncated sequence of clone C6 as the random sequence in the template. Example 11 describes the results of 2'-OMe purine substitutions in a Human C5 Nucleic Acid Ligand in an interference assay. Example 12 describes the structure of a 38mer truncate of a Nucleic Acid Ligand to human C5. Example 13 describes a hemolytic assay of 2'-OMe purine substituted Nucleic Acid Ligands to human C5.

EXAMPLE 1

Experimental Procedures

This example provides general procedures followed and incorporated in Examples 2, 3, 4 and 6 for the identification of 2'-NH$_2$ and 2'-F RNA ligands to C1q, and 2'-F ligands to C3 and C5.

A. Biochemicals

C1q, C3, C5 and C4-deficient guinea pig sera were obtained from Quidel (San Diego, Calif.). Bovine serum albumin (BSA), rabbit anti-BSA, CRP, SAP and β-amyloid peptides 1-40 and 1-42 were obtained from Sigma (St. Louis, Mo.). Nucleotides GTP, ATP and deoxynucleotides were obtained from Pharmacia (Uppsala, Sweden). Taq polymerase was obtained from Perkin-Elmer (Norwalk, Conn.). Modified nucleotides 2'-NH$_2$-CTP and 2'-NH$_2$-UTP, and 2'-F-CTP and 2'-F-UTP, were prepared as described in Jellinek et al. (1995) Biochem. 34:11363. Avian reverse transcriptase was obtained from Life Sciences (St. Petersburg, Fla.) and T7 RNA polymerase from USB (Cleveland, Ohio). Nitrocellulose filters were obtained from Millipore (Bedford, Mass.). All chemicals were the highest grade available.

B. RNA SELEX Procedures

The SELEX procedure has been described in detail in the SELEX Patent Applications (see also Jellinek et al. (1995) Biochem. 34:11363; Jellinek et al. (1994) Biochem. 33: 10450). Briefly, a DNA template was synthesized with a 5' fixed region containing the T7 promoter, followed by a 30N or a 50N stretch of random sequence, and then with a 3'-fixed region (Table 1; SEQ ID NOS:1 and 156). For the initial round of the SELEX process, 1 nmole (~$10^{14}$ unique sequences) of RNA (Table 1; SEQ ID NOS:2 and 157) was in vitro transcribed by T7 polymerase (Milligan et al. (1987) Nucleic Acids Res. 12:785) using mixed GTP/ATP and 2'-NH$_2$-CTP/UTP or 2'-F-CTP/UTP nucleotides, and with the addition of α-[$^{32}$P]-ATP. For this and subsequent rounds of the SELEX process, the RNA was purified by electrophoresis on 8% acrylamide gels with 7 M urea, 10 mM Tris-Borate, 2 mM EDTA, pH 8.3 running buffer. After autoradiography, the band containing labeled, modified RNA transcript was excised and frozen at −70° C., then 400 μL of 100 mM NaCl, 2 mM EDTA was added, the gel was mashed, and the slurry was spun through 2 cm of glass-wool (Rnase-free—Alltech Associates, Deerfield, Ill.) and two nitrocellulose filters. The RNA was precipitated by addition of 1/5 vol of 6.6 M NH$_4$OAc, pH 7.7, plus 2 vol of ethanol. The pellet was washed twice with 80% ethanol, and taken to dryness. The dry RNA pellet was dissolved in phosphate buffered saline (Sambrook et al. (1989) *Molecular Cloning. A laboratory Manual*. Cold Spring Harbor Laboratory, Cold Spring Harbor, N.Y.) containing 1 mM MgCl$_2$ (MgPBS).

For each round of the SELEX process, the RNA was incubated with C1q, C3 or C5 in MgPBS for 10 minutes at 37° C. Then the sample was filtered through a 43 mm nitrocellulose filter, and the filter was washed with 10 mL of MgPBS. For some rounds, the diluted RNA was pre-soaked with nitrocellulose filters overnight to reduce background. Four samples were run in parallel for most rounds with lesser amounts (chosen to be in suitable range to measure binding) of both RNA and C1q, C3 or C5 to measure binding $K_d$ for each sample. In addition, at each round, a sample of RNA was filtered without protein to determine background.

Filters were air-dried, sliced into strips, counted, and then extracted for 60 minutes at 37° C. with 400 μL of 1% SDS, 0.5 mg/mL Proteinase K (Boehringer Mannheim, Indianapolis, Ind.), 1.5 mM DTT, 10 mM EDTA, 0.1 M Tris, pH 7.5, with addition of 40 μg tRNA carrier. The aqueous RNA was extracted with phenol, phenol/chloroform (1: 1), and chloroform and then precipitated following addition of NH$_4$OAc/EtOH as above. The RNA was reverse transcribed in a volume of 50 μL for between 1 hour and overnight. The DNA was PCR amplified with specific primers (Table 1; SEQ ID NOS: 3-4) in a volume of 500 μL for 12-14 cycles, and then phenol/chloroform extracted and NaOAc/EtOH precipitated. The DNA pellet was taken up in H$_2$O, and an aliquot was T7 transcribed for the next round of the SELEX process.

C. Cloning

DNA from the 12$^{th}$ or the 14$^{th}$ round was PCR amplified with primers which also contained a ligation site to facilitate cloning. The DNA was cloned into a pUC9 vector, and colonies were picked for overnight growth and plasmid minipreps (PERFECTprep, 5'-3', Boulder, Colo.). The purified plasmids were PCR amplified with original 3' and 5' primers (as above), and products were analyzed by agarose gel electrophoresis (Sambrook et al. (1989) *Molecular Cloning. A laboratory Manual*. Cold Spring Harbor Laboratory, Cold Spring Harbor, N.Y.). DNA was T7 transcribed with α-[$^{32}$P]-ATP to prepare radiolabeled RNA for binding analysis and without radiolabel to prepare RNA for inhibition studies.

D. Sequencing

Plasmids purified using the PERFECTprep kit were sequenced with ABI dRhodamine Terminator cycling kit (Perkin-Elmer). Samples were sequenced on the ABI Prism 377 DNA Sequencer.

E. Binding Assays

Individual cloned DNA was T7 transcribed with α-[$^{32}$P]-ATP and the full length [$^{32}$P]-2'-NH$_2$-RNA or 2'-F-RNA was gel-purified (as above). RNA was suspended at approximately 5,000 cpm per 30 μL sample (<10 pM), and aliquots were incubated with various concentrations of C1q, C3 or C5 in MgPBS for 10 minutes at 37° C. Samples were then filtered through nitrocellulose, the filters washed with buffer and dried under an infrared lamp, and counted with addition of scintillation fluid (Ecoscint A, National Diagnostics, Atlanta, Ga.). A background sample of RNA alone was run in parallel. To measure inhibition of ligand binding to C1q, the RNA Nucleic Acid Ligand plus C1q plus inhibitor (e.g., the A-chain residue 14-26 site, SAP, β-amyloid peptide, CRP) were incubated for 10 minutes at 37° C., and then filtered. Filters were washed and counted.

RNA ligand binding to C1q was also measured in the presence of immune-complexes, which would block the binding of ligands to C1q head-groups. Immune complexes (IC) were formed by mixing 620 μg BSA at equivalence with 1 mL of rabbit anti-BSA (Sigma, St. Louis, Mo.) plus PEG 8000 added to 1% final concentration, and then the samples were incubated overnight at 4° C. The IC were pelleted by microfugation at 12,000 rpm for 10 minutes, washed five times with PBS, and suspended in 1 mL of MgPBS. For measurement of C1q RNA clone binding to C1q-immune complexes (C1q-IC), 20 μL of the purified [$^{32}$P]-RNA plus 20 μL of the IC were mixed with 20 μL of C1q at various concentrations at between $10^{-11}$ and $10^{-7}$ M in MgPBS plus 1% Triton. Samples were incubated for 30 minutes at room temperature, microfuged, and the pellets and supernatants counted.

F. Hemolytic Assays

Complement System consumption was measured by C4 hemolytic assay as described (Gaither et al. (1974) J. Immunol. 113:574). All samples were diluted and the assay run in veronal-buffered saline containing calcium, magnesium and 1% gelatin (GVB$^{++}$-complement buffer). For measurement of C4 consumption by β-amyloid peptide consumption, the peptide was added at 250 μg/mL to a ⅛ dilution of whole human serum and then incubated for 60 minutes at 37° C. The sample was then diluted for assay of C4 hemolytic activity. For assay of inhibition of β-amyloid peptide mediated complement consumption by C1q 2'-NH$_2$-RNA clones, the C1q RNA Nucleic Acid Ligand was included in the initial β-amyloid peptide-whole human serum incubation mixture, and then C4 amounts assayed as above.

Complement System inhibition by C5 Nucleic Acid Ligands was measured using human serum and antibody-coated sheep red blood cells. The red blood cells were incubated with a 1:40 dilution of fresh human serum and with serial dilutions of C5 ligand for 30 minutes at 37° C. Dilutions of serum and ligand were made in complement buffer (see previous paragraph). After incubation the samples were then diluted with 4° C. buffer containing EDTA to stop the reaction, and the hemoglobin release was quantitated from the optical density at 412 nm.

EXAMPLE 2

2'-NH$_2$ RNA Ligands to C1q

A. RNA SELEX

The pool of random 50N7-2'-NH$_2$ RNA bound to C1q by nitrocellulose filter assay with a K$_d$ of 2.3 µM. For round 1 of the SELEX process, the C1q concentration was between 0.156-1.25 µM and the RNA concentration was 15 µM. Throughout the SELEX process, the RNA concentrations were maintained at approximately 10-fold greater than the concentration of C1q, which was reduced at each round with a final round 14 C1q concentration of 136 pM. Background binding of RNA to nitrocellulose filters remained low throughout the SELEX procedure, in part because RNA was pre-adsorbed with nitrocellulose filters. The binding of pool RNA to C1q improved at each round. The evolved round 14 pool 2'-NH$_2$ RNA bound C1q with a K$_d$=670 pM, yielding an overall improvement in binding K$_d$ of 3400-fold.

Bulk RNA was then cloned for sequence determination and evaluation of binding. Through comparison of binding at 0.1 and 0.5 nM C1q, individual clones were ranked, and clones with C1q binding above background were sequenced and are shown in Table 2 (SEQ ID NOS:5-20). Family 1 contained 12 of the 19 total sequences. Family 2 contained three sequences. Both Family 3 and Family 4 contained two sequences. Both Family 1 and Family 2 sequences contain G-rich regions and both have the repeated sequence motifs GGAG and GGUG. The identity and homology of Family I members is greatest in the 5' half, which is G-rich. The C-rich 3' half has only short stretches of sequence homology, and these are shown only with inclusion of large gap regions. Sequences from all families can be folded to give stem-loop structures with extensive Watson-Crick base-pairing. Full binding curves for the highest affinity ligands yielded a K$_d$ range from 290 pM to 3.9 nM; the high affinity ligands were found in all four sequence families. All of the binding curves were monophasic. The binding maximum is not 100% because of variable amounts of nucleic acid alterations taking place during purification. This is known because usually ligands can be bound to protein, extracted, and then re-bound, and give maximum binding approaching 100% (data not shown).

B. Competition

2'-NH$_2$ RNA ligands from different families interact with the same or overlapping sites on C1q, as shown by cross-competition. This site is on the collagen-like region, at or near the A-chain 14-26 residue site (Jiang et al. (1994) J. Immunol. 152:5050) as shown by two lines of evidence. First, C1q when bound to IC still binds the ligand #50 (SEQ ID NO:12); binding to immunoglobulin Fc would block the head region, but leave the collagen-like tail available, suggesting that nucleic acid ligands derived by the SELEX process are bound to the tail. Second, and more direct, ligand #50 is competed by proteins which are known to bind the A-chain residue 14-26 site, including SAP, β-amyloid peptide and CRP. Finally, ligand #50 is competed by a peptide that has the same amino acid sequence as residues 14-26 on the A-chain. This result is further supported by results for hemolytic inhibition as described below.

C. Consumption

Binding of a nucleic acid ligand derived by the SELEX process to the A-chain 14-26 amino acid site could activate C1q or alternatively, SELEX-derived nucleic acid ligands could inhibit the binding of other molecules and prevent C1q activation. This was tested by measuring C4 consumption in serum after incubation with a 2'-NH$_2$ SELEX-derived nucleic acid ligands, or after incubation with a known C1q activator together with a 2'-NH$_2$ nucleic acid ligand. The SELEX-derived nucleic acid ligands when incubated in serum do not consume C4, and thus are not C1q activators. Nor do these ligands at this concentration inhibit serum lysis of antibody-coated sheep erythrocytes, which would occur if ligands bound near the C1q head groups (data not shown). The ligands do inhibit C4 consumption by another C1q activator, the β-amyloid 1-40 peptide. This peptide is known to activate C1q through binding at the A-chain 14-26 residue site; therefore, this inhibition confirms that SELEX-derived nucleic acid ligands bind at this A-chain site. Control ligands from the SELEX process that did not bind C1q by nitrocellulose assay were also ineffective in blocking the β-amyloid 1-40 peptide C1q activation.

EXAMPLE 3

2'-Fluoro Nucleic Acid Ligands of Complement System Protein C3

In order to generate ligands to complement protein C3, a library of about 10$^{14}$ RNA was generated that contained 30 nucleotides of contiguous random sequence flanked by defined sequences. In this experiment, 30N random nucleotides of the initial Candidate Mixture were comprised of 2'-F pyrimidine bases. The rounds of selection and amplification were carried out as described in Example 1 using art-known techniques. In round 1 the 30N7-2'-F-RNA and C3 were both incubated at 3 µM. There was barely detectable binding at this round. Both the RNA and C3 concentrations were decreased during the SELEX procedure. Sequences derived from the SELEX procedure are shown in Table 3 (SEQ ID NOS:21-46).

EXAMPLE 4

2'-Fluoro Nucleic Acid Ligands of Complement System Protein C5

In order to generate ligands to human complement protein C5, a library of about 10$^{14}$ RNA was generated that contained 30 nucleotides of contiguous random sequence flanked by defined sequences. In this experiment, the 30N random nucleotides of the initial Candidate Mixture were comprised of 2'-F pyrimidine bases. Briefly, a DNA template was synthesized with a 5'-fixed region containing the T7 promoter, followed by a 30N stretch of random sequence, and then with a 3'-fixed region (Table 1; SEQ ID NO: 1). The rounds of selection and amplification were carried out as described in Example 1 using art-known techniques. The initial rounds of the SELEX experiment were set up with high concentrations of 2'-F RNA (7.5 µM) and protein (3 µM), as the binding of C5 to unselected RNA was quite low. The SELEX experiment was designed to promote binding of RNA at the C5a-C5b cleavage site. RNA and C5 were incubated together with small amounts of trypsin, with the reasoning that limited trypsin treatment of C5 produces a single site cleavage and generates C5a-like activity (Wetsel and Kolb (1983) J. Exp. Med. 157: 2029). This cleavage led to a slight increase in random RNA binding. Enhanced RNA binding associated structurally with exposure of the C5a-like domain could evolve Nucleic Acid Ligands that bind near the C5 convertase site and could interfere with or inhibit C5 cleavage. The SELEX experiment was performed simultaneously to both the native and to the mildly-trypsinized protein, so that Nucleic Acid Ligand evolution would pick the highest affinity winner. With this procedure the highest affinity winner against the multiple protein species would be evolved, and multiple aptamers and specific aptamers might be obtained out of a single SELEX experiment.

For each round of the SELEX process, the procedure was performed in parallel in separate tubes with approximately 5-fold excess of RNA either in buffer alone or with addition of trypsin at between 0.3 and 0.0001 mg/mL. Samples were incubated in MgPBS for 45 minutes at 37° C., and then filtered through nitrocellulose. The filters were washed, dried and counted, extracted, reverse-transcribed, then PCR amplified and finally T7 transcribed in vitro into RNA using mixed GTP/ATP and 2'-F-CTP/UTP nucleotides and $\alpha$-[$^{32}$P]-ATP. RNA was purified by electrophoresis in 8% acrylamide gels with 7M urea and Tris-Borate EDTA buffer (TBE). RNA was isolated and precipitated with NH$_4$OAc/ethanol, and then dissolved in phosphate-buffered saline containing 1 nM MgCl$_2$ (MgPBS). Filters with the highest binding were carried forward. At the end of each round, all of the RNA that bound to the protein (either with or without trypsin) was pooled. The protein and RNA concentrations at each round were reduced, with final concentrations of 2.5 nM and 10 nM respectively. Trypsin was added at concentrations between 0.3 and 0.0001 µg/mL. Background binding was monitored at each round, and starting at round four the transcribed RNA was presoaked overnight with nitrocellulose filters prior to the SELEX rounds to reduce background.

Based on binding of RNA to native C5 by nitrocellulose assay, round twelve DNA was cloned and sequences were obtained as shown in Table 4 (SEQ ID NOS:47-74). Sequences were grouped according to homology and function. Group I sequences are highly homologous and might have arisen by PCR mutation from a single original sequence. Binding affinities of the Group I Nucleic Acid Ligands are very similar and are shown in Table 7. Group II Nucleic Acid Ligands generally bound with similar affinity to Group I Nucleic Acid Ligands, although some weak binders were also present. Group II sequences and length are more diverse than Group I Nucleic Acid Ligands. The C5 Nucleic Acid Ligands do not bind other complement components including C1q, C3, or factors B, H, or D.

Nucleic Acid Ligands from each family were also assayed for inhibition of rat Complement System activity (Table 5; SEQ ID NOS:76-83). Nucleic Acid Ligands from Family I and Family III inhibited rat complement, whereas a Nucleic Acid Ligand from Family II did not. An inhibitory Nucleic Acid Ligand can be used to inhibit Complement System activity in various rat disease models including, but not limited to, myasthenia gravis, myocardial infarction, glomerulonephritis, ARDS, arthritis and transplantation.

EXAMPLE 5

Activation of the Complement System Through C1q Nucleic Acid Ligands

Oligonucleotides can activate both classical and alternative pathways. Particularly, poly-G oligonucleotides which can form G-quartet structures and can interact with the C1q collagen-like region are able to form high molecular weight aggregates, which both bind and activate C1q. Phosphorothioate oligonucleotides, which have increased non-specific binding as compared with phosphodiester oligonucleotides, are also efficient Complement System activators, particularly poly-G containing phosphorothioate oligonucleotides. Results for oligonucleotide activation of solution phase Complement are shown below where classical pathway activation is measure by the release of C4d fragment by ELISA (Quidel, San Diego, Calif.), and alternative pathway activation is measure by Bb ELISA (Quidel, San Diego, Calif.). Although these pathways are separate, there is evidence to suggest that oligonucleotide activation of both pathways is C1q dependent.

| Sample | | [C4d] µg (Class.) | [Bb] µg (Altern.) |
|---|---|---|---|
| Poly-AG | Random Co-Polymer | 8.1 | 18.9 |
| Poly-G | Random Co-Polymer | 1.2 | 29.3 |
| Poly-I | Random Co-Polymer | 0 | 14.7 |
| Poly-A | Random Co-Polymer | 0 | 0 |
| Poly-U | Random Co-Polymer | 0 | 1.8 |
| Poly-C | Random Co-Polymer | 0 | 2.5 |
| Phosphorothioate Oligonucleotides | | | |
| GGCGGGGCTACGTACCGGGGCTTTGTAAAACCCCGCC SEQ ID NO: 197 | | -7.1 | 32.4 |
| CTCTCGCACCCATCTCTCTCCTTCT SEQ ID NO: 198 | | 0.0 | 3.9 |
| BSA-anti-BSA | Immune Complexes | 8.0 | 11.9 |
| β-Amyloid Peptide | | 2.7 | n/d |
| Fucoidan | Sulfated Carbohydrate | | 27 |
| buffer | | 0.0 | 0.0 |

Complement System activation is also initiated on the erythrocyte membrane and is tested by hemolytic assays. Known activators, including 2'-OH poly-G and phosphorothioate oligonucleotides, as well as potential activators such as multimerized C1q Nucleic Acid Ligands and small (e.g., 15-mer) 2'-F poly-G oligonucleotides are coated on sheep erythrocytes and subsequent lysis of the erythrocytes by serum complement is measured. Methods of coating oligonucleotides and Nucleic Acid Ligands on cells include passive adsorption, chemical conjugation, streptavidin-biotin coupling and specific Nucleic Acid binding. Following treatment with fresh rat or human serum, the deposition of complement components on the cell, membrane damage and lysis are measured by standard methods as would be known by one of skill in the art.

A. Aggregation of C1q Nucleic Acid Ligands

C1q Nucleic Acid Ligands are dimerized using chemical cross-linkers of various lengths. Alternatively, Nucleic Acid Ligand monomers are biotinylated and then multimerized with streptavidin. Each of these multimers are tested for complement activation and lysis of erythrocytes.

The addition of poly-G sequence to C1q Nucleic Acid Ligands provides additional binding ability and increases the ability of the oligonucleotide to activate the Complement System. In addition, short poly-G sequences on individual C1q Nucleic Acid Ligands can interact to form higher order structures, which serve to multimerize the C1q Nucleic Acid Ligands and cause activation.

B. Lysis of Erythrocytes and Leukocytes

Nucleic Acid Ligands that promote erythrocyte lysis are tested on nucleated cells, including lymphocytes and tumor cells. Nucleated cells have mechanisms of complement resistance that erythrocytes lack. For example, nucleated cells can shed antigens, bleb off membrane vesicles containing the complement components and express increased levels of complement inhibitors as compared with erythrocytes and may up-regulate protective mechanisms upon initial complement attack. As high levels of activation are important for cell killing, activators are compared for amount of Complement System component deposition and extent of membrane damage. Also, different types and sources of tumor cells and lymphocytes are tested to determine if susceptibility is cell-type specific.

Nucleic Acid Ligands can be generated for virtually any target as described in the SELEX Patent Applications. Nucleic Acid Ligands to L-Selectin have been generated (See U.S. patent application Ser. No. 08/479,724, filed Jun. 7, 1995, entitled "High Affinity Nucleic Acid Ligands to Lectins," now U.S. Pat. No. 5,780,228, which is incorporated herein by reference in its entirety). The diversity of lectin mediated functions provides a vast array of potential therapeutic targets for lectin antagonists. For example, antagonists to the mammalian selecting, a family of endogenous carbohydrate binding lectins, may have therapeutic applications in a variety of leukocyte-mediated disease states. Inhibition of selectin binding to its receptor blocks cellular adhesion and consequently may be useful in treating inflammation, coagulation, transplant rejection, tumor metastasis, rheumatoid arthritis, reperfusion injury, stroke, myocardial infarction, bums, psoriasis, multiple sclerosis, bacterial sepsis, hypovolaemic and traumatic shock, acute lung injury and ARDS. The coupling of C1q Nucleic Acid Ligands to L-Selectin Nucleic Acid Ligands makes the L-Selectin Nucleic Acid Ligand more efficient by promoting cell killing at the target. C1q Nucleic Acid Ligands are coupled to L-Selectin Nucleic Acid Ligands, and the conjugates are tested for leukocyte lysis as described above. Also, Nucleic Acid Ligands to other cell surface targets, antibodies to all targets that do not themselves activate complement, cytokines, growth factors, or a ligand to a cell receptor could be coupled to a C1q Nucleic Acid Ligand and used for cell killing.

C. In Vivo Testing of Complement Activation

Nucleic Acid Ligand-mediated Complement System activation is tested in animals to evaluate in vivo Nucleic Acid Ligand action. Erythrocytes and/or lymphocytes are coated with Nucleic Acid Ligands and injected into rats to test cell killing and lysis in vivo. Activating Nucleic Acid Ligands are also coupled to a Mab that does not activate the Complement System, where the antibody is directed against a rat cell antigen (e.g., lymphocyte antigen). These cells are then coated with the Nucleic Acid Ligand-antibody conjugate and injected into rats. Alternatively, the Nucleic Acid Ligand-antibody conjugate is injected directly into the rat and then in vivo leukocyte killing is measured.

It is also possible that C1q Nucleic Acid Ligands cross-react with non-human C1q, and non-human C1q could be used for in vivo assays. C1q Nucleic Acid Ligands are tested against species such as mouse, rat and rabbit C1q. C1q is purified from serum and cross-reactivity with C1q Nucleic Acid Ligands is tested by nitrocellulose binding assay. Alternatively, C1q is bound to immune complexes which are added to serum and then C1q Nucleic Acid Ligand binding to the aggregate is tested. If Nucleic Acid Ligands are species-specific, then rat serum is depleted of rat C1q by continuous perfusion over a Ig-Sepharose column, and the serum is reconstituted with human C1q by methods known to one of skill in the art. These reconstituted animals are then used to test C1q Nucleic Acid Ligands for targeted Complement System activation and cell killing.

EXAMPLE 6

2'-Fluoro RNA Ligands of Complement System Protein C1q

A. RNA SELEX

The pool of random 30N7-2'-F RNA bound to C1q by nitrocellulose filter assay with a $K_d$ of 2.3 µM. For round 1 of the SELEX process, the C1q concentration was between 0.156-1.25 µM and the RNA concentration was 15 µM. Throughout the SELEX process, the RNA concentrations were maintained at approximately 10-fold greater than the concentration of C1q, which was reduced at each round with a final round 14 C1q concentration of 136 pM. Background binding of RNA to nitrocellulose filters remained low throughout the SELEX procedure, in part because RNA was pre-adsorbed with nitrocellulose filters. The binding of pool RNA to C1q improved at each round. The evolved round 14 pool 2'-F RNA bound C1q with a $K_d$ of 2 nM, yielding an overall improvement in binding $K_d$ of 1-3000 -fold.

Bulk RNA was then cloned for sequence determination and evaluation of binding. Through comparison of binding at 0.1 and 0.5 nM C1q, individual clones were ranked for binding affinity. Sequences of 2'-F RNA ligands are shown in Table 6 (SEQ ID NOS:84-155). The 2'-F-RNA sequences are not easily grouped into families, but these sequences are G-rich and are similar but not homologous with the 2'-NH$_2$ RNA sequences described in Example 2.

EXAMPLE 7

Hemolytic Inhibition for 2'-F RNA Ligands to C5

The 2'-F RNA Nucleic Acid Ligands to C5 (Example 4) were assayed for hemolytic inhibition by including dilutions in a standard assay for human serum lysis of antibody-coated sheep erythrocytes. Sheep cells were mixed with a 1:40 dilution of serum containing Nucleic Acid Ligand or buffer, and incubated for 30 minutes at 37° C. After quenching with cold EDTA buffer, the samples were spun and supernatants read at OD 412 nm. Group I Nucleic Acid Ligands inhibited almost to background at 1 µM, with a $K_i$ of 60-100 nM. The results are shown in FIG. 1. The results of the hemolysis inhibition assay suggested that 2'-F RNA Nucleic Acid Ligands to C5 target a specific site on C5, where they block interaction of C5 with the Complement C5 convertase. These results also confirmed that the 2'-F RNA Nucleic Acid Ligands are stable in serum.

EXAMPLE 8

Inhibition of C5a Release

Figure 2:
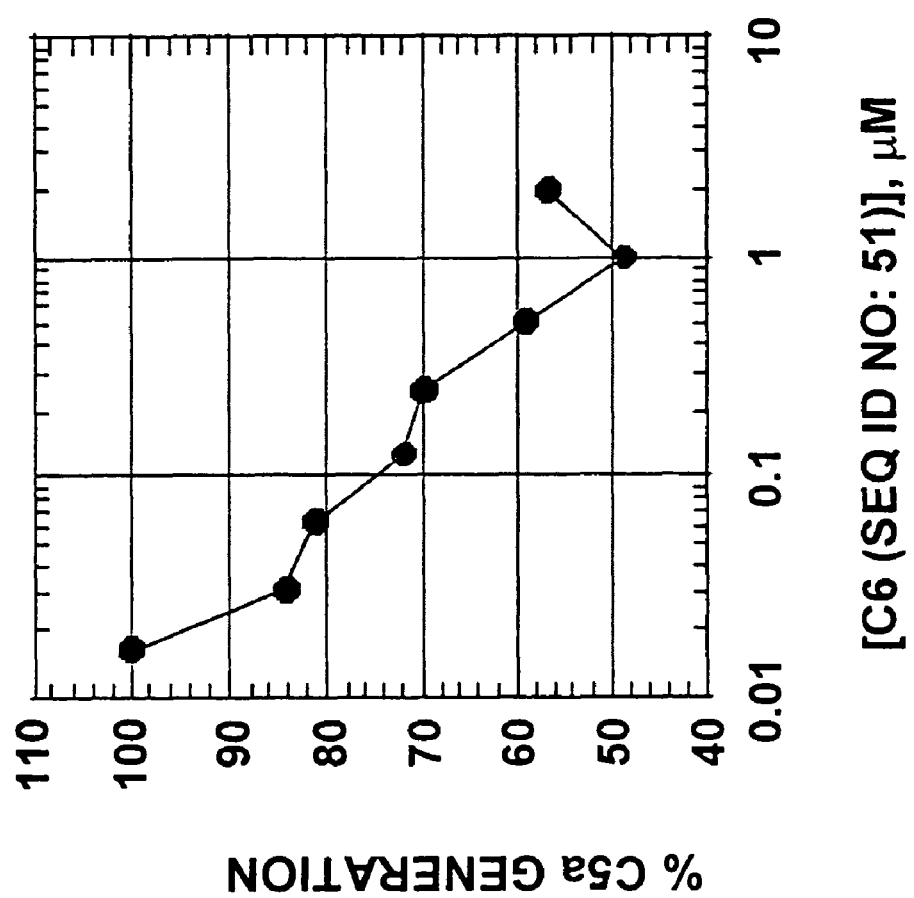
FIG. 2 shows the % C5a generation as a function of concentration of clone C6 (SEQ ID NO:51).

Nucleic Acid Ligand-C5 interaction that inhibits cleavage of C5 would prevent formation of the C5b and MAC assembly. Inhibition of C5 cleavage should also inhibit C5a release, and this was shown in the following experiment with clone C6 (SEQ ID NO:51) (Example 4). For this experiment, dilutions of clone C6 were incubated with whole human serum in GVB++ (veronal-buffered saline containing calcium, magnesium and 1% gelatin) plus addition of zymosan for 30 minutes at 37° C. The samples were then quenched with EDTA-buffer and spun, and supernatants were assayed for C5a by radioimmunoassay (RIA) (Wagner and Hugli (1984) Anal. Biochem. 136:75). The results showed that clone C6 inhibited C5a release with a $K_i$ of approximately 100 nM (FIG. 2), whereas control random pool RNA gave no inhibition (data not shown). This assay also demonstrated the serum stability of clone C6.

EXAMPLE 9

Boundaries of Clone C6

Clone C6 (SEQ ID NO:51) (Example 4) was selected for determination of a minimal binding sequence. This was done in the following two ways.

1) The minimal RNA sequences (5' and 3' boundaries) required for binding of clone C6 to C5 were determined by partially hydrolyzing clone C6 and determining protein binding (Green et al. (1995) Chem. Biol. 2:683). Briefly, clone C6 was synthesized as either 5'-[$^{32}$P]-kinase labeled (to determine the 3' boundary) or 3'-[$^{32}$P]-pCp labeled (to determine the 5' boundary) and the oligonucleotides were purified. Then the oligonucleotides were subjected to alkaline hydrolysis, which cleaves oligonucleotides from the 3' end to purine bases. The partially hydrolyzed RNA was then incubated with C5, and RNA which bound to the C5 protein was partitioned on nitrocellulose and eluted from the protein. The partitioned RNA together with an RNA ladder were run on an 8% acrylamide/7M urea sequencing gel. The boundary where removal of one more base would reduce or eliminate binding was determined by comparison of selected RNA (RNA which bound to C5) versus non-selected RNA (RNA which did not bind to C5).

Figure 3:
FIG. 3A shows a sequencing gel of 5'-kinase-labeled clone C6 (SEQ ID NO:51) after alkaline hydrolysis or digestion with $T_1$ nuclease. The 3'-sequence (5'-end labeled) is aligned with the alkaline hydrolysis ladder. On the left is the $T_1$ ladder and on the right are RNA selected with 5× and 1× concentrations of C5. The boundary where removal of a base eliminates binding is shown by the arrow. The asterisk shows a G which is hypersensitive to $T_1$.
FIG. 3B shows a sequencing gel of 3'-pCp-ligated clone C6 after alkaline hydrolysis or digestion with $T_1$ nuclease. The 5'-sequence (3'-end-labled) is aligned with the alkaline hydrolysis ladder. The $T_1$ and protein lanes, boundary and hypersensitive G nucleotides are as described for FIG. 3A.

The labeled RNA was also digested with $T_1$ nuclease (which cleaves oligonucleotides from the 3' end to A residues), incubated with C5 and partitioned as above, for a second ladder. FIG. 3A shows the results of the digestion of the 5'-kinase-labeled RNA. In this figure, the 3'-sequence (5'-end labeled) is aligned with the alkaline hydrolysis ladder. On the left is the $T_1$ ladder and on the right are RNA selected with 5× and 1× concentrations of C5. The boundary where removal of a base eliminates binding is shown by the arrow. The asterisk shows a G which is hypersensitive to $T_1$. Other G nucleotides in the minimal sequences are protected from $T_1$ digestion. FIG. 3B shows the results of the 3'-pCp-ligated RNA. In this figure, the 5'-sequence (3'-end-labled) is aligned with the alkaline hydrolysis ladder. The $T_1$ and protein lanes, boundary and hypersensitive G nucleotides are as described for FIG. 3A.

2) In a second experiment, the results obtained from the boundary experiments described above were used to construct synthetic truncated Nucleic Acid Ligands to C5. Several truncates between 34 and 42 nucleotides were synthesized by removing residues at both ends of clone C6 (SEQ ID NO:51), and assayed for C5 binding (Table 8). The shortest oligonucleotide which bound to C5 was a 38mer (SEQ ID NO:160), which confirms the boundary gel and which provides a preliminary structure for further Nucleic Acid Ligand development. In the minimal 38mer sequence, 30 bases originated from the random region and eight bases were from the 5' fixed region of clone C6. Removing a base from both 5' and 3' ends of the 38mer to produce a 36mer (SEQ ID NO:161) reduced the binding. A 34mer (SEQ ID NO:162) did not bind. Other truncated oligonucleotides with internal deletions also failed to bind.

EXAMPLE 10

Biased SELEX

A biased SELEX experiment was performed to improve Nucleic Acid Ligand affinity and to further define the structure. The sequence of the 42mer truncate (SEQ ID NO:75) from Example 9 (Table 8) was used as a template for the Biased SELEX experiment. A synthetic template comprising a 42N random region flanked by new n8 fixed regions (Table 10; SEQ ID NO:163) was constructed and synthesized (Oligos, Etc., CT), where the random region was biased toward the 42mer truncate of clone C6 from the first SELEX experiment. A 42mer random region was chosen rather than the minimal 38mer sequence, as the four extra bases extended a terminal helix. While not wishing to be bound by any theory, the inventors believed that although these four extra bases were not essential for binding, a longer helix was thought desirable to aid in selecting the Nucleic Acid Ligand structure and in minimizing the possible use of fixed regions in the newly selected Nucleic Acid Ligand structure. Each base in the random region was synthesized to contain 0.67 mole fraction of the base corresponding to the base in the 42mer sequence and 0.125 mole fraction of each of the other three bases. The Biased SELEX experiment was performed as described for the standard SELEX experiment in Example 1. PCR amplification was performed using primers shown in Table 1 (SEQ ID NOS:158-159).

The Biased SELEX experiment was performed with native C5 protein since clone C6 already inhibits hemolysis and trypsin treatment is not required for binding. The binding of the starting RNA pool to C5 was very low, so the protein and RNA concentrations were started at 2.6 μM and 7.1 μM, respectively, similar to the first SELEX experiment. The binding rapidly improved at round three. RNA and protein concentrations were gradually reduced at each subsequent round to final concentrations by round nine of 62.5 pM and 31 pM, respectively. The binding of the RNA pool to C5 was approximately 5 nM (Table 9), as compared to approximately 100 nM for the RNA pool from the first SELEX experiment. Some of the improvements in the affinity of the pool results from absence of lower affinity ligands, size mutants and background binders, which were not allowed to build up to appreciable concentrations during this more rapid SELEX experiment.

The RNA pool after eight rounds of the Biased SELEX process was improved by 20-50 fold over the round twelve pool from the first SELEX experiment. The overall improvement in $K_d$ from the random pool to pool from eight rounds of the Biased SELEX process is estimated to be greater than $10^5$-fold. The isolated and cloned sequences from the Biased SELEX experiment are shown in Table 10 (SEQ ID NOS: 164-189). In the sequences shown in Table 10, the two base-pair stem which is dispensable for binding is separated from the minimal 38mer sequence. These bases show no selective pressure except to maintain the stem. None of the sequences exactly match the original template sequence.

Clones from the Biased SELEX experiment were assayed and representative binding affinities are shown in Table 11. Most clones bound with a $K_d$ between 10 and 20 nM and are higher affinity binding ligands than the template (SEQ ID NO:163). One of the clones, YL-13 (SEQ ID NO:175), bound approximately five-fold higher affinity than other clones from the Biased SELEX experiment and approximately 10-fold higher affinity than clone C6 (SEQ ID NO:51). None of Nucleic Acid Ligand sequences exactly matched the sequence used for the template in the Biased SELEX experiment. Some bases substitutions are unique to this Biased SELEX experiment sequence set and might account for increased Nucleic Acid Ligand affinity.

EXAMPLE 11

2'-O-Methyl Substitution for Nuclease Protection

To further stabilize the Nucleic Acid Ligand, positions where 2'-OH-purine nucleotides could be substituted with nuclease-resistant 2'-O-methyl nucleosides were determined. An assay for simultaneously testing several positions for 2'-O-methyl interference was used following the method described in Green et al. (1995) Chem. Biol. 2:683.

In the 2'-O-methyl interference assay, three sets of oligonucleotides based on a 38mer truncate of sequence YL-13 (SEQ ID NO:175) from the Biased SELEX experiment were synthesized. These sets of sequences, indicated as M3010 (SEQ ID NO:190), M3020 (SEQ ID NO:191) and M3030 (SEQ ID NO:192) in Table 12 were synthesized on an automated RNA synthesizer in a manner wherein each of the nucleotides indicated by bold underline in Table 12 were synthesized 50% as a 2'-OH-nucleotide and 50% as a 2'-OMe-substituted nucleotide. This resulted in a mixture of $2^5$ or 32 different sequences for each of sets M3010, M3020 and M3030.

The partially substituted 2'-OMe oligonucleotides were 5'-[$^{32}$P]-kinase-labeled. The oligonucleotides were selected at 100 nM and 10 nM C5 and the binding to protein was greater than 10-fold over background filter binding. The oligonucleotides were eluted from the protein, alkaline hydrolyzed and then run on a 20% acrylamide/7 M urea/TBE sequencing gel. On adjacent tracks were run oligonucleotides not selected with C5. Band intensities were quantitated with on an InstantImager (Packard, Meriden, Conn.). When these oligonucleotides were separated on an acrylamide gel the mixed OH:OMe positions showed up at 50% intensity of a full 2'-OH position, because the 2'-OMe is resistant to hydrolysis. 2'-F pyrimidines are also resistant and do not show on the gel.

Figure 4:
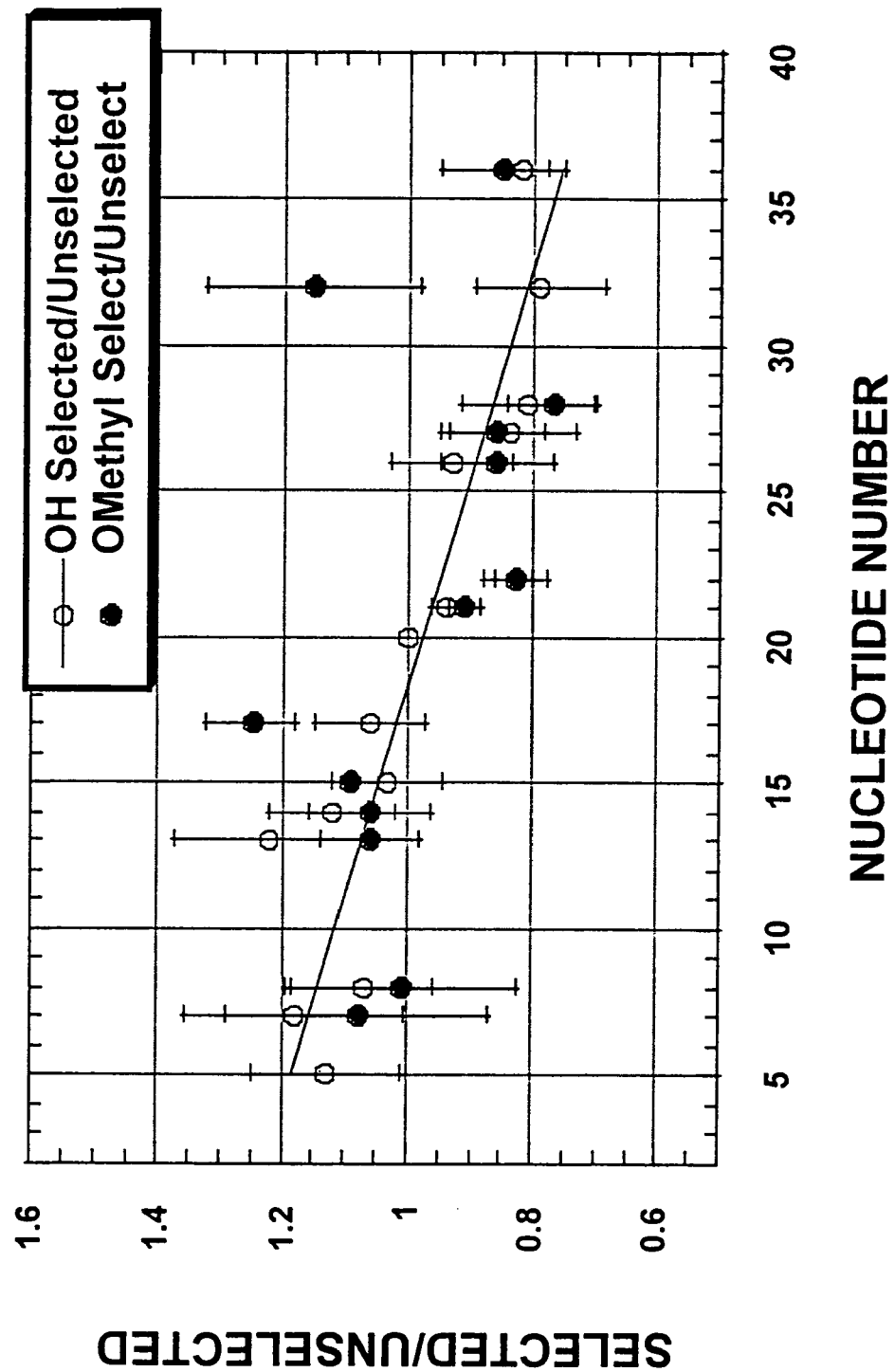
FIG. 4 shows the results of the 2'-O-methyl interference assay. Positions where 2'-OH purines can be substituted with 2'-O-methyl were determined from binding interference. Plotted is the ratio of (the intensity of bands selected by protein)/(the band intensity for oligonucleotides not selected by protein) with a linear curve fit (open circles). The same ratio for mixed 2'-OH:2'-OMe nucleotides is also plotted (closed circles).

For each position, the ratio of (the intensity of the bands selected by protein binding)/(band intensity for oligonucleotide not selected to protein) was calculated. These ratios were plotted versus nucleotide position and a linear fit determined (FIG. 4, open circles). The same calculation was made for mixed 2'-OH/2'-OMe oligonucleotides, and these ratios were compared with previously determined curve (FIG. 4, closed circles). Where 2'-OMe substitution did not interfere with binding the ratio was within one standard deviation of the 2'-OH ratio. However, where 2'-OMe substitution interfered with binding, the binding preference for 2'-OH purine increased the ratio. Two nucleotides at positions 16 and 32 were determined to require 2'-OH nucleotides. Separately, residue g5 was determined independently to require 2'-OH and residue G20 was determined to allow 2'-OMe substitution, and these were used to normalize lanes. These results were confirmed by synthesis and assay of 2'-OMe substituted oligonucleotides. The obligate 2'-OH positions are in one of two bulges, or in the loop in the putative folding structure, suggesting these features are involved in the protein interaction. Once the permissible 2'-OMe positions were determined, substituted oligonucleotides were synthesized and relative binding affinities were measured.

EXAMPLE 12

Human C5 Nucleic Acid Ligand Structure

Figure 5A:
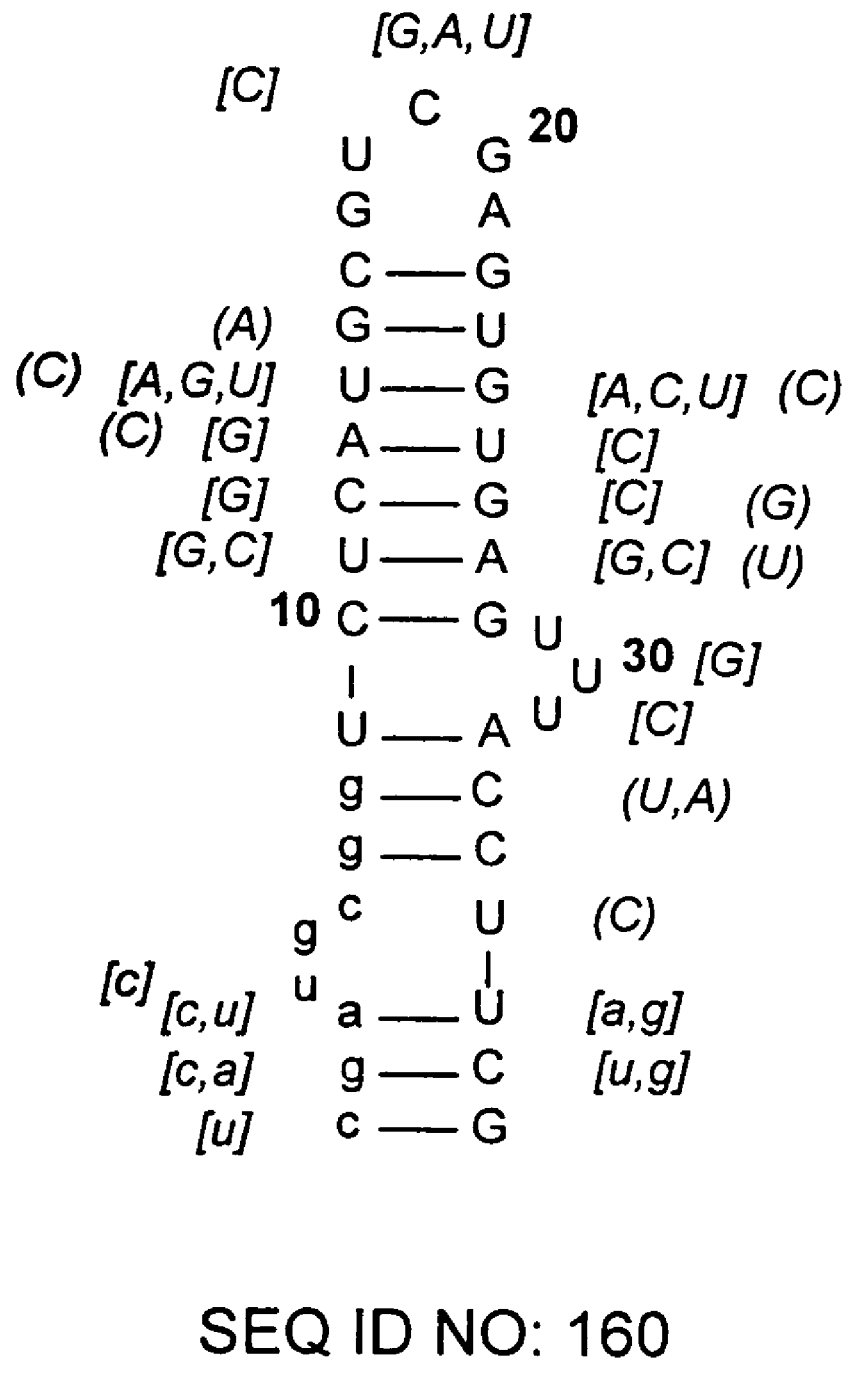

The putative folding and base-pairing, based on truncation experiments, nuclease sensitivity, base substitution patterns from the Biased SELEX experiment, and 2'-OMe substitutions, for the 38mer truncate of clone C6 together with alternative bases is shown in FIG. 5A. The basic sequences is the 38mer truncate (SEQ ID NO:160). In parentheses are variants from the first SELEX experiment. In brackets are variants from the Biased SELEX experiment. Lower case bases are derived from the 5'-n7 fixed region from the first SELEX experiment. Upper case bases are derived from the original random region.

The stem-loop structure has between 12 and 14 base-pairs: a) the proposed 5', 3'-terminal base pairs (c1-a3, and U36-G38); b) stem-loop base-pairs (U11-U14 and G24-A27) are supported by covariant changes during the Biased SELEX procedure; and c) the middle stem (g7-C10 and G28-C34), which is generally conserved, U9-A32 which is invariant and g8-C33 conserved during the Biased SELEX procedure. The u4→c4 change improves binding, and this change is found in all clones from the Biased SELEX experiment, and G29, A29 variants are found only in clones from the Biased SELEX experiment.

The UUU bulge is generally conserved. One original sequence contained two U bases, with no reduction in binding, and two Nucleic Acid Ligands with a single base substitution were found during Biased SELEX experiment. The C10-G28 base-pair following the UUU-bulge is conserved. This region with a conserved bulge and stem is likely involved in protein interaction. The stem-loop G15 to U23 is highly conserved, except for bases 19.

The 2'-OMe substitution pattern is consistent with this structure (SEQ ID NO:193; FIG. 5B). Positions where 2'-OMe substitutions can be made are shown in bold. The three positions which must be 2'-OH are shown as underlined. The obligate 2'-OH bases at g5, G17 and A32 are in bulge or loop regions which might form unique three-dimensional structures required for protein binding. Allowed positions for 2'-OMe substitution occur in stem regions where a standard helical structure is more likely.

EXAMPLE 13

Hemolytic Assay of 2'-OMe-Substituted Nucleic Acid Ligands to Human C5

Figure 6:
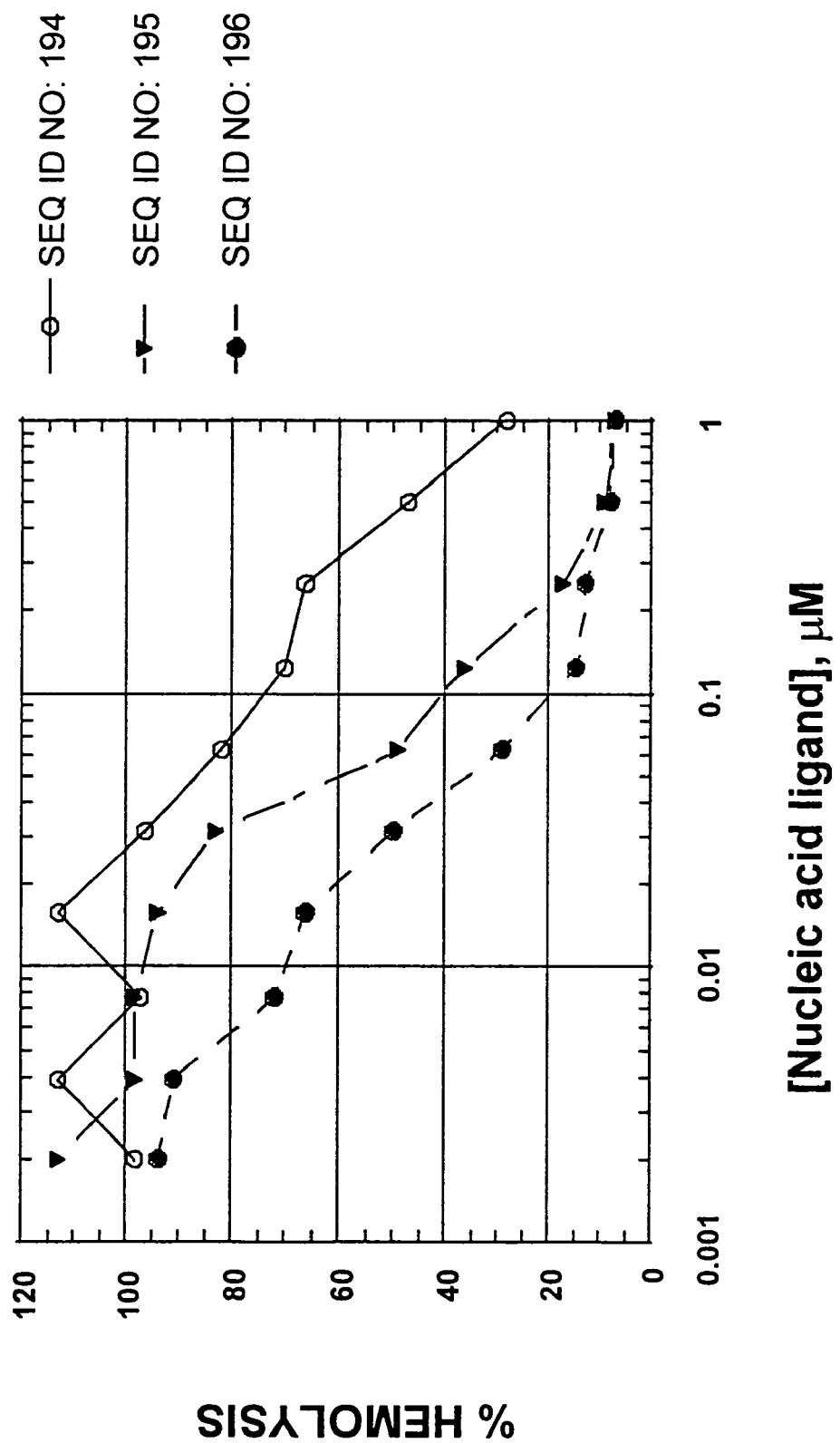
FIG. 6 shows the % hemolysis verses concentration of nucleic acid ligand (μm) for a 38mer truncate of clone YL-13 (SEQ ID NO:175) without 2'-OMe substitution (SEQ ID NO:194; open circles), with a 2'-OMe substitution at position 20 (SEQ ID NO:195; closed triangles) and with 2'-OMe substitutions at positions 2, 7, 8, 13, 14, 15, 20, 21, 22, 26, 27, 28, 36 and 38 (SEQ ID NO:196; closed circles).

Three oligonucleotides were synthesized based on clone YL-13 from the Biased SELEX experiment to compare the effect of 2'-OMe substitution on hemolytic inhibition: (1) a 38mer truncate B2010 (SEQ ID NO: 194), in which all of the nucleotides were 2'-OH; (2) a 38mer in which one nucleotide (position 20) was a 2'-OMe-G (B2070; SEQ ID NO:195); and (3) a 38mer in which the maximum number of allowable positions (positions 2, 7, 8, 13, 14, 15, 20, 21, 22, 26, 27, 28, 36 and 38) were synthesized as 2'-OMe-G and 2'-OMe-A (M6040; SEQ ID NO:196) as shown in Table 13. These were assayed in the hemolytic assay as described in Example 7. The results are shown in FIG. 6. As shown in FIG. 6, the $K_i$ decreased with increased 2'-O-Me substitution. The $K_d$ was marginally better (data not shown). This experiment showed that nucleic acid ligand stability is increased with 2'-OMe substitution, and that long term in vivo inhibition of the complement system is feasible.

TABLE 1

| SEQ ID NO. | |
|---|---|
| | Synthetic DNA Template: |
| 1 and 156 | 5'-TAATACGACTCACTATAGGGAGGACGATGCGG-[N]$_{30\ or\ 50}$-CAGACGACTCGCCCGA-3' |
| | Starting random sequence RNA pool: |
| 2 and 157 | 5'-GGGAGGACGAUGCGG-[N]$_{30\ or\ 50}$-CAGACGACU CGCCCGA-3' |
| | Primer Set for Standard SELEX: |
| 3 | 5'-PRIMER: 5'-TAATACGACTCACTATAGGGAGGACGATGC GG-3' |
| 4 | 3'-PRIMER: 5'-TCGGGCGAGTCGTCTG-3' |
| | Primer Set for Biased SELEX |
| 158 | 5'-PRIMER: 5'-TAATACGACTCACTATAGGGAGATAA GAATAAACGCTCAA-3' |
| 159 | 3'PRIMER: 5'GCCTGTTGTGAGCCTCCTGTCGAA-3' |

TABLE 2

2'-NH$_2$RNA Ligands of Complement System Protein C1q*

| Clone No. | | SEQ ID NO: | Kd(nM) |
|---|---|---|---|
| Family 1 | | | |
| 3 | gggaggacgaugcggGAGGAGUGGAGGUAAA CAAUAGGUCGGUAGCGACUCCCACUAACAGG CCUcagacgacucgcccga | 5 | |
| 12 | gggaggacgaugcggGUGGAGUGGAGGUAAA CAAUAGGUCGGUAGCGACUCCCAGUAACGGC CUcagacgacucgcccga | 6 | |
| 23c | gggaggacgaugcaaGUGGAGUGGAGGUAUA ACGGCCGGUAGGCAUCCCACUCGGGCCUAGC Ucagacgacucgcccga | 7 | |
| 30 | gggaggacgaugcggGUGGAGUGGGGAUCAU ACGGCUGGUAGCACGAGCUCCCUAACAGCGG Ucagacgacucgcccga | 8 | |
| 36 | gggaggacgaugcggGAGGAGUGGAGGUAAA CAAUAGGCCGGUAGCGACUCCCACUAACAGC CUcagacgacucgcccga | 9 | 0.29 |
| 45 | gggaggacgaugcggUGGAGUGGAGGUAUAC CGGCCGUAGCGCAUCCCACUCGGGUCUGUG CUcagacgacucgcccga | 10 | 1.38 |
| 47 | gggaggacgaugcggGUGGAGCGGAGGUUUA UACGGCUGGUAGCUCGAGCUCCCUAACACGC GGUagacgacucgcccga | 11 | |
| 50 | gggaggacgaugcggGUGGAGUGGAGGUAUA ACGGCCGGUAGCGCAUCCCACUCGGGUCUGU GCUagacgacucgcccga | 12 | 0.979 |
| 78 | gggaggacgaugcggGUGGAGUGGAGGGUAA ACAAUGGCUGGUGGCAUUCGGAAUCUCCCAA CGUagacgacucgcccga | 13 | |
| Family 2 | | | |
| 33 | gggaggacgaugcggGUUGCUGGUAGCCUGA UGUGGGUGGAGUGAGUGGAGGGUUGAAAAAU Gcagacgacucgcccga | 14 | 3.85 |
| 40 | gggaggacgaugcggCUGGUAGCAUGUGCAU UGAUGGAGGAGUGGAGGUCACCGUCAACCG Ucagacgacucgcccga | 15 | |
| 43 | gggaggacgaugcggUUUCUCGGCCAGUAGU UUGCGGGUGGAGUGGAGGUAUAUCUGCGUCC UCGcagacgacucgcccga | 16 | |
| Family 3 | | | |
| 14 | gggaggacgaugcggCACCUCACCUCCAUAU UGCCGGUUAUCGCGUAGGGUGAGCCCAGAGA CGAcagacgacucgcccga | 17 | 2.4 |
| 23 | gggaggacgaugcggCACUCACCUUCAUAUU GGCCGCCAUCCCAGGGUUGAGCCCAGACAC AGcagacgacucgcccga | 18 | 23 |
| Family 4 | | | |
| 22 | gggaggacgaugcggGCAUAGUGGGCAUCCC AGGGUUGCCUAACGGCAUCCGGGGUUGUUAU UGGcagacgacucgcccga | 19 | |
| 67 | gggaggacgaugcggCAGACGACUCGCCCGA GGGGAUCCCCCGGGCCUGCAGGAAUUCGAUA Ucagacgacucgcccga | 20 | |

*Lower case letters represent the fixed region.

TABLE 3

2'-F RNA Ligands of Complement System Protein of Human C3*

| Clone No. | | | SEQ ID NO: |
|---|---|---|---|
| C3c 10 | gggaggacgaugcgg | AACUCAAUGGGCCUACUUUUUCCGUGGUCCU | cagacgacucgcccga | 21 |
| C3C 16 | gggaggacgaugcgg | AACUCAAUGGGCCUACUUUUUCCGUGGUCCU | cagacgacucgcccga | 22 |
| C3C 186 | gggaggacgaugcgg | AACUCAAUGGGCCGACUUUUUCCGUGUCCU | cagacgacucgcccg | 23 |
| C3C 162 | gggaggacgaugcgg | AACUCAAUGGGCCGACUUUCCGUGGUCCU | cagacgacucgcccga | 24 |

TABLE 3-continued

2'-F RNA Ligands of Complement System Protein of Human C3*

| Clone No. | | | | SEQ ID NO: |
|---|---|---|---|---|
| C3C 141 | gggaggacgaugcgg | AACUCAAUGGGCNUACUUUUCCGUGGUCCU | cagacgacucgcccga | 25 |
| C3c 32 | gggaggacgaugcgg | AACUCAAUGGGCCGACUUUUCCGUGGUCCU | cagacgacucgcccga | 26 |
| 27C3B143 | gggaggacgaugcgg | AACUCAAUGGGCCGACUUUUCCGUGGUCCU | cagacgacugcccga | 27 |
| 30C3B149 | gggaggacgaugcgg | ACGCAGGGGAUGCUCACUUUGACUUUAGGC | cagacgacucgcccg | 28 |
| c3a 29c | gggaggacgaugcgg | ACUCGGCAUUCACUAACUUUUGCGCUCGU | cagacgacucgcccga | 29 |
| C3B 25 | gggaggacgaugcgg | AUAACGAUUCGGCAUUCACUAACUUCUCGU | cagacgacucgcccga | 30 |
| C3c 3 | gggaggacgaugcgg | AUGACGAUUCGGCAUUCACUAACUUCUCGU | cagacgacucgcccga | 31 |
| C3C 155 | gggaggacgaugcgg | AUGACGAUUCGGCAUUCACUAACUUCUCAU | cagacgacucgcccga | 32 |
| C3C 109 | gggaggacgaugcgg | AUGACGAUUCGGCAUUCACUAACUUCUACU | cagacgacucgcccga | 33 |
| C3-A 18c | gggaggacgaugcgg | AUCUGAGCCUAAAGUCAUUGUGAUCAUCCU | cagacgacucgcccga | 34 |
| C3c 35 | gggaggacgaugcggg | CGUUGGCGAUUCCUAAGUGUCGUUCUCGU | cagacgacucgcccga | 35 |
| C3B 41 | gggaggacgaugcgg | CGUCUCGAGCUCUAUGCGUCCUCUGUGGU | cagacgacucgcccga | 36 |
| C3B 108 | gggaggacgaugcgg | CGUCACGAGCUUUAUGCGUEJCUCUGUGGU | cagacgacucgcccga | 37 |
| C3c 77 | gggaggacgaugcgg | CUUAAAGUUGUUUAUGAUCAUUCCGUACGU | cagacgacucgcccga | 38 |
| C3B 102 | gggaggacgaugcgg | GCGUUGGCGAUUGGUAAGUGUCGUUCUCGU | cagacgacucgcccga | 39 |
| c3a 9c | gggaggacgaugcgg | GCGUCUCGAGCUUUAUGCGUUCUCUGUGGU | cagacgacucgcccga | 40 |
| C3B 138 | gggaggacgaugcgg | GCGUCUCGAGCUCUAUGCGUUCUCUGUGGU | cagacgacucgcccga | 41 |
| c3-8c | ggaggacgaugcgg | GGCCUAAAGUCAAGUGAUCAUCCCCUGCGU | cagacganucgcccga | 42 |
| C3 -23C | gggaggacgaugcgg | GUGGCGAUUCCAAGUCUUCCGUGAACAUGGU | cagacgacucgcccg | 43 |
| C3c 36 | gggaggacgaugcgg | GUGACUCGAUAUCUUCCAAUCUGUACAUGGU | cagacgacucncccga | 44 |
| 188 | gggaggacgaugcgg | UGGCGAUUCCAAGUCUUCCGTGAACATGGT | cagacgacucgcccga | 45 |
| C3B 23 | gggaggacgaugcgg | TGGCGATTCCAAGTCTTCCGTGAACAT | cagacgacucgcccga | 46 |

*Lower case letters represent the fixed region.

TABLE 4

2'-F RNA Ligands of Complement System Protein Human C5*

| Clone No: | | | | SEQ ID NO: |
|---|---|---|---|---|
| Group I | | | | |
| E5c/E11 | gggaggacgaugcgg | UCCGGCGCGCUGAGUGCCGGU UAUCCUCGU | cagacgacucgcccga | 47 |
| A6 | gggaggacgaugcgg | UCCGGCGCGCUGAGUGCCGGUUUAUCCUCGU | cagacgacucgcccga | 48 |
| F8 | gggaggacgaugcgg | UCUCAUGCGCCGAGUGUGAGUUUACCUUCGU | cagacgacucgcccga | 49 |
| K7 | gggaggacgaugcgg | UCUCAUGCGUCGAGUGUGAGUUUAACUGCGU | cagacgacucgcccga | 50 |
| C6 | gggaggacgaugcgg | UCUCAUGCGUCGAGUGUGAGUUUACCUUCGU | cagacgacucgcccga | 51 |
| G7 | gggaggacgaugcgg | UCUGCUACGCUGAGUGGCUGUUUACCUUCGU | cagacgacucgcccga | 52 |
| H1 | gggaggacgaugcgg | UCGGAUGCGCCGAGUCUCCGUUUACCUUCGU | cagacgacucgcccga | 53 |
| Group II | | | | |
| F11 | gggaggacgaugcgg | UGAGCGCGUAUAGCGGUUUCGAUAGAGCUGCGU | cagacgacucgcccga | 54 |
| H2 | gggaggacgaugcgg | UGAGCGCGUAUAGCGGUUUCGAUAGAGCCU | cagacgacucgcccga | 55 |
| H6 | gggaggacgaugcgg | UGAGCGUGGCAAACGGUUUCGAUAGAGCCU | cagacgacucgcccga | 56 |
| H8 | gggaggacgaugcgg | UGAGCGUGUAAAACGGUUUCGAUAGAGCCU | cagacgacucgcccga | 57 |
| C9 | gggaggacgaugcgg | UGAGCGUGUAAAACGGUUUCGAUAGAGCCU | cagacgacucgcccga | 58 |

TABLE 4-continued

2'-F RNA Ligands of Complement System Protein Human C5*

| Clone No: | | | | SEQ ID NO: |
|---|---|---|---|---|
| C12 | gggaggacgaugcgg | UGGGCGUCAGCAUUUCGAUCUUCGGCACCU | cagacgacucgcccga | 59 |
| G9 | gggaggacgaugcgg | GAGUUGUUCGGCAUUUAGAUCUCCGCUCCCU | cagacgacucgcccga | 60 |
| F7 | gggaggacgaugcgg | GCAAAGUUCGGCAUUCAGAUCUCCAUGCCCU | cagacgacucgcccga | 61 |
| E9c | gggaggacgaugcgg | GGCUUCUCACAUAUUCUUCUCUUUCCCCGU | cagacgacucgcccga | 62 |
| E4c | gggaggaggaucgg | UGUUCAGCAUUCAGAUCUU | cagacgacucgcccga | 63 |
| G3 | gggaggacgaugcgg | UGUUCAGCAUUCAGN/AUCUUCACGUGUCGU | cagacgacucgcccga | 64 |
| F6 | gggaggacgaugcgg | UGUUCACCAUUCAGAUCUUCACGUGUCGU | cagacgacucgcccga | 65 |
| D9 | gggaggacgaugc | UGUUCAGCAUUCAGAUCUUCACGUGUGU | cagacgacucgcccga | 66 |
| F4 | gggaggacgaugcgg | UUUCGAUAGAGACUUACAGUUGAGCGCGGU | cagacgacucgcccga | 67 |
| D3 | gggaggacgaugcgg | UUUGUGAUUUGGAAGUGGGGGGGAUAGGGU | cagacgacucgcccga | 68 |
| F9 | gggaggacgaugcgg | UGAGCCUGGCAAACCGUUUCGAUAGAGCCU | cagacgacucgcccga | 69 |
| J1c | ggagggcgauggGG | UGAGCGUGUAAAAGCUUGCGAUAGAGCCU | cagacgacucgcccga | 70 |
| D6 | gggaggacgaugcgg | GUAUCUUAUCUUGUUUUCGUUUUUCUGCCCU | cagacgaucgcccga | 71 |
| E8x | gggaggacgaugcgg | AGGGUUCUUUUCAUCUUCUUUCUUUCCCCU | cagacgacucgcccga | 72 |
| H11 | gggaggacgaugcgg | ACGAAGAAGCUGGUGGAGGAGUUUCGUGCU | cagacgacucgcccga | 73 |
| G10 | gggaggacgaugcgg | ACGAAGAAGGGGGUGGAGGAGUUUCGUGCU | cagacgacucgcccga | 74 |

*Lower case letters represent the fixed region.

TABLE 5

Rat C5 2'F- RNA sequences*

| Clone No: | | | | SEQ ID NO: |
|---|---|---|---|---|
| Family I | | | | |
| RtC5-116 | gggaggacgaugcgg | CGAUUACUGGGACGGACUCGCGAUGUGAGCC | cagacgacucgcccga | 76 |
| RtC5-39 | gggaggacgaugcgg | CGAUUACUCGGACAGACUCGCGAUGUGAGCU | cagacgacucgcccga | 77 |
| RtC5-69 | gggaggacgaugcgg | CGACUACUGGGAAGGG UCGCGAAGUGAGCC | cagacgacucgcccga | 78 |
| RtC5-95 | gggaggacgaugcgg | CGAUUACUGGGACAGACUCGCGAUGUGAGCU | cagacgacucgcccga | 79 |
| RtCB-146 | gggaggacgaugcgg | CGACUACUGGGAGAGU ACGCGAUGUGUGCC | cagacgacucgcccga | 80 |
| Family II | | | | |
| RtC5-168 | gggaggacgaugcgg | GUCCUCGGGGAAAAUUUCGCGACGUGAACCU | cagacgacucgcccga | 81 |
| Family III | | | | |
| RtC5-74 | gggaggacgaugcgg | CUUCUGAAGAUUAUUUCGCGAUGUGAACUUCAGACCCCU | cagacgacucgcccga | 82 |
| RtC5-100 | gggaggacgaugcgg | CUUCUGAAGAUUAUUUCGCGAUGUGAACUCCAGACCCCU | cagacgacucgcccga | 83 |

*Lower case letters represent the fixed region.

TABLE 6

2'-F RNA Ligands of Complement System Protein C1q*

| Clone No: | | | | SEQ ID NO: |
|---|---|---|---|---|
| c1qrd17-33c | gggaggacgaugcgg | AAAGUGGAAGUGAAUGGCCGACUUGUCUGGU | cagacgacucgcccga | 84 |
| CLB100 | gggaggacgaugcgg | AAACCAAAUCGUCGAUCUUUCCACCG UCGU | cagacgacucgcccga | 85 |
| c1q-a8c | gggaggacgaugcgg | AACACGAAACGGAGGUUGACUCGAUCUGGC | cagacgacucgcccga | 86 |
| CLq5 c | ggaggacgaugcgg | AACACGGAAGACAGUGCGACUCGAUCUGGU | cagacgacucgcccga | 87 |
| 32.C1B76c | gggaggacgaugcgg | AACAAGGACAAAAGUGCGAUUCUGUCUGG | cagacgacucgcccg | 88 |
| c1l0c | gggaggacgaugcgg | AACAGACGACUCGCGCAACUACUCUGACGU | cagacgacucgcccga | 89 |
| C1B121c | gggaggacgaugcgg | AACAGGUAGUUGGGUGACUCUGUGUGACCU | cagacgacucgcccga | 90 |
| C1q11c | ggaggacgaugcgg | AACCAAAUCGUCGAUCUUUCCACCGCUCGU | cagacgacucgcccga | 91 |
| C15c | gggaggacgaugcgg | AACCGCUAUUGAAUGUCACUGCUUCGUGCU | cagacgacucgcccga | 92 |
| C1Q-A24'c | gggaggacgaugcgg | AACCGCAUGAGUUACCUGGCUCGCCUCGU | cagacgacucgcccga | 93 |
| C1Q-A5'c | gggaggacgaugcgg | AACCCAAUCGUCUAAAUUCGCUGCUCAUCGU | cagacgacucgcccga | 94 |
| C121c | gggaggacgaugcgg | AACUCAAUGGGCCUACUUUUCCGUGGUCCU | cagacgacucgcccga | 95 |
| C1q-a2C | gggaggacgaugcgg | AAGCGGUGAGUCGUGGCUUUCUCCCUCGAUCCUCGU | cagacgacucgcccga | 96 |
| c1q-a12C | gggaggacgaugcgg | AAGGAUGACGAGGUGGUUCGGGUUUGUGCU | cagacgacucgcccga | 97 |
| c1qrd17-43c | gggaggacgaugcgg | ACAAGACGAGAACGGGGGGAGCUACCUGGC | cagacgacucgcccga | 98 |

TABLE 6-continued

2'-F RNA Ligands of Complement System Protein C1q*

| Clone No: | | | | SEQ ID NO: |
|---|---|---|---|---|
| CIQ-A7'C | gggaggacgaugcgg | AGACACUAAACAAAUUGGCGACCUGACCGU | cagacgacucgcccga | 99 |
| 03.C1Q.137c | gggaggacgaugcgg | AGAGGCUCAGACGACUCGCCCGACCACGGAUGCGACCU | cagacgacucgcccga | 100 |
| 14.C1Q156c | gggaggacgaugcgg | AGAUGGAUGGAAGUGCUAGUCUUCUGGGGU | cagacgacucgccc | 101 |
| C1B119c | gggaggacgaugcgg | AGAUGGAUGGAAGUGCUAGUCUUUCUGGGGU | cagacgacucgcccga | 102 |
| C1Q-A28'C | gggaggacgaugcgg | AGCAGUUGAAAGACGUGCGUUUCGUUUGGU | cagacgacucgcccga | 103 |
| 15.CLQ.157c | gggaggacgaugcgg | AGCACAAUUUUUUCCUUUUCUUUUCGUCCACGUGCU | cagacgacucgcccga | 104 |
| 44C1qb60c | gggaggacgaugcgg | AGCUGAUGAAGAUGAUCUCUGACCCCU | cagacgacucgcccga | 105 |
| 06.C1Q.143c | gggaggacgaugcgg | AGCUGAAAGCGAAGUGCGAGGUGUUUGGUC | cagacgacucgcccga | 106 |
| C1q4c | ggaggacgaugcgg | AGCGAAAGUGCGAGUGAUUGACCAGGUGCU | cagacgacucgcccga | 107 |
| c1qrd17-52c | gggaggacgaugcgg | AGCGUGAGAACAGUUGCGAGAUUGCCUGGU | cagacgacucgcccga | 108 |
| C111c | gggaggacgaugcgg | AGGAGAGUGUGGUGAGGGUCGUUUUGAGGGU | cagacgacucgcccga | 109 |
| 44c1Qb60c | gggaggacgaugcgg | AGGAGCUGAUGAAGAUGAUCUCUGACCCCU | cagacgacucgcccga | 110 |
| 24clqb51c | gggaggacgaugcgg | AGUUCCCAGCCGCCUUGAUUUCUCCGUGGU | cagacgacucgcccga | 111 |
| 31clqb16c | gggaggacgaugcgg | AUAAGUGCGAGUGUAUGAGGUGCGUGUGGU | cagacgacucgcccga | 112 |
| 28c1Qb20c | gggaggacgaugcgg | AUCUGAGGAGCUCUUCGUCGUGCUGAGGGU | cagacgacucgcccga | 113 |
| clqrd17-61c | gggaggacgaugcgg | AUCCGAAUCUUCCUUACACGUCCUGCUCGU | cagacgacucgcccga | 114 |
| C1q17c | ggaggacgaugcgg | AUCCGCAAACCGACAGCUCGAGUUCCGCCU | cagacgacucgcccga | 115 |
| 34clqb27c | gggaggacgaugcgg | AUGGUACUUUAGUCUUCCUUGAUUCCGCCU | cagacgacucgcccga | 116 |
| C1q16c | ggaggacgaugcgg | AUGAUGACUCAACGUGCGACUCGACCUGGC | cagacgacucgcccga | 117 |
| C1q7c | ggaggacgaugcgg | AUGAGGAGGAAGAGUCUGAGGUGCUGGGGU | cagacgacucgcccga | 118 |
| C1Q-A2'C | gggaggacgaugcgg | AUUUCGGUCGACUAAAUAGGGGUGGCUCGU | cagacgacucgcccga | 119 |
| C122c | gggaggacgaugcgg | CAAGAGGUCAGACGACUGCCCCGAGUCCUCCCCCGGU | cagacgacucgcccga | 120 |
| C115c | gggaggacgaugcgg | CAGUGAAAGGCGAGUUUUCUCCCUCUCCCU | cagacgacucgcccga | 121 |
| 09.C1Q.149c | gggaggacgaugcgg | CAUCGUUCAGGAGAAUCCACUUCGCCUCGU | cagacgacucgcccga | 122 |
| 04.C1Q.138c | gggaggacgaugcgg | CAUCUUCCUUGUUCUUCCAACCGUGCUCCU | cagacgacucgcccga | 123 |
| C1Q-A4'C | gggaggacgaugcgg | CAUCGUAAACAAUUUGUUCCAUCUCCGCCU | cagacgacucgcccga | 124 |
| clqrd17-64c | gggaggacgaugcgg | CAUUGUCCAAGUUUAGCUGUCCGUGCUCGU | cagacgacucgcccga | 125 |
| 46C1Qb64c | gggaggacgaugcgg | CAUAGUCCGGAUACUAGUCACCAGCUCGU | agacgacucgcccga | 126 |
| C1q6 c | ggaggacgaugcgg | CCGUCUCGAUCCUUCUAUGCCUUCGCUCGU | cagacgacucgcccga | 127 |
| 23C1Qb4x | gggaggacgaugcgg | CGGGAAGUUUGAGGUGUANUACCUGUUGUCUGGU | cagacgacucgcccga | 128 |
| clqrd17-63c | gggaggacgaugcgg | CUCAACUCUCCCACAGACGACUCGCCCGGGCCUCCU | cagacgacucgcccga | 129 |
| clqrd17-47c | gggaggacgaugcgg | GACUCCUCGACCGACUCGACCGGCUCGU | cagacgacucgccga | 130 |
| C1q9c | ggaggacgaugcgg | GAACCAAAUCGUCGAUCUUUCCACCGCUCGU | cagacgacucgcccga | 131 |
| C1Q-A10'C | gggaggacgaugcgg | GACCACCUCGAUCCUCAGCGCCAUUGCCCU | cagacgacucgcccga | 132 |
| C119c | gggaggacgaugcgg | GAAGUGGAAGGGUAGUUGUGUGACCU | cagacgacucgcccga | 133 |
| clqrd17-42c | cgggaggacgaugcgg | GCAAACUUUUCCUUUUCCCUUUAUCUUCCUUGCCCU | cagacgacucgcccga | 134 |
| 30c1Q24c | gggaggacgaugcgg | GGCCGACGAUUCACCAAUGUUCUCUCUGGU | cagacgacucgcccga | 135 |
| C1q10c | ggaggacgaugcgg | GGUUCCUCAAUGACGAUCUCCAUUCCGCUCGU | cagacgacucgcccag | 136 |
| C1q20c | ggaggacgaugcgg | GUCGACAUUGAAGCUGCUCUGCCUUGAUCCU | cagacgacucgcccag | 137 |
| 08.C1Q.147c | gggaggacgaugcgg | UCCAAUUCGUUCUCAUGCCUUUCCGCUCGU | cagacgacucgcccga | 138 |
| 11.C1Q.152c | gggaggacgaugcgg | UCCGCAAGUUUAGCACUCACUGCCUCGU | cagacgacucgcccga | 139 |
| 26clQb4c | gggaggacgaugcgg | UCCACAUCGAAUUUUCUGUCCGUUCGU | cagacgacucgcccga | 140 |
| C1B115c | gggaggacgaugcgg | UCGAUGUUCUUCCUCACCACUGCUCGUCGCCU | cagacgacucgcccga | 141 |
| 33c1Q26c | gggaggacgaugcgg | UCGAGCUGAGAGGGGCUACUUGUUCUGGUCA | cagacgacucgcccga | 142 |
| 01.C1Q.135c | gggaggacgaugcgg | UGGAAGCGAAUGGGCUAGGGUGGGCUGACCUC | cagacgacucgcccga | 143 |
| 47clqb65c | gggaggacgaugcgg | UGGACUUCUUUUCCUCUUCCUCCUUCCGCCGGU | cagacgacucgcccga | 144 |
| C1q14c | ggaggacgaugcgg | UUCCAAAUCGUCUAAGCAUCGCUCGCUCGU | cagacgacucgcccag | 145 |
| clqrd17-53c | gggaggacgaugcgg | UUCCACAUCGCAAUUUUCUGUCCGUGCUCGU | cagacgacucgcccga | 146 |
| c1q-a6C | gggaggacgaugcgg | UUCCACAUCGAAUUUUCUGUCCGUGCUCGU | cagacgacucgcccga | 147 |
| C1B114c | gggaggacgaugcgg | UUCCGAUCGACUCCACAUACAUCUGCUCGU | cagacgacucgcccga | 148 |
| clqrd17-56c | gggaggacgaugcgg | UUCCGACAUCGAUGUUGCUCUUCGCCUCGU | cagacgacucgcccga | 149 |
| 05.C1Q.142c | gggaggacgaugcgg | UUCCGAAGUUCUUCCCCCGAGCCUUCCCCUC | cagacgacucgcccga | 150 |
| 30clq24c | gggaggacgaugcgg | UUCCGACGAUUCUCCAAUGUUCUCUCUGGU | cagacgacucgcccga | 151 |
| 38clqb45c | gggaggacgaugcgg | UUCCGACGAUUCUCCAAUCUUCUCUCUGGU | cagacgacucgcccga | 152 |
| 10.C1Q151c | gggaggacgaugcgg | UUCCGCAAGUUUAGACACUCACUGCCUCGU | cagacgacucgcccga | 153 |
| C113x | gggaggacgaugcgg | UUCCGCAAAGUAGAUAUNUCAUCCGCACGU | cagacgacucgcccga | 154 |
| 10.C1B.134c | gggaggacgaugcgg | UUGAGUGGACAGUGCGAUUCGUUUUGGGGU | cagacgacucgcccga | 155 |

*Lower case letters represent the fixed region.

TABLE 7

Binding affinity of C5 nucleic acid ligands

| Clone | SEQ ID NO | Kd (nM) |
|---|---|---|
| A6 | 48 | 35 |
| E11 | 47 | 60 |
| E4 | 63 | 50 |
| C6 | 51 | 30 |
| C9 | 58 | 45 |
| G3 | 64 | 55 |
| F8 | 49 | 30 |

TABLE 8

Effect of truncation of clone C6 on C5 binding

| SEQ ID NOS: | Sequence | Length (nts) | Kd (nM) |
|---|---|---|---|
| *75 | gA CgAUgCggUCUCAUgCgUCgAgUgUgAgUUU ACCUUCg UG | 42 | |
| 160 | CgAUgCggUCUCAUgCgUCgAgUgUgAgUUUAC CUUCg | 38 | 20 |
| 161 | gAUgCggUCUCAUgCgUCgAgUgUgAgUUUACC UUC | 36 | 50 |
| 162 | AUgCggUCUCAUgCgUCgAgUgUgAgUUUACCUU | 34 | >$10^6$ |

*Fragment of SEQ ID NO:51 (Table 4)

TABLE 9

Binding of SELEX pools

| SELEX pool | Kd |
|---|---|
| random pool | >1 nM |
| First SELEX, round 12 | 100 nM |
| Biased SELEX, round 8 | 5 nM |

TABLE 10

Clones from Biased SELEX

| Clone No. | | SEQ ID NO: |
|---|---|---|
| template | gggagataagaataaacgctcaag GAC-GATGCGGTCTCATGCGTCGAGTGTGAGTTTACCTTCG TC ttcgacaggaggctcacaacaggc | 163 |
| YL-8 (10): | gggagauaagaauaaacgcucaag UGC-GACGCGGUCUCGAGCGCGGAGUUCGAGUUUACCUUCG CA uucgacaggaggcucacaacaggc | 164 |
| YL-33 (2): | gggagauaagaauaaacgcucaag CUC-GACGCGGUCCCAGGCGUGGAGUCUGGGUUUACCUUCG AG uucgacaggaggcucacaacaggc | 165 |
| YL-79 (3): | gggagauaagaauaaacgcucaag AAC-CACGCGGUCUCAGGCGUAGAGUCUGAGUUUACCUUGG UU uucgacaggaggcucacaacaggc | 166 |
| YL-1 (2): | gggagauaagaauaaacgcucaag AAC-CACGCGGUCUCAGGCGUAGAGUCUGUGUUUACCUUGG UU uucgacaggaggcucacaacaggc | 167 |
| YL-71: | gggagauaagaauaaacgcucaag UGC-GACGCGGUCUCGAGCGCGGAGUUCGAGUUCACCUUCG CA uucgacaggaggcucacaacaggc | 168 |
| YL-39: | gggagauaagaauaaacgcucaag CA-CAACGCGGUCUCAUGCGUCGAGUAUGAGUUUACCUUUG UG uucgacaggaggcucacaacaggc | 169 |
| YL-60: | gggagauaagaauaaacgcucaag GUC-CUCGCGGUCUCAUGCGCCGAGUAUGAGUUUACCUAGG AC uucgacaggaggcucacaacaggc | 170 |
| YL-9: | gggagauaagaauaaacgcucaag-GU CGUCGCGGUCUGAUGCGCUGAGUAUCAGUUUACCUACG AC uucgacaggaggcucacaacaggc | 171 |
| YL-56: | gggagauaagaauaaacgcucaag GUA-CACGCGGUCUGACGCGCUGAGUGUCAGUUUACCUUGU AC uucgacaggaggcucacaacaggc | 172 |
| YL-63: | gggagauaagaauaaacgcucaag AAAC-CACGCGGUCUCAGGCGCAGAGUCUGAGUUUACCUUCG CA uucgacaggaggcucacaacaggc | 173 |

TABLE 10-continued

Clones from Biased SELEX

| Clone No. | Sequence | SEQ ID NO: |
|---|---|---|
| YL-29: | gggagauaagaauaaacgcucaag AA C-CACGCGGUCUCAGGCGCAGAGUCUGAGUUUACCUUGG UU uucgacaggaggcucacaacaggc | 174 |
| YL-13: | gggagauaagaauaaacgcucaag- GA CGCCGCGGUCUCAGGCGCUGAGUCUGAGUUUACCUGCG UC uucgacaggaggcucacaacaggc | 175 |
| YL-24: | gggagauaagaauaaacgcucaag- GC UGACGCGGUCUCAGGCGUGGAGUCUGAGUUUACCUUCG GC uucgacaggaggcucacaacaggc | 176 |
| YL-3: | gggagauaagaauaaacgcucaag- CA UGACGCGGUCUCAGGCGUGGAGUCUGAGUUUACCUUCG UG uucgacaggaggcucacaacaggc | 177 |
| YL-67: | gggagauaagaauaaacgcucaag GU C-GACGCGGUCUCAGGCGUUGAGUCUGUGUUUACCUUCG AC uucgacaggaggcucacaacaggc | 178 |
| YL-69: | gggagauaagaauaaacgcucaag GU C-GACGCGGUCUCAGGCGUUGAGUCUGUGUUUACCUUCG AC uucgacaggaggcucacaacaggc | 179 |
| YL-81: | gggagauaagaauaaacgcucaag- GA CGCCGCGGUCUCAGGCGUUGAGUCUGAGUUUACCUGCG UC uucgacaggaggcucacaacaggc | 180 |
| YL-15(7): | gggagauaagaauaaacgcucaag GA C-GACGCGGUCUGAUGCGCUGAGUGUCAGUUUACCUUCG UC uucgacaggaggcucacaacaggc | 181 |
| YL-84: | gggagauaagaauaaacgcucaag AA C-GACGCGGUCUGAUGCGCUGAGUGUCAGUGUACCUUCG UC uucgacaggaggcucacaacaggc | 182 |
| YL-4 (3): | gggagauaagaauaaacgcucaag GU C-GACGCGGUCUGAUGCGUAGAGUGUCAGUUUACCUUCG AC uucgacaggaggcucacaacaggc | 183 |
| YL-51: | gggagauaagaauaaacgcucaag GU C-GACGCGGUCUGAUGCGUAGAGUGUCAGUUCACCUUCG AC uucgacaggaggcucacaacaggc | 184 |
| YL-14 (2): | gggagauaagaauaaacgcucaag UA C-GACGCGGUCCCGUGCGUGGAGUGCGGGUUUACCUUCG UA uucgacaggaggcucacaacaggc | 185 |
| YL-23: | gggagauaagaauaaacgcucaag GA C-GACGCGGUCUGAUGCGCAGAGUGUCGGUUUACCUUUG UC uucgacaggaggcucacaacaggc | 186 |
| YL-59: | gggagauaagaauaaacgcucaag GA C-GACGCNGUCUGAUGCGCAGAGUGUCAGUUUACCUUCG AC uucgacaggaggcucacaacaggc | 187 |
| YL-91: | gggagauaagaauaaacgcucaag GA C-GACGCGGUCUGAUGCGCAGAGUGUCAGUUUACCUUCG UC uucgacaggaggcucacaacaggc | 188 |
| YL-50: | gggagauaagaauaaacgcucaag GA C-GACGCGGUCGGAUGCGCAGAGUGUCCGUUUACCUUCG UC uucgacaggaggcucacaacaggc | 189 |

*Lower case letters represent the fixed region.

TABLE 11

Binding affinity of clones from Biased SELEX experiment

| SEQ ID NO: | Clone | Kd (nM) |
|---|---|---|
| 166 | YL-79 | 15 |
| 172 | YL-56 | 12 |
| 175 | YL-13 | 6 |
| 185 | YL-14 | 25 |
| 163 | Template | 30 |

TABLE 12

Sequences based on YL-13 from Biased SELEX

| Clone | Sequence | SEQ ID NO: |
|---|---|---|
| M3010 | C<u>G</u>C CGC G<u>G</u>U CUC A<u>G</u>G CGC UGA <u>G</u>UC UGA <u>G</u>UU <u>U</u>AC CUG CG | 190 |
| M3020 | CGC CGC G<u>G</u>U CUC G<u>G</u>G C<u>G</u>C UGA GUC UGA GUU UAC CU<u>G</u> CG | 191 |
| M3030 | CGC CGC GGU CUC A<u>G</u>G CGC UGA GUC UGA GUU <u>U</u>AC CUG C<u>G</u> | 192 |

<u>G</u>, <u>A</u> = 50% 2'-OH:50% 2'-OMe

TABLE 13

Truncates based on YL-13 for hemolytic assay

| Clone | Sequence | SEQ ID NO: |
|---|---|---|
| YL-13t | CGC CGC GGU CUC AGG CGC UGA GUC UGA GUU UAC CUG CG | 194 |
| B2070 | CGC CGC GGU CUC AGG CGC UGA GUC UGA GUU UAC CUG CG | 195 |
| M6040 | C<u>G</u>C CGC <u>GG</u>U CUC A<u>GG</u> CGC UG<u>A</u> <u>G</u>UC UG<u>A</u> GUU UAC CU<u>G</u> C<u>G</u> | 196 |

<u>G</u>, <u>A</u> = 100% 2'-OMe

---

We claim:

1. A method for inhibiting inflammation or membrane attack vascular disease comprising administering to a patient in need thereof a pharmaceutically effective amount of a nucleic acid ligand of a C5 complement system protein wherein said nucleic acid ligand comprises the polynucleotide of SEQ ID NO: 194, 195, or 196.

2. The method of claim 1 wherein said nucleic acid ligand comprises the polynucleotide of SEQ ID NO: 196.

3. The method of claim 1 wherein said nucleic acid ligand comprises the polynucleotide of SEQ ID NO: 194.

4. The method of claim 1 wherein said nucleic acid ligand comprises the polynucleotide of SEQ ID NO: 195.

5. A method for inhibiting activation of a membrane attack pathway in vivo, the method comprising administering to a patient in need thereof a pharmaceutically effective amount of a nucleic acid ligand comprising the polynucleotide of SEQ ID NO: 194, 195 or 196.

6. The method of claim 5 wherein said nucleic acid ligand comprises the polynucleotide of SEQ ID NO: 194.

7. The method of claim 5 wherein said nucleic acid ligand comprises the polynucleotide of SEQ ID NO: 195.

8. The method of claim 5 wherein said nucleic acid ligand comprises the polynucleotide of SEQ ID NO: 196.

9. A method for inhibiting C5 complement activation, the method comprising administering to a patient in need thereof a pharmaceutically effective amount of a nucleic acid ligand comprising the polynucleotide of SEQ ID NO: 194, 195 or 196.

10. The method of claim 9 wherein said nucleic acid ligand comprises the polynucleotide of SEQ ID NO: 194.

11. The method of claim 9 wherein said nucleic acid ligand comprises the polynucleotide of SEQ ID NO: 195.

12. The method of claim 9 wherein said nucleic acid ligand comprises the polynucleotide of SEQ ID NO: 196.

13. The method of claim 1, wherein the ligand inhibits activation of the inflammation or the membrane attack pathway.

14. The method of claim 1, wherein the ligand is connected via a linker to a non-immunogenic, high molecular weight compound.

15. The method of claim 5, wherein the ligand is connected via a linker to a non-immunogenic, high molecular weight compound.

16. The method of claim 9, wherein the ligand is connected via a linker to a non-immunogenic, high molecular weight compound.

17. The method of claim 1, wherein inflammation is inhibited.

18. The method of claim 1, wherein membrane attack vascular disease is inhibited.

19. A method for inhibiting hemolysis, renal injury in autoimmune glomerulonephritis or leukocyte activation during extracorporeal circulation, comprising administering to a patient in need thereof a pharmaceutically effective amount of a nucleic acid ligand comprising the polynucleotide of SEQ ID NO: 194, 195 or 196.

20. The method of claim 19 wherein said nucleic acid ligand comprises the polynucleotide of SEQ ID NO: 194.

21. The method of claim 19 wherein said nucleic acid ligand comprises the polynucleotide of SEQ ID NO: 195.

22. The method of claim 19 wherein said nucleic acid ligand comprises the polynucleotide of SEQ ID NO: 196.

23. The method of claim 19, wherein the ligand is connected via a linker to a non-immunogenic, high molecular weight compound.

24. The method of claim 14, wherein the non-immunogenic, high molecular weight compound is polyethylene glycol.

25. The method of claim 15, wherein the non-immunogenic, high molecular weight compound is polyethylene glycol.

26. The method of claim 16, wherein the non-immunogenic, high molecular weight compound is polyethylene glycol.

27. The method of claim 23, wherein the non-immunogenic, high molecular weight compound is polyethylene glycol.

* * * * *

SEQUENCE LISTING

```
<160> NUMBER OF SEQ ID NOS: 198

<210> SEQ ID NO 1
<211> LENGTH: 78
<212> TYPE: DNA
<213> ORGANISM: Artificial Sequence
<220> FEATURE:
<221> NAME/KEY: unsure
<222> LOCATION: (33)..(62)
<223> OTHER INFORMATION: Description of Artificial Sequence: Completely
      Synthesized Nucleic Acid. N's at position 33-62 are
      a or c or g or t

<400> SEQUENCE: 1
taatacgact cactataggg aggacgatgc ggnnnnnnnn nnnnnnnnnn nnnnnnnnn      60 nncagacgac tcgcccga                                                  78

<210> SEQ ID NO 2
<211> LENGTH: 61
<212> TYPE: RNA
<213> ORGANISM: Artificial Sequence
<220> FEATURE:
<221> NAME/KEY: unsure
<222> LOCATION: (16)..(55)
<223> OTHER INFORMATION: Description of Artificial Sequence: Completely
      Synthesized Nucleic Acid.  N's at position 16-55
      are a or c or g or u.
<220> FEATURE:
<221> NAME/KEY: modified_base
<222> LOCATION: (1)..(61)
<223> OTHER INFORMATION: All c's and u's are 2'-F

<400> SEQUENCE: 2
gggaggacga ugcggnnnnn nnnnnnnnnn nnnnnnnnnn nnnncagac gacucgcccg      60 a                                                                    61

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Completely
      Synthesized Nucleic Acid

<400> SEQUENCE: 3
taatacgact cactataggg aggacgatgc gg                                  32

<210> SEQ ID NO 4
```

```
<211> LENGTH: 16
<212> TYPE: DNA
<213> ORGANISM: Artificial Sequence
<220> FEATURE:
<223> OTHER INFORMATION: Description of Artificial Sequence: Completely
      Synthesized Nucleic Acid

<400> SEQUENCE: 4
tcgggcgagt cgtctg                                                      16

<210> SEQ ID NO 5
<211> LENGTH: 81
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(81)
<223> OTHER INFORMATION: All c's and u's are 2'-NH2

<400> SEQUENCE: 5
gggaggacga ugcgggagga guggagguaa acaauagguc gguagcgacu cccacuaaca     60
ggccucagac gacucgcccg a                                                81

<210> SEQ ID NO 6
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 6
gggaggacga ugcgggugga guggagguaa acaauagguc gguagcgacu cccaguaacg     60
gccucagacg acucgcccga                                                  80

<210> SEQ ID NO 7
<211> LENGTH: 79
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(79)
<223> OTHER INFORMATION: All c's and u's are 2'-NH2

<400> SEQUENCE: 7
gggaggacga ugcaagugga guggagguau aacggccggu aggcauccca cucgggccua     60
gcucagacga cucgcccga                                                   79

<210> SEQ ID NO 8
<211> LENGTH: 79
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(79)
<223> OTHER INFORMATION: All c's and u's are 2'-NH2
```

<400> SEQUENCE: 8
gggaggacga ugcgggugga gugggaauca uacggcuggu agcacgagcu cccuaacagc    60
ggucagacga cucgcccga                                                 79

<210> SEQ ID NO 9
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 9
gggaggacga ugcgggagga guggagguaa acaauaggcc gguagcgacu cccacuaaca    60
gccucagacg acucgcccga                                                80

<210> SEQ ID NO 10
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 10
gggaggacga ugcgguggag uggagguaua ccggccggua gcgcauccca cucggguucug    60 ugcucagacg acucgcccga                                                80

<210> SEQ ID NO 11
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 11
gggaggacga ugcgggugga gcggagguuu auacggcugg uagcucgagc ucccuaacac    60
gcgguagacg acucgcccga                                                80

<210> SEQ ID NO 12
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 12
gggaggacga ugcgggugga guggagguau aacggccggu agcgcauccc acucggguucu    60

```
gcgguagacg acucgcccga                                                 80

<210> SEQ ID NO 13
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 13
gggaggacga ugcgggugga guggagggua aacaauggcu gguggcauuc ggaaucuccc     60
gcgguagacg acucgcccga                                                 80

<210> SEQ ID NO 14
<211> LENGTH: 79
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(79)
<223> OTHER INFORMATION: All c's and u's are 2'-NH2

<400> SEQUENCE: 14
gggaggacga ugcggguugc ugguagccug augugggugg agugagugga ggguugaaaa     60
augcagacga cucgcccga                                                  79

<210> SEQ ID NO 15
<211> LENGTH: 79
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(79)
<223> OTHER INFORMATION: All c's and u's are 2'-NH2

<400> SEQUENCE: 15
gggaggacga ugcggcuggu agcaugugca uugaugggag gaguggaggu caccgucaac     60
cgucagacga cucgcccga                                                  79

<210> SEQ ID NO 16
<211> LENGTH: 81
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(81)
<223> OTHER INFORMATION: All c's and u's are 2'-NH2

<400> SEQUENCE: 16
gggaggacga ugcgguuucu cggccaguag uuugcgggug gaguggaggu auaucugcgu     60
ccucgcagac gacucgcccg a                                               81
```

```
<210> SEQ ID NO 17
<211> LENGTH: 81
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(81)
<223> OTHER INFORMATION: All c's and u's are 2'-NH2

<400> SEQUENCE: 17
gggaggacga ugcggcaccu caccuccaua uugccgguua ucgcguaggg ugagcccaga    60
cacgacagac gacucgcccg a                                             81

<210> SEQ ID NO 18
<211> LENGTH: 80
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(80)
<223> OTHER INFORMATION: All c's and u's are 2'-NH2

<400> SEQUENCE: 18
gggaggacga ugcggcacuc accuucauau uggccgccau ccccagggu uu gagcccagac    60 acagcagacg acucgcccga                                               80

<210> SEQ ID NO 19
<211> LENGTH: 81
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(81)
<223> OTHER INFORMATION: All c's and u's are 2'-NH2

<400> SEQUENCE: 19
gggaggacga ugcgggcaua gugggcaucc caggguugcc uaacggcauc cgggguuguu    60
auuggcagac gacucgcccg a                                             81

<210> SEQ ID NO 20
<211> LENGTH: 78
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(78)
<223> OTHER INFORMATION: All c's and u's are 2'-NH2

<400> SEQUENCE: 20
gggaggacga ugcggcagac gacucgcccg aggggauccc ccgggccugc ggaauucgau    60
aucagacgac ucgcccga                                                 78

<210> SEQ ID NO 21
<211> LENGTH: 62
<212> TYPE: RNA
<213> ORGANISM: Artificial Sequence
```

```
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 21
gggaggacga ugcggaacuc aaugggccua cuuuuccgu ggccucaga cgacucgccc      60 ga                                                                   62

<210> SEQ ID NO 22
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 22
gggaggacga ugcggaacuc aaugggccua cuuuccgug guccucagac gacucgcccg      60
a                                                                    61

<210> SEQ ID NO 23
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 23
gggaggacga ugcggaacuc aaugggccga cuuuuccgu guccucagac gacucgcccg      60

<210> SEQ ID NO 24
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 24
gggaggacga ugcggaacuc aaugggccga cuuuccgugg uccucagacg acucgcccga     60

<210> SEQ ID NO 25
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(61)
<223> OTHER INFORMATION: All c's and u's are 2'-F
<220> FEATURE:
```

```
<221> NAME/KEY: unsure
<222> LOCATION: (52)
<223> OTHER INFORMATION: Description of Artificial Sequence: Completely
      Synthesized Nucleic Acid. N at position 28 is
      a or c or g or u

<400> SEQUENCE: 25
gggaggacga ugcggaacuc aaugggcnua cuuuccgug guccucagac gacucgcccg    60
a                                                                  61

<210> SEQ ID NO 26
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 26
gggaggacga ugcggaacuc aaugggccga cuuuccgug guccucagac gacucgcccg    60
a                                                                  61

<210> SEQ ID NO 27
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 27
gggaggacga ugcggaacuc aaugggccga cuuuccgug guccucagac gacugcccga    60

<210> SEQ ID NO 28
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 28
gggaggacga ugcggacgca ggggaugcuc acuuugacuu uaggccagac gacucgcccg    60

<210> SEQ ID NO 29
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 29
```

```
gggaggacga ugcggacucg gcauucacua acuuuugcgc ucgucagacg acucgcccga      60
```

<210> SEQ ID NO 30
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 30

```
gggaggacga ugcggauaac gauucggcau ucacuaacuu cucgucagac gacucgcccg      60
a                                                                     61
```

<210> SEQ ID NO 31
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 31

```
gggaggacga ugcggaugac gauucggcau ucacuaacuu cucgucagac gacucgcccg      60
a                                                                     61
```

<210> SEQ ID NO 32
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized  Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 32

```
gggaggacga ugcggaugac gauucggcau ucacuaacuu cucaucagac gacucgcccg      60
a                                                                     61
```

<210> SEQ ID NO 33
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 33

```
gggaggacga ugcggaugac gauucggcau ucacuaacuu cuacucagac gacucgcccg      60
a                                                                     61
```

<210> SEQ ID NO 34

-continued

<210> SEQ ID NO 34
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 34
gggaggacga ugcggaucug agccuaaagu cauugugauc auccucagac gacucgcccg    60
a                                                                  61

<210> SEQ ID NO 35
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 35
gggaggacga ugcgggcguu ggcgauuccu aagugucguu cucgucagac gacucgcccg    60
a                                                                  61

<210> SEQ ID NO 36
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 36
gggaggacga ugcggcgucu cgagcucuau gcguccucug uggucagacg acucgcccga    60

<210> SEQ ID NO 37
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 37
gggaggacga ugcggcguca cgagcuuuau gcguucucug uggucagacg acucgcccga    60

<210> SEQ ID NO 38
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base

```
<222> LOCATION: (1)..(61)
<223> OTHER INFORMATION: All c's and u's are 2'-F

<400> SEQUENCE: 38
gggaggacga ugcggcuuaa aguuguuuau gaucauuccg uacgucagac gacucgcccg    60
a                                                                  61

<210> SEQ ID NO 39
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 39
gggaggacga ugcgggcguu ggcgauuggu aagugucguu cucgucagac gacucgcccg    60
a                                                                  61

<210> SEQ ID NO 40
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 40
gggaggacga ugcgggcguc ucgagcuuua ugcguucucu guggucagac gacucgcccg    60
a                                                                  61

<210> SEQ ID NO 41
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 41
gggaggacga ugcgggcguc ucgagcucua ugcguucucu guggucagac gacucgcccg    60
a                                                                  61

<210> SEQ ID NO 42
<211> LENGTH: 60
<212> TYPE: RNA
<213> ORGANISM: Artificial Sequence
<220> FEATURE:
<221> NAME/KEY: unsure
<222> LOCATION: (52)
<223> OTHER INFORMATION: Description of Artificial Sequence: Completely
      Synthesized Nucleic Acid. N at position 52 is
      a or c or g or u
<220> FEATURE:
<221> NAME/KEY: modified_base
<222> LOCATION: (1)..(60)
```

```
<223> OTHER INFORMATION: All c's and u's are 2'-F

<400> SEQUENCE: 42
ggaggacgau gcggggccua aagucaagug aucauccccu gcgucagacg anucgcccga        60

<210> SEQ ID NO 43
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 43
gggaggacga ugcggguggc gauuccaagu cuuccgugaa cauggucaga cgacucgccc        60
g                                                                        61

<210> SEQ ID NO 44
<211> LENGTH: 62
<212> TYPE: RNA
<213> ORGANISM: Artificial Sequence
<220> FEATURE:
<221> NAME/KEY: unsure
<222> LOCATION: (57)
<223> OTHER INFORMATION: Description of Artificial Sequence: Completely
      Synthesized Nucleic Acid. N at position 57 is
      a or c or g or u
<220> FEATURE:
<221> NAME/KEY: modified_base
<222> LOCATION: (1)..(62)
<223> OTHER INFORMATION: All c's and u's are 2'-F

<400> SEQUENCE: 44
gggaggacga ugcgggugac ucgauaucuu ccaaucugua cauggucaga cgacucnccc        60
ga                                                                       62

<210> SEQ ID NO 45
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 45
gggaggacga ugcgguggcg auuccaaguc uuccgugaac auggucagac gacucgcccg        60
a                                                                        61

<210> SEQ ID NO 46
<211> LENGTH: 58
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(58)
<223> OTHER INFORMATION: All c's and u's are 2'-F

<400> SEQUENCE: 46
```

```
gggaggacga ugcgguggcg auuccaaguc uuccgugaac aucagacgac ucgcccga      58
```

<210> SEQ ID NO 47
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 47

```
gggaggacga ugcgguccgg cgcgcugagu gccgguuauc cucgucagac gacucgcccg      60
a                                                                     61
```

<210> SEQ ID NO 48
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 48

```
gggaggacga ugcgguccgg cgcgcugagu gccgguuuau ccucgucaga cgacucgccc      60
ga                                                                    62
```

<210> SEQ ID NO 49
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 49

```
gggaggacga ugcggucuca ugcgccgagu gugaguuuac cuucgucaga cgacucgccc      60
ga                                                                    62
```

<210> SEQ ID NO 50
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 50

```
gggaggacga ugcggucuca ugcgucgagu gugaguuuaa cugcgucaga cgacucgccc      60
ga                                                                    62
```

```
<210> SEQ ID NO 51
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 51
gggaggacga ugcggucuca ugcgucgagu gugaguuuac cuucgucaga cgacucgccc      60
ga                                                                    62

<210> SEQ ID NO 52
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 52
gggaggacga ugcggucugc uacgcugagu ggcuguuuac cuucgucaga cgacucgccc      60
ga                                                                    62

<210> SEQ ID NO 53
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 53
gggaggacga ugcggucgga ugcgccgagu cuccguuuac cuucgucaga cgacucgccc      60
ga                                                                    62

<210> SEQ ID NO 54
<211> LENGTH: 64
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(64)
<223> OTHER INFORMATION: All c's and u's are 2'-F

<400> SEQUENCE: 54
gggaggacga ugcggugagc gcguauagcg guuucgauag agcugcguca gacgacucgc      60
ccga                                                                  64

<210> SEQ ID NO 55
<211> LENGTH: 61
<212> TYPE: RNA
<213> ORGANISM: Artificial Sequence
```

```
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 55
gggaggacga ugcggugagc gcguauagcg guuucgauag agccucagac gacucgcccg    60
a                                                                    61

<210> SEQ ID NO 56
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 56
gggaggacga ugcggugagc guggcaaacg guuucgauag agccucagac gacucgcccg    60
a                                                                    61

<210> SEQ ID NO 57
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 57
gggaggacga ugcggugagc guguaaaacg guuucgauag agccucagac gacucgcccg    60
a                                                                    61

<210> SEQ ID NO 58
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 58
gggaggacga ugcggugagc guguaaaacg guuucgauag agccucagac gacucgcccg    60
a                                                                    61

<210> SEQ ID NO 59
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
```

```
<221> NAME/KEY: modified_base
<222> LOCATION: (1)..(61)
<223> OTHER INFORMATION: All c's and u's are 2'-F

<400> SEQUENCE: 59
gggaggacga ugcggugggc gucagcauuu cgaucuucgg caccucagac gacucgcccg    60
a                                                                   61

<210> SEQ ID NO 60
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 60
gggaggacga ugcgggaguu guucggcauu uagaucuccg cucccucaga cgacucgccc    60
ga                                                                  62

<210> SEQ ID NO 61
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 61
gggaggacga ugcgggcaaa guucggcauu cagaucucca ugcccucaga cgacucgccc    60
ga                                                                  62

<210> SEQ ID NO 62
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 62
gggaggacga ugcggggcuu cucacauauu cuucucuuuc cccgucagac gacucgcccg    60
a                                                                   61

<210> SEQ ID NO 63
<211> LENGTH: 49
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(49)
<223> OTHER INFORMATION: All c's and u's are 2'-F
```

```
<400> SEQUENCE: 63
gggaggagga ucgguguuca gcauucagau cuucagacga cucgcccga            49

<210> SEQ ID NO 64
<211> LENGTH: 61
<212> TYPE: RNA
<213> ORGANISM: Artificial Sequence
<220> FEATURE:
<221> NAME/KEY: unsure
<222> LOCATION: (30)
<223> OTHER INFORMATION: Description of Artificial Sequence: Completely
      Synthesized Nucleic Acid. N at position 30 is
      a or c or g or u
<220> FEATURE:
<221> NAME/KEY: modified_base
<222> LOCATION: (1)..(61)
<223> OTHER INFORMATION: All c's and u's are 2'-F

<400> SEQUENCE: 64
gggaggacga ugcgguguuc agcauucagn aucuucacgu gucgucagac gacucgcccg  60
a                                                                  61

<210> SEQ ID NO 65
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 65
gggaggacga ugcgguguuc accauucaga ucuucacgug ucgucagacg acucgcccga   60

<210> SEQ ID NO 66
<211> LENGTH: 57
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(57)
<223> OTHER INFORMATION: All c's and u's are 2'-F

<400> SEQUENCE: 66
gggaggacga ugcuguucag cauucagauc uucacgugug ucagacgacu cgcccga      57

<210> SEQ ID NO 67
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 67
gggaggacga ugcgguuucg auagagacuu acaguugagc gcggucagac gacucgcccg  60
a                                                                  61
```

```
<210> SEQ ID NO 68
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 68
gggaggacga ugcgguuugu gauuuggaag uggggggau agggucagac gacucgcccg    60
a                                                                  61

<210> SEQ ID NO 69
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 69
gggaggacga ugcggugagc guggcaaacg guuucgauag agccucagac gacucgcccg    60
a                                                                   61

<210> SEQ ID NO 70
<211> LENGTH: 59
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(59)
<223> OTHER INFORMATION: All c's and u's are 2'-F

<400> SEQUENCE: 70
ggagggcgau ggggugagcg uguaaaaggu ugcgauagag ccucagacga cucgcccga     59

<210> SEQ ID NO 71
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 71
gggaggacga ugcggguauc uuaucuuguu uucguuuuuc ugcccucaga cgaucgcccg    60
a                                                                   61

<210> SEQ ID NO 72
<211> LENGTH: 61
<212> TYPE: RNA
<213> ORGANISM: Artificial Sequence
<220> FEATURE:
<223> OTHER INFORMATION: Description of Artificial Sequence: Completely
```

-continued

Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 72
gggaggacga ugcggagggu ucuuuucauc uucuuucuuu ccccucagac gacucgcccg    60
a                                                                    61

<210> SEQ ID NO 73
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 73
gggaggacga ugcggacgaa gaagguggug gaggaguuuc gugcucagac gacucgcccg    60
a                                                                    61

<210> SEQ ID NO 74
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 74
gggaggacga ugcggacgaa gaagggggug gaggaguuuc gugcucagac gacucgcccg    60
a                                                                    61

<210> SEQ ID NO 75
<211> LENGTH: 42
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(42)
<223> OTHER INFORMATION: All c's and u's are 2'-F

<400> SEQUENCE: 75
gacgaugcgg ucucaugcgu cgagugugag uuuaccuucg uc                       42

<210> SEQ ID NO 76
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

```
<400> SEQUENCE: 76
gggaggacga ugcggcgauu acugggacgg acucgcgaug ugagcccaga cgacucgccc    60
ga                                                                  62

<210> SEQ ID NO 77
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 77
gggaggacga ugcggcgauu acugggacag acucgcgaug ugagcucaga cgacucgccc    60
ga                                                                  62

<210> SEQ ID NO 78
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 78
gggaggacga ugcggcgacu acugggaagg gucgcgaagu gagcccagac gacucgcccg    60
a                                                                   61

<210> SEQ ID NO 79
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 79
gggaggacga ugcggcgauu acugggacag acucgcgaug ugagcucaga cgacucgccc    60
ga                                                                  62

<210> SEQ ID NO 80
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 80
gggaggacga ugcggcgacu acugggagag uacgcgaugu gugcccagac gacucgcccg    60
```

-continued a                                                              61

<210> SEQ ID NO 81
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 81
gggaggacga ugcggguccu cggggaaaau uucgcgacgu gaaccucaga cgacucgccc    60
ga                                                                  62

<210> SEQ ID NO 82
<211> LENGTH: 70
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(70)
<223> OTHER INFORMATION: All c's and u's are 2'-F

<400> SEQUENCE: 82
gggaggacga ugcggcuucu gaagauuauu ucgcgaugug aacuucagac cccucagacg    60
acucgcccga                                                          70

<210> SEQ ID NO 83
<211> LENGTH: 70
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(70)
<223> OTHER INFORMATION: All c's and u's are 2'-F

<400> SEQUENCE: 83
gggaggacga ugcggcuucu gaagauuauu ucgcgaugug aacuccagac cccucagacg    60
acucgcccga                                                          70

<210> SEQ ID NO 84
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 84
gggaggacga ugcggaaagu ggaagugaau ggccgacuug ucggucaga cgacucgccc     60 ga                                                                  62

<210> SEQ ID NO 85

```
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 85
gggaggacga ugcggaaacc aaaucgucga ucuuuccacc gucgucagac gacucgcccg      60
a                                                                     61

<210> SEQ ID NO 86
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 86
gggaggacga ugcggaacac gaaacggagg uugacucgau cuggccagac gacucgcccg      60
a                                                                     61

<210> SEQ ID NO 87
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 87
ggaggacgau gcggaacacg gaagacagug cgacucgauc uggucagacg acucgcccga      60

<210> SEQ ID NO 88
<211> LENGTH: 59
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(59)
<223> OTHER INFORMATION: All c's and u's are 2'-F

<400> SEQUENCE: 88
gggaggacga ugcggaacaa ggacaaaagu gcgauucugu cuggcagacg acucgcccg       59

<210> SEQ ID NO 89
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
```

<222> LOCATION: (1)..(61)
<223> OTHER INFORMATION: All c's and u's are 2'-F

<400> SEQUENCE: 89
gggaggacga ugcggaacag acgacucgcg caacuacucu gacgucagac gacucgcccg    60
a                                                                   61

<210> SEQ ID NO 90
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 90
gggaggacga ugcggaacag guaguugggu gacucugugu gaccucagac gacucgcccg    60
a                                                                   61

<210> SEQ ID NO 91
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 91
ggaggacgau gcggaaccaa aucgucgauc uuuccaccgc ucgucagacg acucgcccga    60

<210> SEQ ID NO 92
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 92
gggaggacga ugcggaaccg cuauugaaug ucacugcuuc gugcucagac gacucgcccg    60
a                                                                   61

<210> SEQ ID NO 93
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 93
gggaggacga ugcggaaccc aaucgucuaa uucgcugcuc aucgucagac gacucgcccg    60

-continued a                                                               61

<210> SEQ ID NO 94
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 94
gggaggacga ugcggaaccc aaucgucuaa uucgcugcuc aucgucagac gacucgcccg      60
a                                                               61

<210> SEQ ID NO 95
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 95
gggaggacga ugcggaacuc aaugggccua cuuuccgug guccucagac gacucgcccg       60
a                                                               61

<210> SEQ ID NO 96
<211> LENGTH: 66
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(66)
<223> OTHER INFORMATION: All c's and u's are 2'-F

<400> SEQUENCE: 96
gggaggacga ugcggaagcg gugagucgug gcuuucuccu cgauccucgu cagacgacuc      60
gcccga                                                          66

<210> SEQ ID NO 97
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 97
gggaggacga ugcggaagga ugacgaggug guugggguuu gugcucagac gacucgcccg      60
a                                                               61

```
<210> SEQ ID NO 98
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 98
gggaggacga ugcggacaag acgagaacgg ggggagcuac cuggccagac gacucgcccg      60
a                                                                     61

<210> SEQ ID NO 99
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 99
gggaggacga ugcggagaca cuaaacaaau uggcgaccug accgucagac gacucgcccg      60
a                                                                     61

<210> SEQ ID NO 100
<211> LENGTH: 69
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(69)
<223> OTHER INFORMATION: All c's and u's are 2'-F

<400> SEQUENCE: 100
gggaggacga ugcggagagg cucagacgac ucgcccgacc acggaugcga ccucagacga      60
cucgcccga                                                             69

<210> SEQ ID NO 101
<211> LENGTH: 59
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(59)
<223> OTHER INFORMATION: All c's and u's are 2'-F

<400> SEQUENCE: 101
gggaggacga ugcggagaug gauggaagug cuagucuucu gggucagac gacucgccc       59

<210> SEQ ID NO 102
<211> LENGTH: 62
<212> TYPE: RNA
<213> ORGANISM: Artificial Sequence
<220> FEATURE:
<223> OTHER INFORMATION: Description of Artificial Sequence: Completely
```

```
            Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 102
gggaggacga ugcggagaug gauggaagug cuagucuuuc ugggucaga cgacucgccc    60 ga                                                                  62

<210> SEQ ID NO 103
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 103
gggaggacga ugcggagcag uugaaagacg ugcguuucgu uuggucagac gacucgcccg    60
a                                                                   61

<210> SEQ ID NO 104
<211> LENGTH: 67
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(67)
<223> OTHER INFORMATION: All c's and u's are 2'-F

<400> SEQUENCE: 104
gggaggacga ugcggagcac aauuuuuucc uuuucuuuuc guccacgugc ucagacgacu    60
cgcccga                                                             67

<210> SEQ ID NO 105
<211> LENGTH: 58
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(58)
<223> OTHER INFORMATION: All c's and u's are 2'-F

<400> SEQUENCE: 105
gggaggacga ugcggagcug augaagauga ucucugaccc cucagacgac ucgccga       58

<210> SEQ ID NO 106
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F
```

```
<400> SEQUENCE: 106
gggaggacga ugcggagcug aaagcgaagu gcgagguguu ugguccagac gacucgcccg    60
a                                                                   61

<210> SEQ ID NO 107
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 107
ggaggacgau gcggagcgaa agugcgagug auugaccagg ugcucagacg acucgcccga    60

<210> SEQ ID NO 108
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 108
gggaggacga ugcggagcgu gagaacaguu gcgagauugc cuggucagac gacucgcccg    60
a                                                                   61

<210> SEQ ID NO 109
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 109
gggaggacga ugcggaggag agugugguga gggucguuug agggucagac gacucgcccg    60
a                                                                   61

<210> SEQ ID NO 110
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 110
gggaggacga ugcggaggag cugaugaaga ugaucucuga ccccucagac gacucgcccg    60
a                                                                   61
```

```
<210> SEQ ID NO 111
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 111
gggaggacga ugcggaguuc ccagccgccu ugauuucucc guggucagac gacucgcccg    60
a                                                                    61

<210> SEQ ID NO 112
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 112
gggaggacga ugcggauaag ugcgagugua ugaggugcgu guggucagac gacucgcccg    60
a                                                                    61

<210> SEQ ID NO 113
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 113
gggaggacga ugcggaucug aggagcucuu cgucgugcug agggucagac gacucgcccg    60
a                                                                    61

<210> SEQ ID NO 114
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 114
gggaggacga ugcggauccg aaucuuccuu acacguccug cucgucagac gacucgcccg    60
a                                                                    61

<210> SEQ ID NO 115
<211> LENGTH: 60
<212> TYPE: RNA
```

```
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 115
ggaggacgau gcggauccgc aaaccgacag cucgaguucc gccucagacg acucgcccga    60

<210> SEQ ID NO 116
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 116
gggaggacga ugcggauggu acuuuagucu uccuugauuc cgccucagac gacucgcccg    60
a                                                                   61

<210> SEQ ID NO 117
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 117
ggaggacgau gcggaugaug acugaacgug cgacucgacc uggccagacg acucgcccga    60

<210> SEQ ID NO 118
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 118
ggaggacgau gcggaugagg aggaagaguc ugaggugcug gggucagacg acucgcccga    60

<210> SEQ ID NO 119
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 119
```

```
gggaggacga ugcggauuuc ggucgacuaa auaggggugg cucgucagac gacucgcccg    60
a                                                                    61

<210> SEQ ID NO 120
<211> LENGTH: 68
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(68)
<223> OTHER INFORMATION: All c's and u's are 2'-F

<400> SEQUENCE: 120
gggaggacga ugcggcaaga ggucagacga cugccccgag uccuccccg gucagacgac    60 ucgcccga                                                             68

<210> SEQ ID NO 121
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 121
gggaggacga ugcggcagug aaaggcgagu uuucuccucu cccucagacg acucgcccga    60

<210> SEQ ID NO 122
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 122
gggaggacga ugcggcaucg uucaggagaa uccacuucgc cucgucagac gacucgcccg    60
a                                                                    61

<210> SEQ ID NO 123
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 123
gggaggacga ugcggcaucu uccuuguucu uccaaccgug cuccucagac gacucgcccg    60
a                                                                    61
```

```
<210> SEQ ID NO 124
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 124
gggaggacga ugcggcaucg uaaacaauuu guuccaucuc cgccucagac gacucgcccg     60
a                                                                    61

<210> SEQ ID NO 125
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 125
gggaggacga ugcggcauug uccaaguuua gcuguccgug cucgucagac gacucgcccg     60
a                                                                    61

<210> SEQ ID NO 126
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 126
gggaggacga ugcggcauag uccggauacu agucaccagc cucguagacg acucgcccga     60

<210> SEQ ID NO 127
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 127
gggaggacga ugcggccguc ucgauccuuc uaugccuucg cucgucagac gacucgcccg     60
a                                                                    61

<210> SEQ ID NO 128
<211> LENGTH: 65
<212> TYPE: RNA
<213> ORGANISM: Artificial Sequence
<220> FEATURE:
<221> NAME/KEY: unsure
```

```
<222> LOCATION: (34)
<223> OTHER INFORMATION: Description of Artificial Sequence: Completely
      Synthesized Nucleic Acid. N at position 34 is
      a or c or g or u
<220> FEATURE:
<221> NAME/KEY: modified_base
<222> LOCATION: (1)..(65)
<223> OTHER INFORMATION: All c's and u's are 2'-F

<400> SEQUENCE: 128
gggaggacga ugcggcggga aguuugaggu guanuaccug uugucugguc agacgacucg    60
cccga                                                               65

<210> SEQ ID NO 129
<211> LENGTH: 67
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(67)
<223> OTHER INFORMATION: All c's and u's are 2'-F

<400> SEQUENCE: 129
gggaggacga ugcggcucaa cucucccaca gacgacucgc ccgggccucc ucagacgacu    60
cgcccga                                                             67

<210> SEQ ID NO 130
<211> LENGTH: 58
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(58)
<223> OTHER INFORMATION: All c's and u's are 2'-F

<400> SEQUENCE: 130
gggaggacga ugcgggacuc cucgaccgac ucgaccggcu cgucagacga cucgccga     58

<210> SEQ ID NO 131
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 131
ggaggacgau gcgggaacca aaucgucgau cuuuccaccg cucgucagac gacucgcccg    60
a                                                                   61

<210> SEQ ID NO 132
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
```

<222> LOCATION: (1)..(61)
<223> OTHER INFORMATION: All c's and u's are 2'-F

<400> SEQUENCE: 132
gggaggacga ugcgggacca ccucgauccu cagcgccauu gcccucagac gacucgcccg    60
a                                                                   61

<210> SEQ ID NO 133
<211> LENGTH: 57
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(57)
<223> OTHER INFORMATION: All c's and u's are 2'-F

<400> SEQUENCE: 133
gggaggacga ugcgggaagu ggaaggguag uugugugacc ucagacgacu cgcccga       57

<210> SEQ ID NO 134
<211> LENGTH: 67
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(67)
<223> OTHER INFORMATION: All c's and u's are 2'-F

<400> SEQUENCE: 134
cggaggacga ugcgggcaaa cuuuuccuuu ucccuuuauc uuccuugccc ucagacgacu    60
cgcccga                                                             67

<210> SEQ ID NO 135
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 135
gggaggacga ugcggggccg acgauucacc aauguucucu cuggucagac gacucgcccg    60
a                                                                   61

<210> SEQ ID NO 136
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 136
ggaggacgau gcggguucc ucaaugacga ucuccauucc gcucgucaga cgacucgccc    60

-continued ag                                                              62

<210> SEQ ID NO 137
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 137
ggaggacgau gcggucgac auugaagcug cucugccuug auccucagac gacucgcccg    60
a                                                                   61

<210> SEQ ID NO 138
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 138
gggaggacga ugcgguccaa uucguucuca ugccuuuccg cucgucagac gacucgcccg    60
a                                                                   61

<210> SEQ ID NO 139
<211> LENGTH: 59
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(59)
<223> OTHER INFORMATION: All c's and u's are 2'-F

<400> SEQUENCE: 139
gggaggacga ugcgguccgc aaguuuagca cucacugccu cgucagacga cucgcccga     59

<210> SEQ ID NO 140
<211> LENGTH: 58
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(58)
<223> OTHER INFORMATION: All c's and u's are 2'-F

<400> SEQUENCE: 140
gggaggacga ugcgguccac aucgaauuuu cuguccguuc gucagacgac ucgcccga      58

<210> SEQ ID NO 141
<211> LENGTH: 63
<212> TYPE: RNA
<213> ORGANISM: Artificial Sequence

```
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(63)
<223> OTHER INFORMATION: All c's and u's are 2'-F

<400> SEQUENCE: 141
gggaggacga ugcggucgau guucuuccuc accacugcuc gucgccucag acgacucgcc    60
cga                                                                 63

<210> SEQ ID NO 142
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 142
gggaggacga ugcggucgag cugagagggg cuacuuguuc uggucacaga cgacucgccc    60
ga                                                                  62

<210> SEQ ID NO 143
<211> LENGTH: 63
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(63)
<223> OTHER INFORMATION: All c's and u's are 2'-F

<400> SEQUENCE: 143
gggaggacga ugcgguggaa gcgaaugggc uagggugggc ugaccuccag acgacucgcc    60
cga                                                                 63

<210> SEQ ID NO 144
<211> LENGTH: 64
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(64)
<223> OTHER INFORMATION: All c's and u's are 2'-F

<400> SEQUENCE: 144
gggaggacga ugcgguggac uucuuuuccu cuuccuccuu ccgccgguca gacgacucgc    60
ccga                                                                64

<210> SEQ ID NO 145
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
```

```
<221> NAME/KEY: modified_base
<222> LOCATION: (1)..(60)
<223> OTHER INFORMATION: All c's and u's are 2'-F

<400> SEQUENCE: 145
ggaggacgau gcgguuccaa aucgucuaag caucgcucgc ucgucagacg acucgcccag    60

<210> SEQ ID NO 146
<211> LENGTH: 62
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(62)
<223> OTHER INFORMATION: All c's and u's are 2'-F

<400> SEQUENCE: 146
gggaggacga ugcgguucca caucgcaauu uucuguccgu gcucgucaga cgacucgccc    60
ga                                                                    62

<210> SEQ ID NO 147
<211> LENGTH: 60
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(60)
<223> OTHER INFORMATION: All c's and u's are 2'-F

<400> SEQUENCE: 147
gggaggacga ugcgguucca caucgaauuu ucuguccgug ucgucagacg acucgcccga    60

<210> SEQ ID NO 148
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 148
gggaggacga ugcgguuccg aucgacucca cauacaucug cucgucagac gacucgcccg    60
a                                                                     61

<210> SEQ ID NO 149
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 149
gggaggacga ugcgguuccg acaucgaugu ugcucuucgc cucgucagac gacucgcccg    60
```

-continued a                                                              61

<210> SEQ ID NO 150
<211> LENGTH: 63
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(63)
<223> OTHER INFORMATION: All c's and u's are 2'-F

<400> SEQUENCE: 150
gggaggacga ugcgguuccg aaguucuucc cccgagccuu ccccuccag acgacucgcc    60 cga                                                            63

<210> SEQ ID NO 151
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 151
gggaggacga ugcgguuccg acgauucucc aauguucucu cggucagac gacucgcccg    60 a                                                              61

<210> SEQ ID NO 152
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 152
gggaggacga ugcgguuccg acgauucucc aaucuucucu cggucagac gacucgcccg    60 a                                                              61

<210> SEQ ID NO 153
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 153
gggaggacga ugcgguuccg caaguuuaga cacucacugc cucgucagac gacucgcccg    60
a                                                              61

<210> SEQ ID NO 154

```
<211> LENGTH: 61
<212> TYPE: RNA
<213> ORGANISM: Artificial Sequence
<220> FEATURE:
<221> NAME/KEY: unsure
<222> LOCATION: (33)
<223> OTHER INFORMATION: Description of Artificial Sequence: Completely
      Synthesized Nucleic Acid. N at position 33 is
      a or c or g or u
<220> FEATURE:
<221> NAME/KEY: modified_base
<222> LOCATION: (1)..(61)
<223> OTHER INFORMATION: All c's and u's are 2'-F

<400> SEQUENCE: 154
gggaggacga ugcgguuccg caaaguagau aunucauccg cacgucagac gacucgcccg    60
a                                                                   61

<210> SEQ ID NO 155
<211> LENGTH: 61
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(61)
<223> OTHER INFORMATION: All c's and u's are 2'-F

<400> SEQUENCE: 155
gggaggacga ugcgguugag uggacagugc gauucguuuu ggggucagac gacucgcccg    60
a                                                                   61

<210> SEQ ID NO 156
<211> LENGTH: 98
<212> TYPE: DNA
<213> ORGANISM: Artificial Sequence
<220> FEATURE:
<221> NAME/KEY: unsure
<222> LOCATION: (33)..(72)
<223> OTHER INFORMATION: Description of Artificial Sequence: Completely
      Synthesized Nucleic Acid.  N's at positions 33-72
      are a or c or g or t.

<400> SEQUENCE: 156
taatacgact cactataggg aggacgatgc ggnnnnnnnn nnnnnnnnnn nnnnnnnnnn    60
nnnnnnnnnn nnnnnnnnnn nncagacgac tcgcccga                           98

<210> SEQ ID NO 157
<211> LENGTH: 81
<212> TYPE: RNA
<213> ORGANISM: Artificial Sequence
<220> FEATURE:
<221> NAME/KEY: unsure
<222> LOCATION: (16)..(65)
<223> OTHER INFORMATION: Description of Artificial Sequence: Completely
      Synthesized Nucleic Acid.  N's at positions 16-65
      are a or c or g or u.
<220> FEATURE:
<221> NAME/KEY: modified_base
<222> LOCATION: (1)..(81)
<223> OTHER INFORMATION: All c's and u's are 2'-NH2

<400> SEQUENCE: 157
gggaggacga ugcggnnnnn nnnnnnnnnn nnnnnnnnnn nnnnnnnnnn nnnnnnnnnn    60
nnnnncagac gacucgcccg a                                             81
```

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Completely
      Synthesized Nucleic Acid

<400> SEQUENCE: 158
taatacgact cactataggg agataagaat aaacgctcaa                           40

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Completely
      Synthesized Nucleic Acid

<400> SEQUENCE: 159
gcctgttgtg agcctcctgt cgaa                                           24

<210> SEQ ID NO 160
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'-F

<400> SEQUENCE: 160
cgaugcgguc ucaugcgucg agugugaguu uaccuucg                            38

<210> SEQ ID NO 161
<211> LENGTH: 36
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(36)
<223> OTHER INFORMATION: All c's and u's are 2'-F

<400> SEQUENCE: 161
gaugcggucu caugcgucga gugugaguuu accuuc                              36

<210> SEQ ID NO 162
<211> LENGTH: 34
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(34)
<223> OTHER INFORMATION: All c's and u's are 2'-F

<400> SEQUENCE: 162
augcggucuc augcgucgag ugugaguuua ccuu                                34

<210> SEQ ID NO 163
<211> LENGTH: 90
<212> TYPE: DNA

```
<213> ORGANISM: Artificial Sequence
<220> FEATURE:
<223> OTHER INFORMATION: Description of Artificial Sequence: Completely
      Synthesized Nucleic Acid

<400> SEQUENCE: 163
gggagataag aataaacgct caaggacgat gcggtctcat gcgtcgagtg tgagtttacc    60
ttcgtcttcg acaggaggct cacaacaggc                                    90

<210> SEQ ID NO 164
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 164
gggagauaag aauaaacgcu caagugcgac gcggucucga gcgcggaguu cgaguuuacc    60
uucgcauucg acaggaggcu cacaacaggc                                    90

<210> SEQ ID NO 165
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 165
gggagauaag aauaaacgcu caagcucgac gcggucccag gcguggaguc uggguuuacc    60
uucgaguucg acaggaggcu cacaacaggc                                    90

<210> SEQ ID NO 166
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 166
gggagauaag aauaaacgcu caagaaccac gcggucucag gcguagaguc ugaguuuacc    60
uugguuuucg acaggaggcu cacaacaggc                                    90

<210> SEQ ID NO 167
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F
```

<400> SEQUENCE: 167
gggagauaag aauaaacgcu caagaaccac gcggucucag gcguagaguc uguguuuacc    60
uugguuuucg acaggaggcu cacaacaggc    90

<210> SEQ ID NO 168
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 168
gggagauaag aauaaacgcu caagugcgac gcggucucga gcgcggaguu cgaguucacc    60
uucgcauucg acaggaggcu cacaacaggc    90

<210> SEQ ID NO 169
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 169
gggagauaag aauaaacgcu caagcacaac gcggucucau gcgucgagua ugaguuuacc    60
uuuguguucg acaggaggcu cacaacaggc    90

<210> SEQ ID NO 170
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 170
gggagauaag aauaaacgcu caagguccuc gcggucucau gcgccgagua ugaguuuacc    60
uaggacuucg acaggaggcu cacaacaggc    90

<210> SEQ ID NO 171
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 171
gggagauaag aauaaacgcu caaggucguc gcggucugau gcgcugagua ucaguuuacc    60
uacgacuucg acaggaggcu cacaacaggc                                            90

<210> SEQ ID NO 172
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 172
gggagauaag aauaaacgcu caagguacac gcggucugac gcgcugagug ucaguuuacc           60
uuguacuucg acaggaggcu cacaacaggc                                            90

<210> SEQ ID NO 173
<211> LENGTH: 91
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(91)
<223> OTHER INFORMATION: All c's and u's are 2'-F

<400> SEQUENCE: 173
gggagauaag aauaaacgcu caagaaacca cgcggucuca ggcgcagagu cugaguuuac           60
cuucgcauuc gacaggaggc ucacaacagg c                                          91

<210> SEQ ID NO 174
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 174
gggagauaag aauaaacgcu caagaaccac gcggucucag gcgcagaguc ugaguuuacc           60 uugguuucg acaggaggcu cacaacaggc                                             90

<210> SEQ ID NO 175
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 175
gggagauaag aauaaacgcu caaggacgcc gcggucucag gcgcugaguc ugaguuuacc           60
ugcgucuucg acaggaggcu cacaacaggc                                            90

```
<210> SEQ ID NO 176
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 176
gggagauaag aauaaacgcu caaggcugac gcggucucag gcguggaguc ugaguuuacc      60
uucggcuucg acaggaggcu cacaacaggc                                      90

<210> SEQ ID NO 177
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 177
gggagauaag aauaaacgcu caagcaugac gcggucucag gcguggaguc ugaguuuacc      60
uucguguucg acaggaggcu cacaacaggc                                      90

<210> SEQ ID NO 178
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 178
gggagauaag aauaaacgcu caaggucgac gcggucucag gcguugaguc uguguuuacc      60
uucgacuucg acaggaggcu cacaacaggc                                      90

<210> SEQ ID NO 179
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 179
gggagauaag aauaaacgcu caaggucgac gcggucucag gcguugaguc uguguuuacc      60
uucgacuucg acaggaggcu cacaacaggc                                      90

<210> SEQ ID NO 180
<211> LENGTH: 90
<212> TYPE: RNA
<213> ORGANISM: Artificial Sequence
```

```
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 180
gggagauaag aauaaacgcu caaggacgcc gcggucucag gcguugaguc ugaguuuacc    60
ugcgucuucg acaggaggcu cacaacaggc                                    90

<210> SEQ ID NO 181
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 181
gggagauaag aauaaacgcu caaggacgac gcggucugau gcgcugagug ucaguuuacc    60
uucgucuucg acaggaggcu cacaacaggc                                    90

<210> SEQ ID NO 182
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 182
gggagauaag aauaaacgcu caagaacgac gcggucugau gcgcugagug ucaguguacc    60
uucgucuucg acaggaggcu cacaacaggc                                    90

<210> SEQ ID NO 183
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 183
gggagauaag aauaaacgcu caaggucgac gcggucugau gcguagagug ucaguuuacc    60
uucgacuucg acaggaggcu cacaacaggc                                    90

<210> SEQ ID NO 184
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
```

```
<221> NAME/KEY: modified_base
<222> LOCATION: (1)..(90)
<223> OTHER INFORMATION: All c's and u's are 2'-F

<400> SEQUENCE: 184
gggagauaag aauaaacgcu caaggucgac gcggucugau gcguagagug ucaguucacc    60
uucgacuucg acaggaggcu cacaacaggc                                    90

<210> SEQ ID NO 185
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 185
gggagauaag aauaaacgcu caaguacgac gcgucccgu gcguggagug cggguuuacc     60
uucguauucg acaggaggcu cacaacaggc                                    90

<210> SEQ ID NO 186
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 186
gggagauaag aauaaacgcu caaggacgac gcggucugau gcgcagagug ucgguuuacc    60
uuugucuucg acaggaggcu cacaacaggc                                    90

<210> SEQ ID NO 187
<211> LENGTH: 90
<212> TYPE: RNA
<213> ORGANISM: Artificial Sequence
<220> FEATURE:
<221> NAME/KEY: unsure
<222> LOCATION: (33)
<223> OTHER INFORMATION: Description of Artificial Sequence: Completely
      Synthesized Nucleic Acid. N at position 33 is
      a or c or g or u
<220> FEATURE:
<221> NAME/KEY: modified_base
<222> LOCATION: (1)..(90)
<223> OTHER INFORMATION: All c's and u's are 2'-F

<400> SEQUENCE: 187
gggagauaag aauaaacgcu caaggacgac gcngucugau gcgcagagug ucaguuuacc    60
uucgacuucg acaggaggcu cacaacaggc                                    90

<210> SEQ ID NO 188
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
```

<222> LOCATION: (1)..(90)
<223> OTHER INFORMATION: All c's and u's are 2'-F

<400> SEQUENCE: 188
gggagauaag aauaaacgcu caaggacgac gcggucugau gcgcagagug ucaguuuacc    60
uucgucuucg acaggaggcu cacaacaggc                                    90

<210> SEQ ID NO 189
<211> LENGTH: 90
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(90)
<223> OTHER INFORMATION: All c's and u's are 2'-F

<400> SEQUENCE: 189
gggagauaag aauaaacgcu caaggacgac gcggucggau gcgcagagug uccguuuacc    60
uucgucuucg acaggaggcu cacaacaggc                                    90

<210> SEQ ID NO 190
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'-F.  A's and g's at
      positions 2, 8, 15, 22 and 28 are 50 % 2'-OH and
      50% 2'-O-Methyl

<400> SEQUENCE: 190
cgccgcgguc ucaggcgcug agucugaguu uaccugcg                           38

<210> SEQ ID NO 191
<211> LENGTH: 37
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(37)
<223> OTHER INFORMATION: All c's and u's are 2'F.   A's and g's at
      positions 7, 13, 17, 27 and 36 are 50% 2'-OH and
      50% 2'-O-Methyl

<400> SEQUENCE: 191
cgccgcgguu cgggcgcuga gucugaguuu accugcg                            37

<210> SEQ ID NO 192
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'F.  A's and g's at
      positions 15, 21, 26, 32 and 38 are 50% 2'-OH and 50%
      2'-O-Methyl

```
<400> SEQUENCE: 192
cgccgcgguc ucaggcgcug agucugaguu uaccugcg                                38

<210> SEQ ID NO 193
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'F.  A's and g's at
      positions 2, 7, 8, 13, 14, 15, 20, 21, 22, 26, 27,
      28, 36 and 38 can be 2'-O-Methyl.  A's and g's
      at positions 5, 17 and 32 must be 2'-OH

<400> SEQUENCE: 193
cgaugcgguc ucaugcgucg agugugaguu uaccuucg                                38

<210> SEQ ID NO 194
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'-F

<400> SEQUENCE: 194
cgccgcgguc ucaggcgcug agucugaguu uaccugcg                                38

<210> SEQ ID NO 195
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'-F.   G at position 20 is
      2'-O-Methyl

<400> SEQUENCE: 195
cgccgcgguc ucaggcgcug agucugaguu uaccugcg                                38

<210> SEQ ID NO 196
<211> LENGTH: 38
<212> TYPE: RNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(38)
<223> OTHER INFORMATION: All c's and u's are 2'-F.  A's and g's at
      positions 2, 7, 8, 13, 14, 15, 20, 21, 22, 26, 27,
      28, 36 and 38 are 2'-O-Methyl

<400> SEQUENCE: 196
cgccgcgguc ucaggcgcug agucugaguu uaccugcg                                38
```

```
<210> SEQ ID NO 197
<211> LENGTH: 37
<212> TYPE: DNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(37)
<223> OTHER INFORMATION: All c's and t's are 2'-F. All nucleotides are
      bound by a phosphorothioate linkage

<400> SEQUENCE: 197
ggcggggcta cgtaccgggg ctttgtaaaa ccccgcc                               37

<210> SEQ ID NO 198
<211> LENGTH: 25
<212> TYPE: DNA
<213> ORGANISM: Artificial Sequence
<220> FEATURE:
<223> OTHER INFORMATION: Description of Artificial Sequence: Completely
      Synthesized Nucleic Acid
<220> FEATURE:
<221> NAME/KEY: modified_base
<222> LOCATION: (1)..(25)
<223> OTHER INFORMATION: All c's and t's are 2'-F. All nucleotides are
      bound by a phosphorothioate linkage

<400> SEQUENCE: 198
ctctcgcacc catctctctc cttct                                           25
```